United States Patent [19]
Farbood et al.

[11] Patent Number: 5,023,347
[45] Date of Patent: Jun. 11, 1991

[54] PROCESS FOR PREPARING COMPOSITIONS CONTAINING UNSATURATED LACTONES, PRODUCTS PRODUCED THEREBY AND ORGANOLEPTIC USES OF SAID PRODUCTS

[75] Inventors: Mohamad I. Farbood, Holmdel; James A. Morris, Wall; Mark A. Sprecker, Sea Bright; Lynda J. Bienkowski, Perth Amboy; Kevin P. Miller, Middletown; Manfred H. Vock, Locust; Myrna L. Hagedorn, Edison, all of N.J.

[73] Assignee: International Flavors & Fragrances Inc., New York, N.Y.

[21] Appl. No.: 545,610

[22] Filed: Jun. 29, 1990

Related U.S. Application Data

[60] Division of Ser. No. 279,065, Dec. 2, 1988, Pat. No. 4,960,597, which is a continuation-in-part of Ser. No. 228,512, Aug. 5, 1988, Pat. No. 4,946,782.

[51] Int. Cl.$^5$ .................. C07D 307/04; C07D 307/32; C07D 313/02
[52] U.S. Cl. .................................... 549/263; 549/266; 549/295
[58] Field of Search ........................ 549/263, 266, 295

[56] References Cited

U.S. PATENT DOCUMENTS 3,621,035 11/1971 Lakodey et al. .................. 549/266
4,011,177 3/1977 Ansari et al. .................... 549/323
4,560,656 12/1985 Farbood et al. .................. 435/146

FOREIGN PATENT DOCUMENTS 0258993 3/1988 European Pat. Off. .
2603048 2/1988 France .
63-39594 2/1988 Japan .
WO83/01072 3/1983 PCT Int'l Appl. .
634570 2/1983 Switzerland .

Primary Examiner—C. Warren Ivy
Assistant Examiner—Ba K. Trinh
Attorney, Agent, or Firm—Arthur L. Liberman

[57] ABSTRACT

Described is a process for the preparation of compositions of matter containing unsaturated lactones defined according to the generic structure:

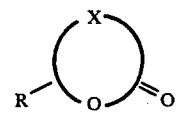

wherein R represents $C_6$ alkyl or alkenyl; and X represents $C_2$, $C_4$ or $C_6$ alkylene or alkenylene; with the provisos that R is $C_6$ alkyl when X is alkenylene and R is $C_6$ alkenyl when X is alkylene by means of the sequential steps of (i) fermentation of castor oil or ricinoleic acid using a microorganism selected from the group consisting of:
Candida petrophilum, ATCC 20226;
Candida oleophila, ATCC 20177;
Candida sp., ATCC 20504; and
Candida sake, ATCC 28137
whereby gamma hydroxydecanoic acid and a mixture of other acids defined according to the generic structure:

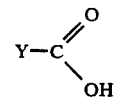

is formed wherein Y represents an oxo-saturated, oxo-unsaturated or di-unsaturated $C_9$, $C_{11}$ or $C_{13}$ moiety according to the reaction:

(Abstract continued on next page.)

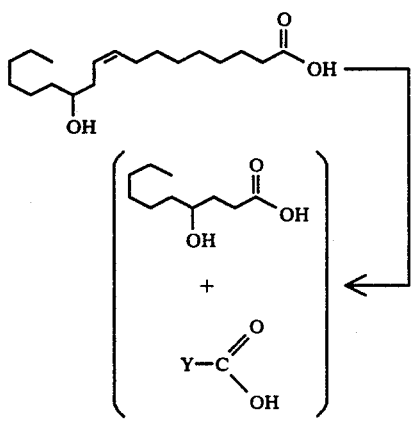

(ii) lactonization of the resulting gamma hydroxydecanoic acid by means of simultaneous acidification and heating according to the reaction:

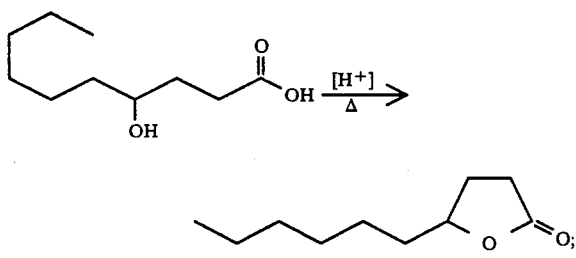

and (iii) lactonization (via distillation) of one or more of the resulting acids defined according to the structure:

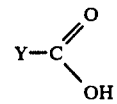

to form one or more lactones defined according to the generic structure:

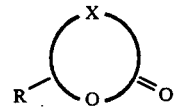

according to the reaction:

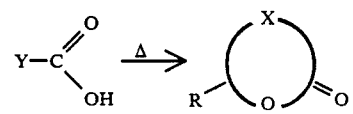

wherein the sum of the number of carbon atoms in the X moiety and in the R moiety is equal to the number of carbon atoms in the Y moiety minus 1.

Also described are the products produced according to such process as well as their organoleptic utilities for augmenting or enhancing the aroma or taste or consumable materials selected from the group consisting of perfume compositions, colognes, perfumed articles, perfumed polymers, foodstuffs, chewing gums, medicinal products, toothpastes, chewing tobaccos and smoking tobaccos.

1 Claim, 20 Drawing Sheets

FIG. II

PROCESS FOR PREPARING COMPOSITIONS CONTAINING UNSATURATED LACTONES, PRODUCTS PRODUCED THEREBY AND ORGANOLEPTIC USES OF SAID PRODUCTS

This is a divisional of application for U.S. application Ser. No. 279,065 filed Dec. 2, 1988, now U.S. Pat. No. 4,960,597 issued Oct. 2, 1990 which is a continuation-in-part of application for U.S. application Ser. No. 228,512 filed Aug. 5, 1988, now U.S. Pat. No. 4,946,782 issued on Aug. 7, 1990.

BACKGROUND OF THE INVENTION

This invention is concerned with a microbial process for the production of compositions of matter containing unsaturated lactones.

Considerable time and effort have been expended by microbiologists in the search for better processes for the production of unsaturated lactones; and more generally lactones per se. U.S. Pat. No. 3,076,750 discloses a method of preparing certain optically active lactones and the corresponding hydroxycarboxylic acids by microbial reduction of ketocarboxylic acids. The metabolism of ricinoleic acid by some Candida strains was investigated by Okui, et al (J. Biochemistry, 54, 536-540, 1963) who showed that gamma hydroxydecanoic acid was an intermediate in the oxidative degradation of ricinoleic acid. However, only trace amounts of gamma hydroxydecanoic acid were recovered from the fermentation medium due to the metabolysis of gamma hydroxydecanoic acid upon completion of the fermentation, and the toxicity of ricinoleic acid to the microorganism, which limits the amount of substrate that can be used.

U.S. Pat. No. 4,560,656 provided a method of producing optically active gamma hydroxydecanoic acid comprising culturing or incubating a microorganism capable of hydrolyzing castor oil, and effecting beta-oxidation of the resulting hydrolysate in the presence of castor oil, to produce gamma hydroxydecanoic acid.

U.S. Pat. No. 4,560,656 also provided a method of producing optically active gamma hydroxydecanoic acid comprising enzymatically hydrolyzing castor oil using lipase to form an enzymatic hydrolysate and culturing or incubating a microorganizm capable of effecting beta-oxidation of the enzymatic hydrolysate in the presence of said hydrolysate to produce gamma hydroxydecanoic acid.

U.S. Pat. No. 4,560,656 also provided a method of producing optically active gamma hydroxydecanoic acid comprising culturing or incubating a microorganism capable of hydrolyzing castor oil and a microorganism capable of effecting beta-oxidation of castor oil hydrolysate in the presence of castor oil to produce gamma hydroxydecanoic acid.

European Published Patent Application No. 258993 published on Apr. 9, 1988 discloses a process for the production of optically active gamma hydroxydecanoic acid suitable for conversion to optically active gamma decalactone. The process covers steps of:

(a) culturing *sporobolomyces odorous*; and/or *rhodotorula glutinis* on a medium containing a ricinoleic acid source at 15°-35° C. at a pH of 3-9 and optionally; and
(b) lactonizing the resulting gamma hydroxydecanoic acid to gamma decalactone.

Nothing in the prior art however discloses the ability by means of fermentation to create a novel mixture of unsaturated lactones together with, optionally, gamma decalactone found to be useful in augmenting or enhancing the organoleptic properties of consumable materials.

In the flavor and fragrance art, a need has arisen for the development and efficient production of naturally occurring lactones which have heretofor been found to be useful and necessary in the creation of flavor formulations used in augmenting or enhancing the aroma or taste of foodstuffs, chewing gums, toothpastes, medicinal products, chewing tobaccos and smoking tobaccos and also useful in augmenting or enhancing the aroma of perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like).

Although U.S. Pat. No. 4,560,656 has partially fulfilled the need for provision of saturated gamma decalactone defined according to the structure:

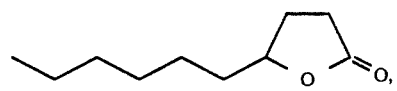

nothing in the prior art sets forth the creation of unsaturated lactones defined generically according to the structure:

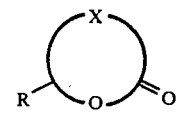

and defined more specifically according to the structures:

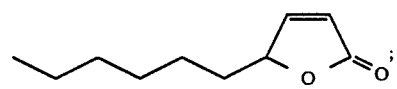

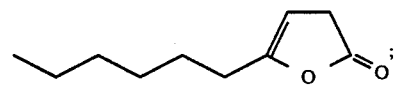

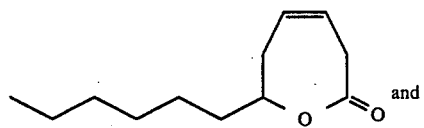

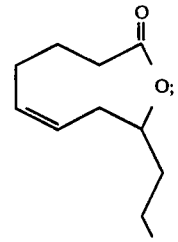

3

-continued

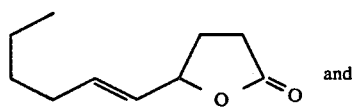 and

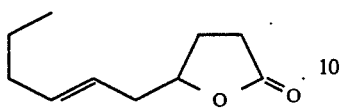

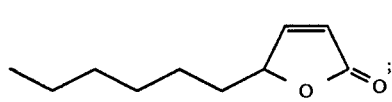

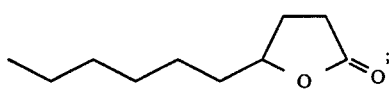

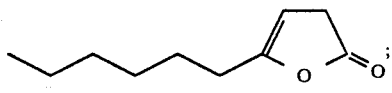

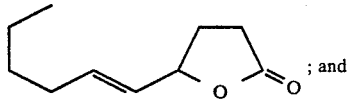 ; and

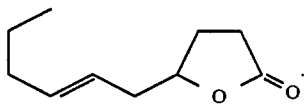

Figure 2:
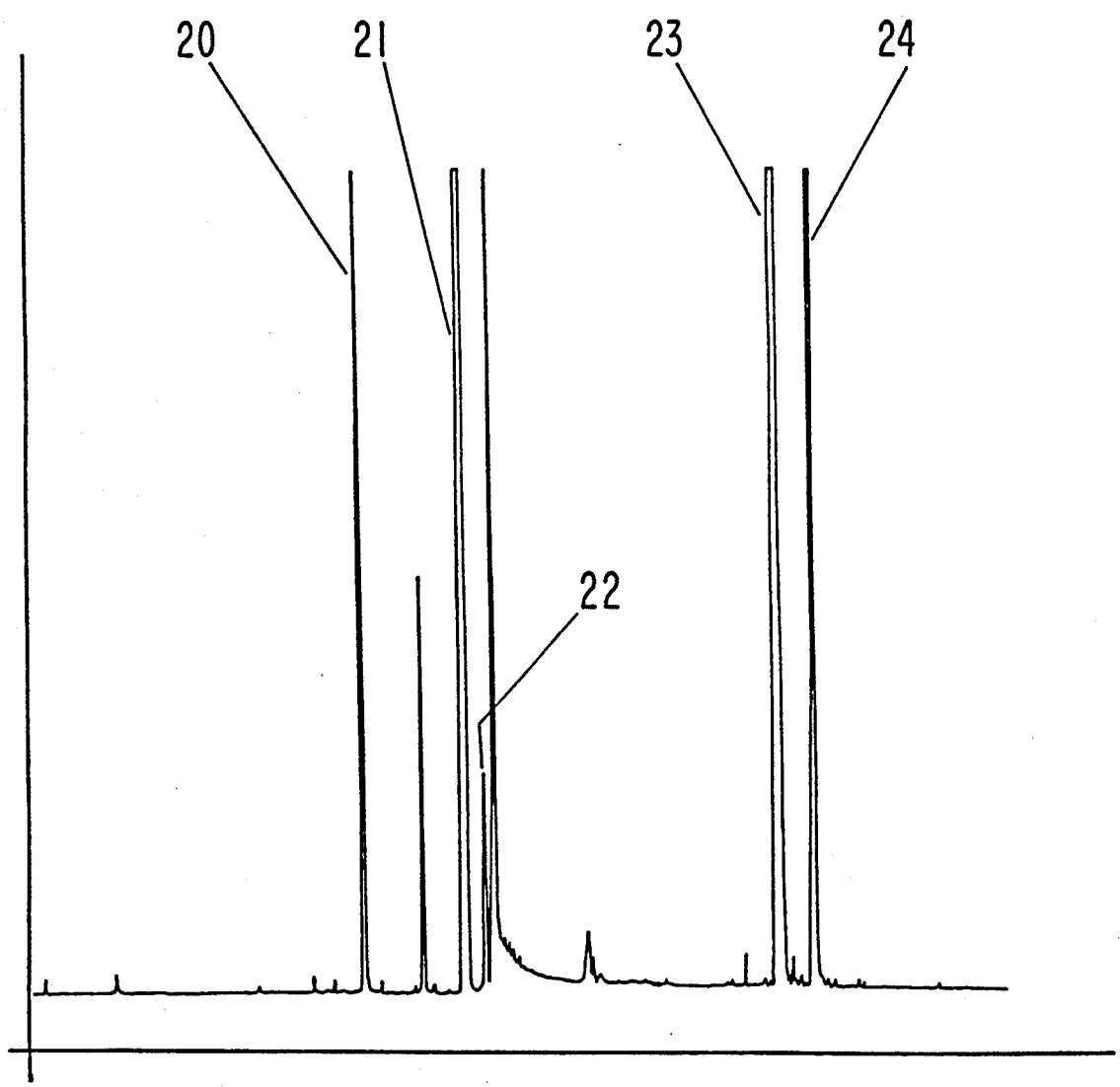

FIG. 2 is the GLC profile for the reaction product of Example I containing the compounds having the structures:

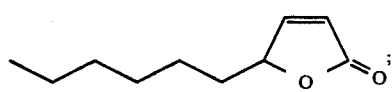

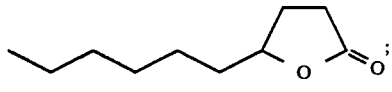

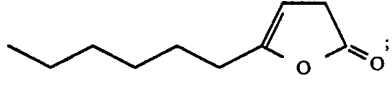

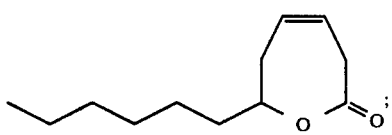

4

-continued

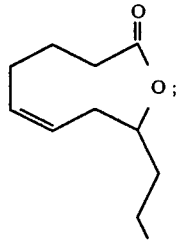

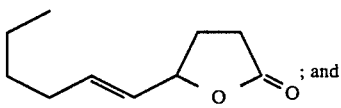 ; and

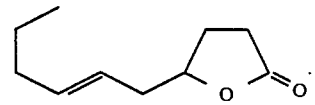

Figure 3:
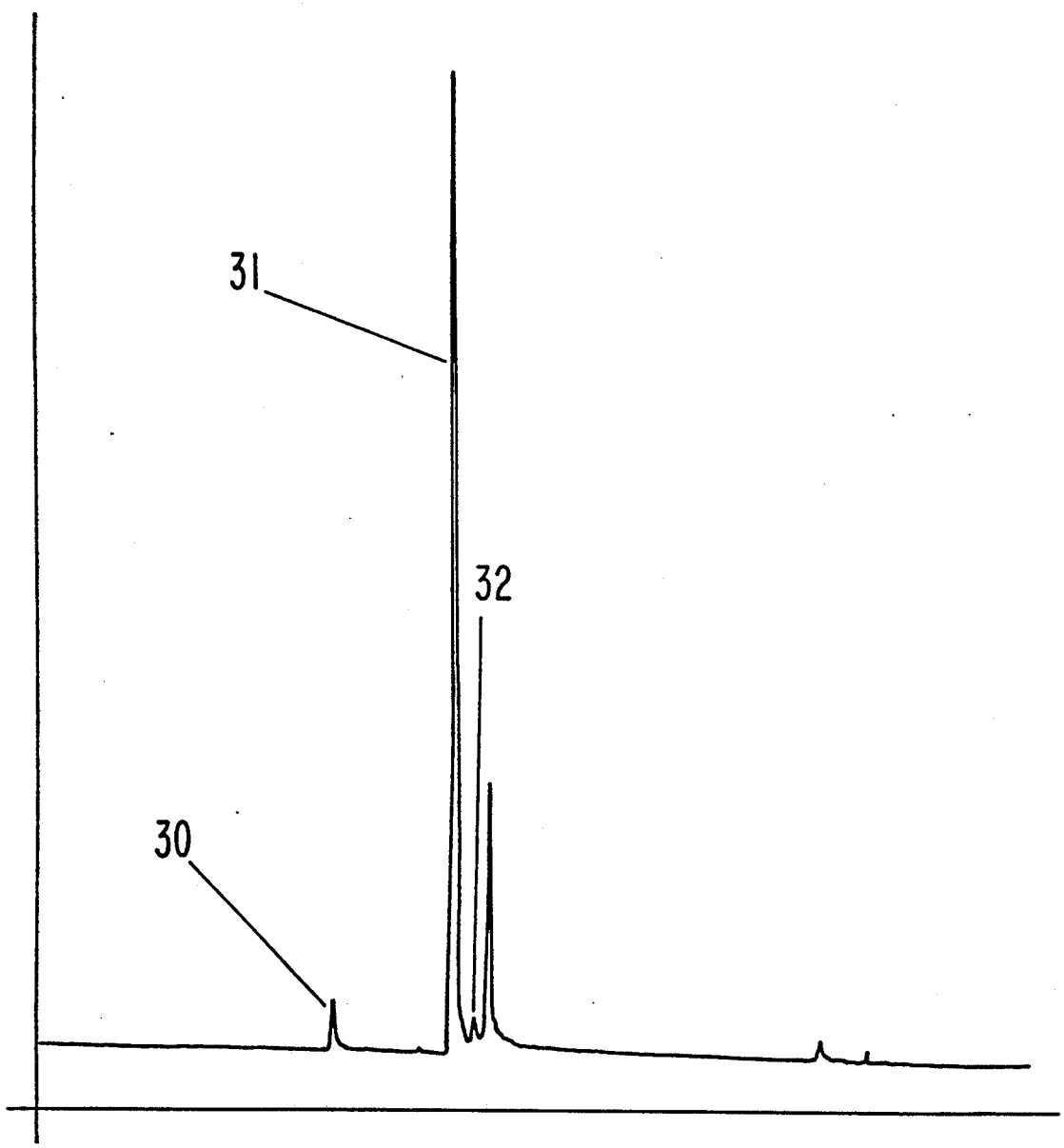

FIG. 3 is the GLC profile for the reaction product of Example II containing the compounds having the structures:

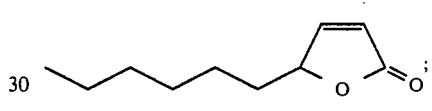

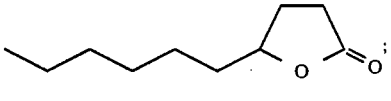

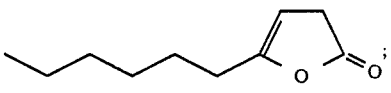

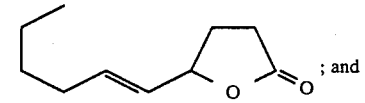 ; and

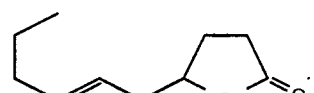

Figure 4:
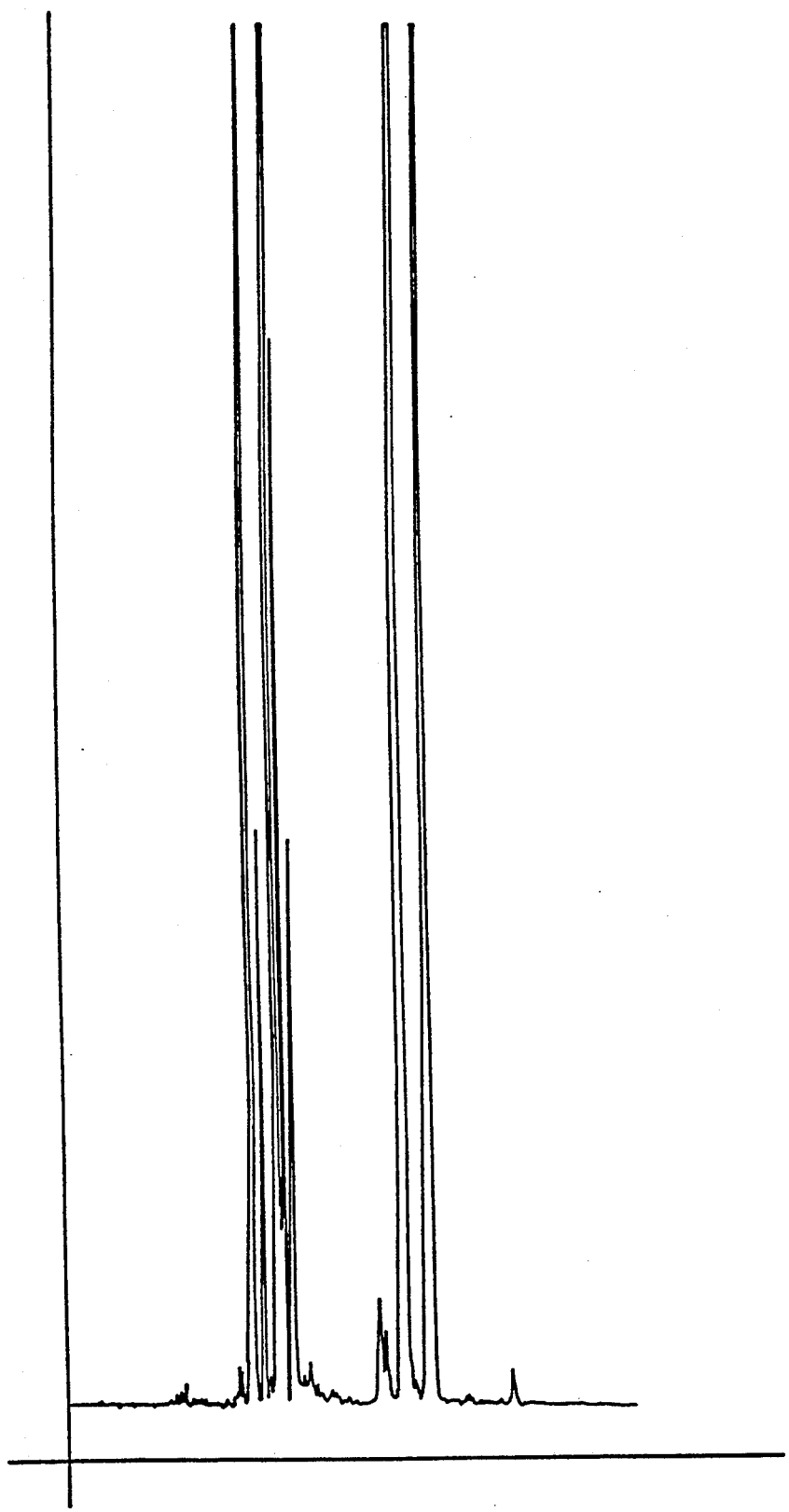

FIG. 4 is the GLC profile for Fraction 19 of the distillation of the reaction product of Example II.

Figure 5:
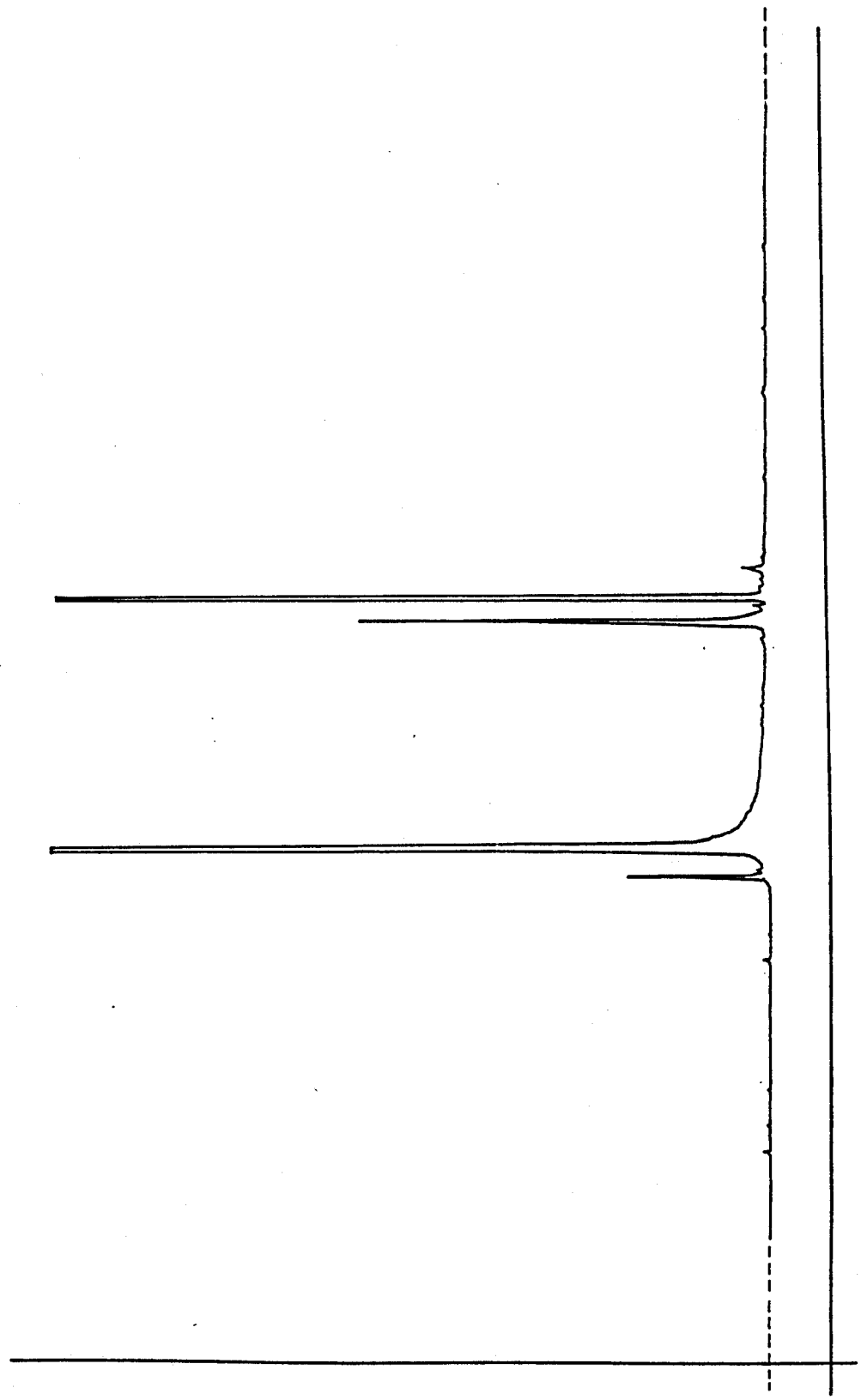

FIG. 5 is the GLC profile for the reaction product of Example III.

Figure 6:
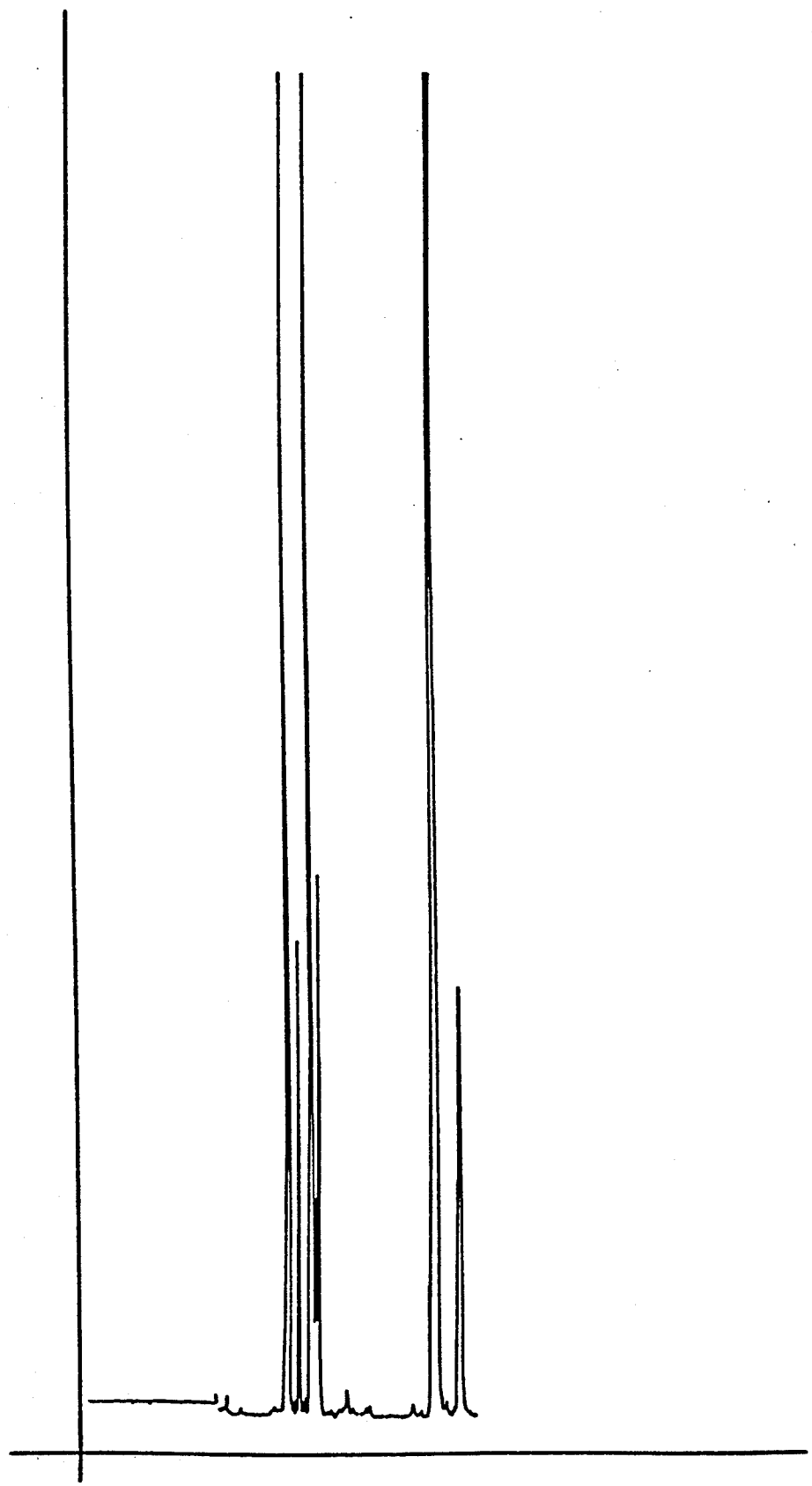

FIG. 6 is the GLC profile for Fraction 23 of the distillation of the reaction product of Example V.

Figure 7:
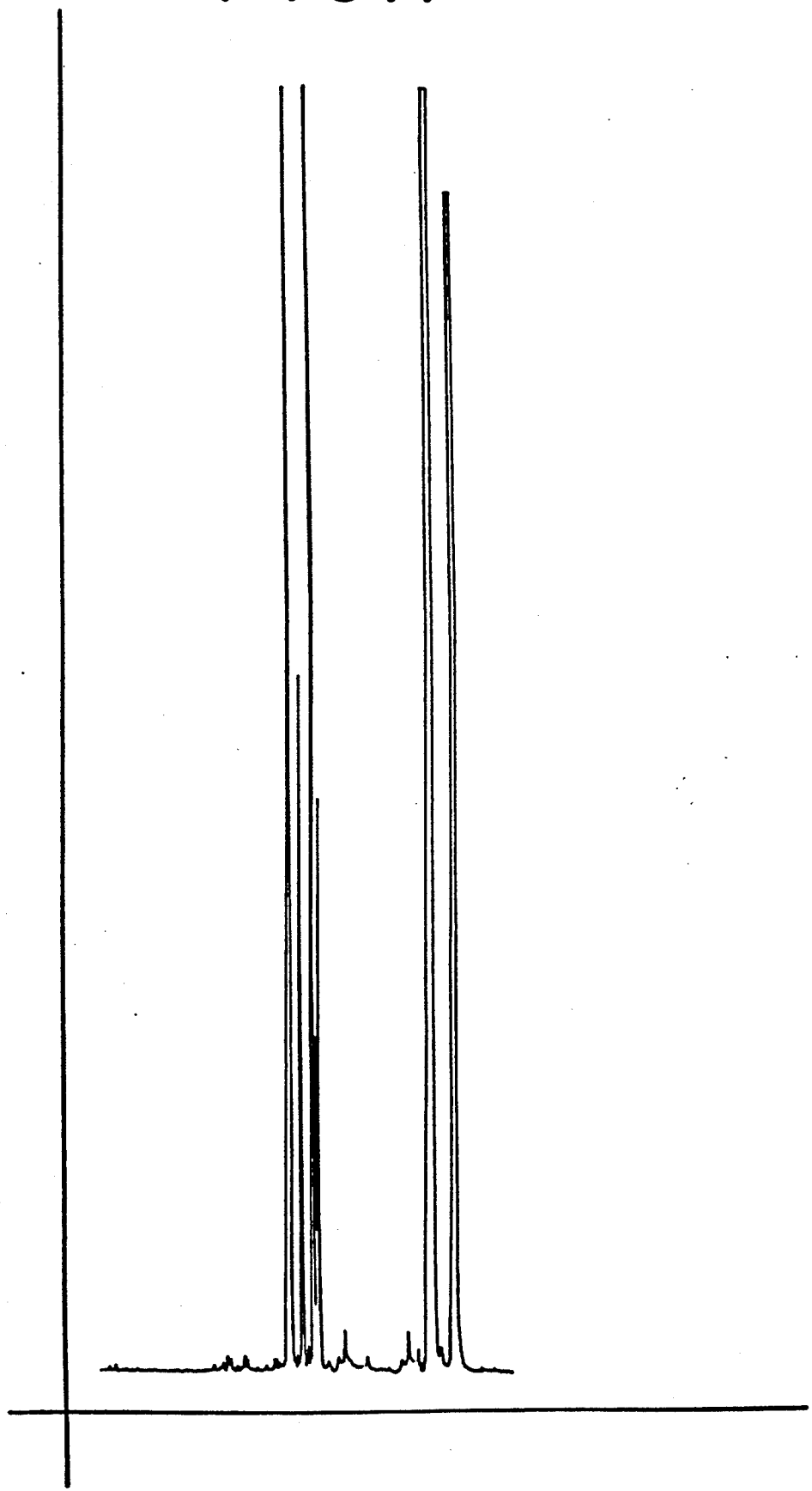

FIG. 7 is the GLC profile for Fraction 24 of the distillation of the reaction product of Example V.

Figure 8:
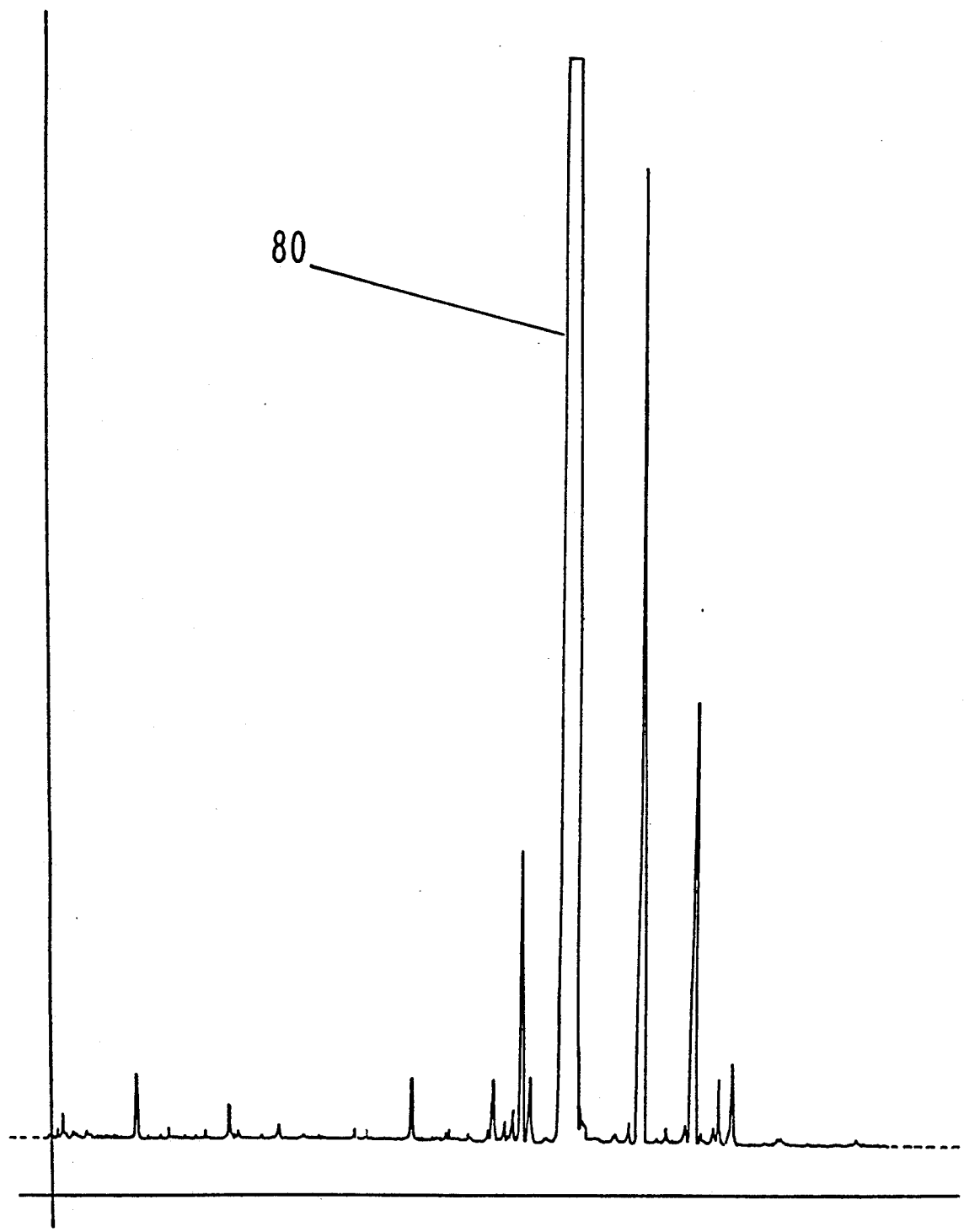

FIG. 8 is the GLC profile for Fraction 1 of the distillation of the reaction product of Example V containing the compound having the structure:

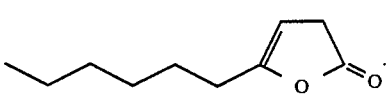

Figure 9:
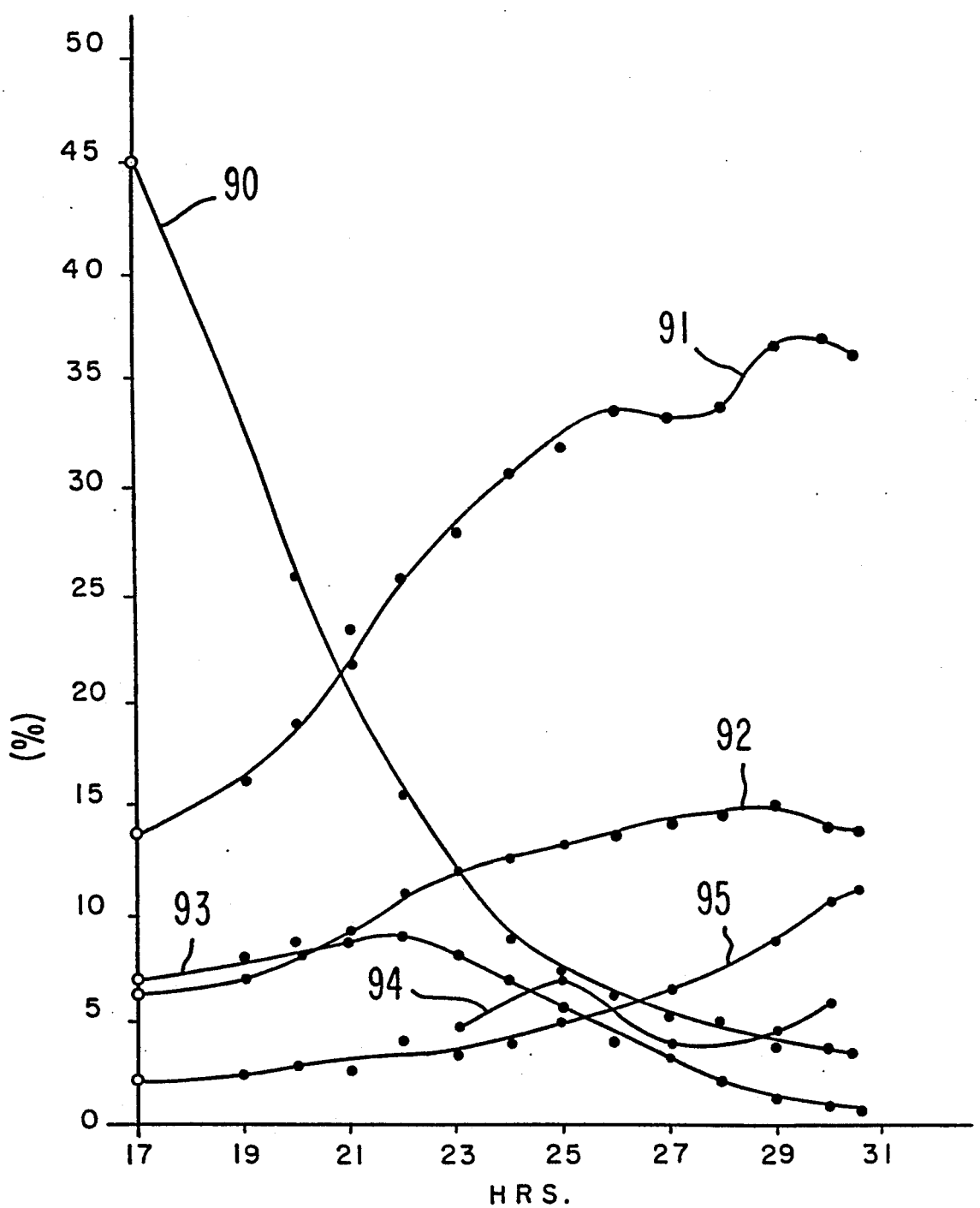

FIG. 9 is a series of graphs showing percent reactant versus time (hours) for the reaction carried out in Example V.

Figure 10:
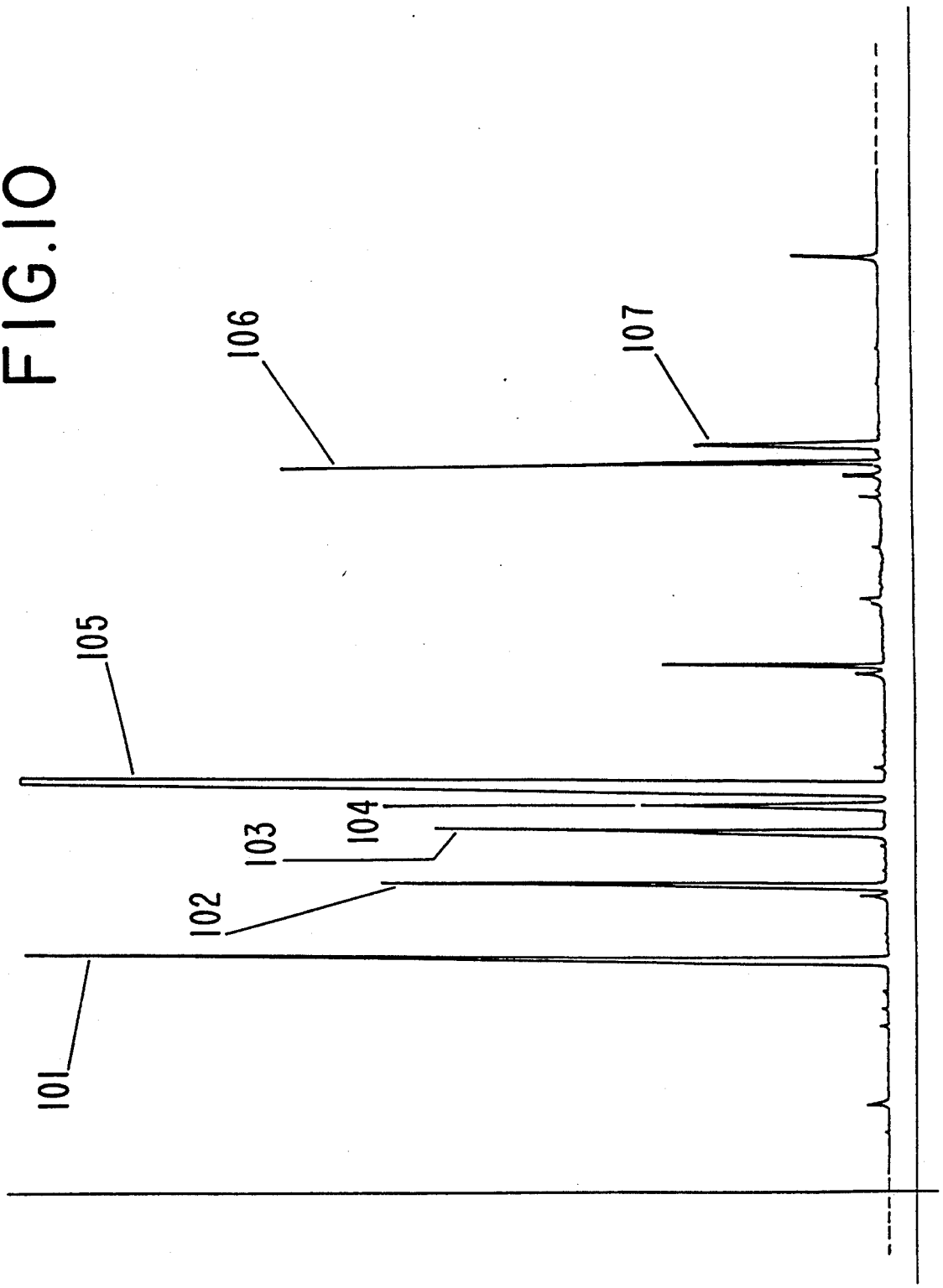

FIG. 10 is the GLC profile for the crude reaction product of Example V containing the compounds having the structures:

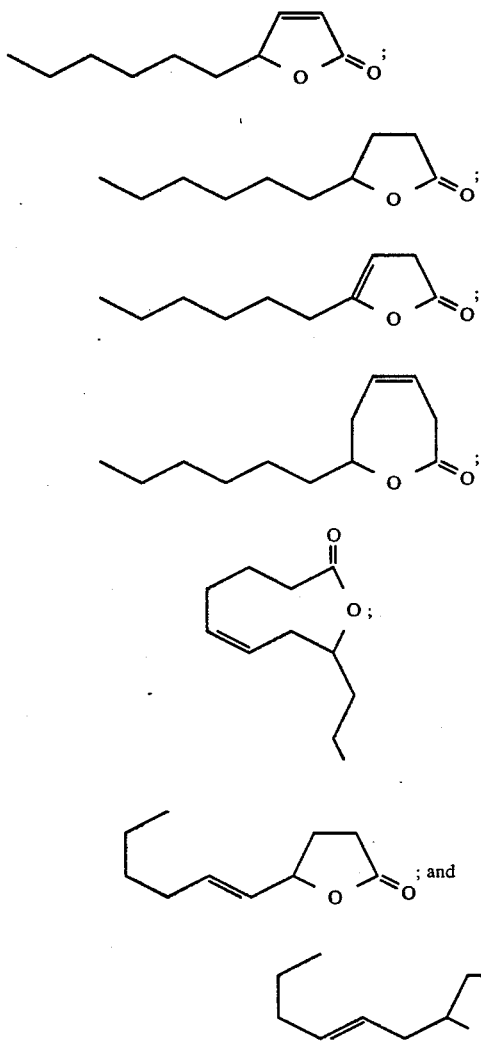

Figure 11:
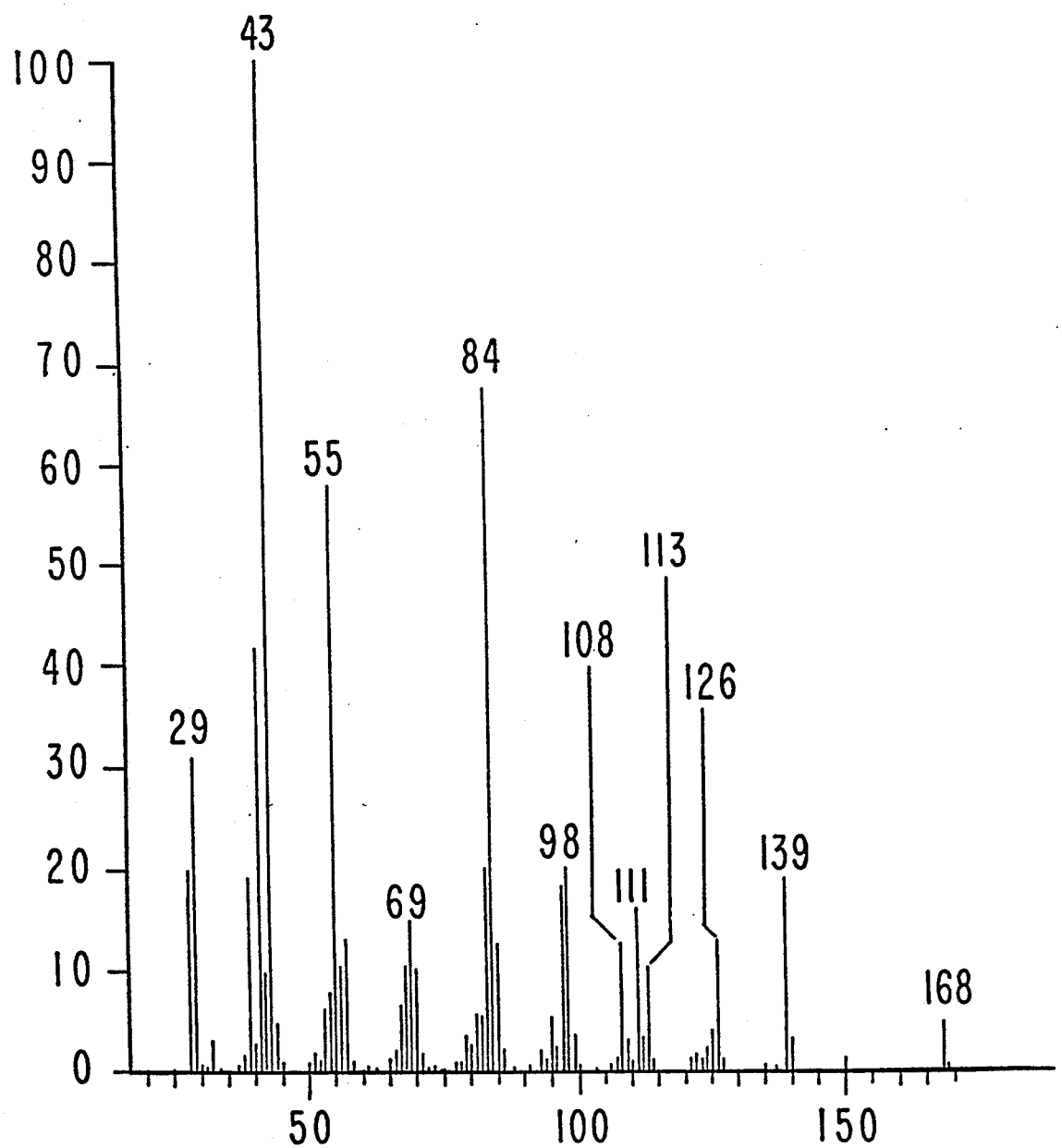

FIG. 11 is the mass spectrum for the compound having the structure:

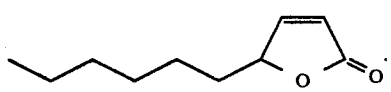

Figure 12:
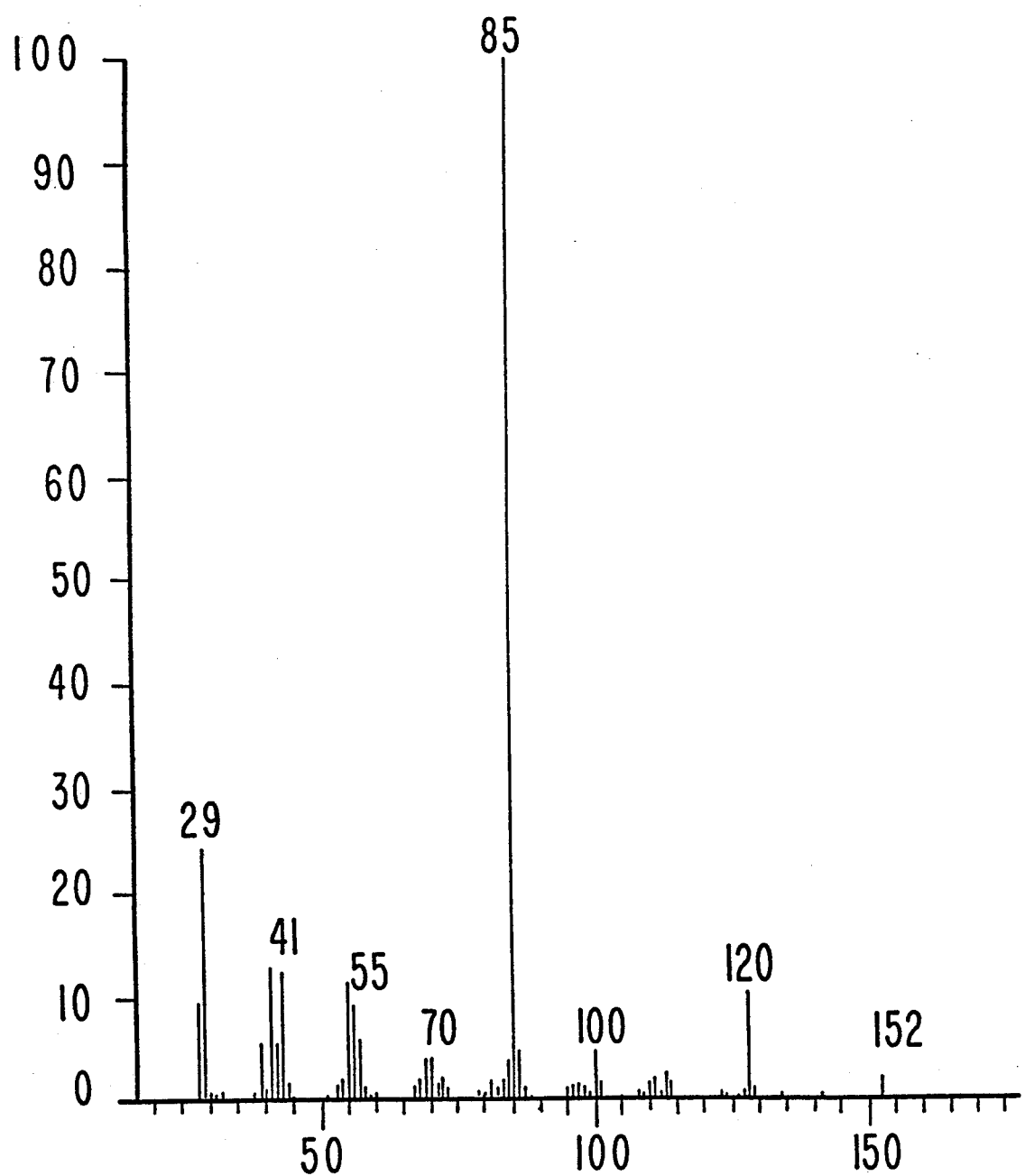

FIG. 12 is the mass spectrum for the compound having the structure:

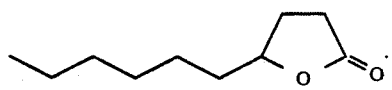

Figure 13:
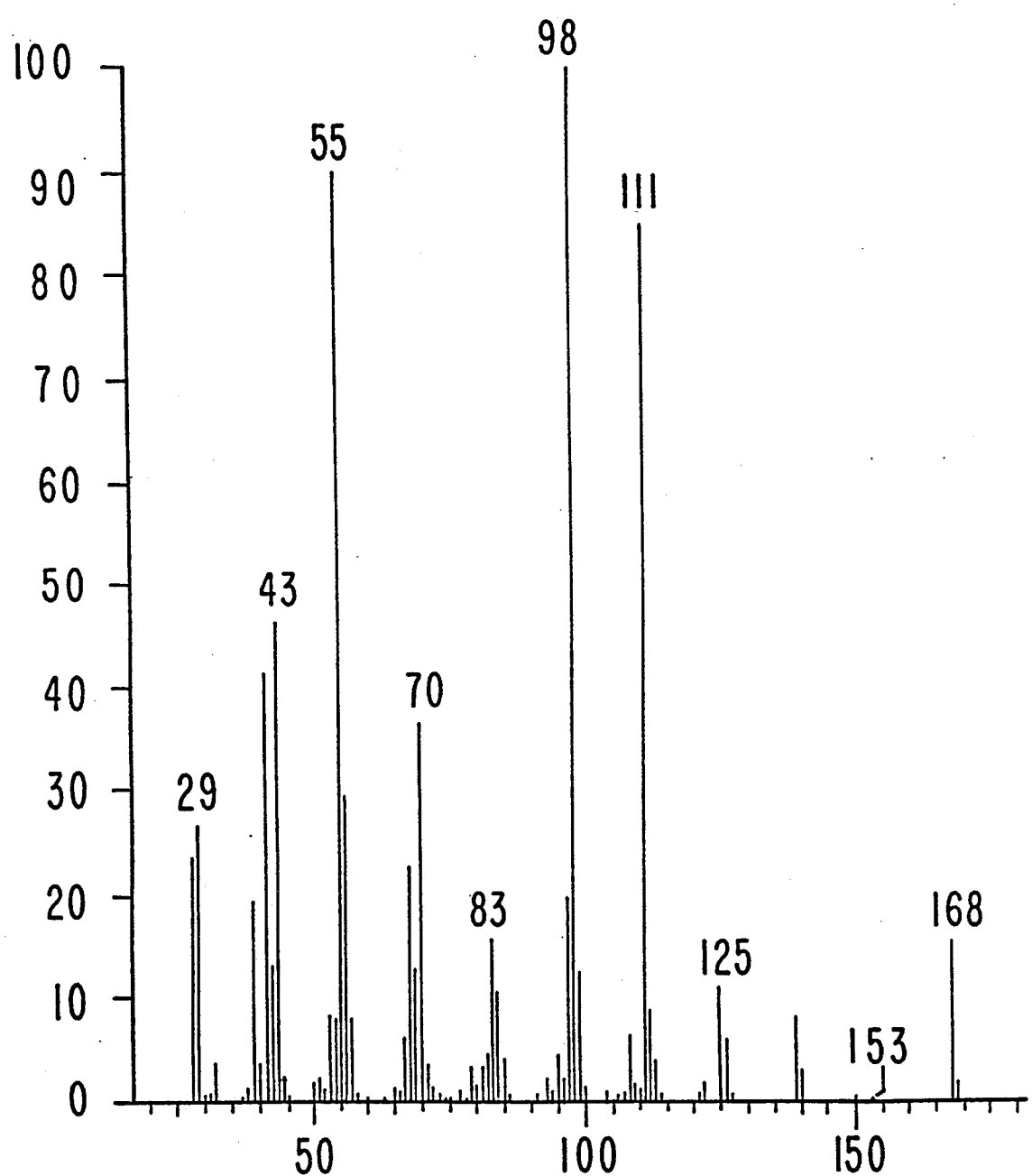

FIG. 13 is the mass spectrum for the compound having the structure:

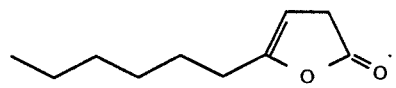

Figure 14:
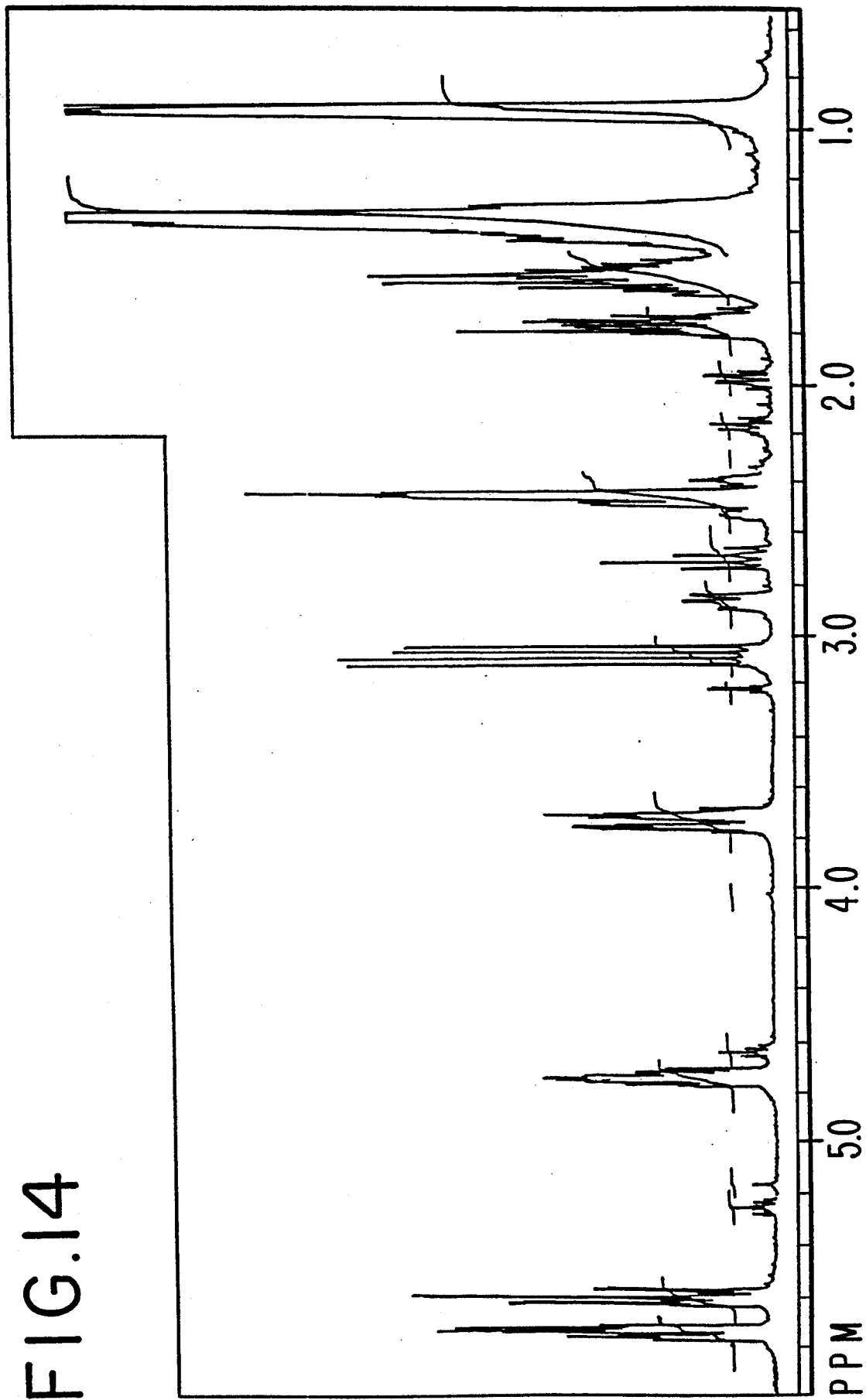

FIG. 14 is the PMR spectrum for the compound having the structure:

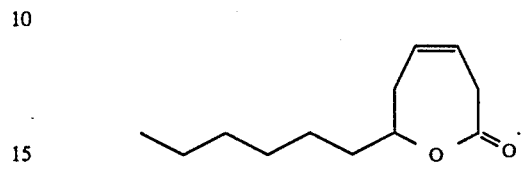

Figure 15:
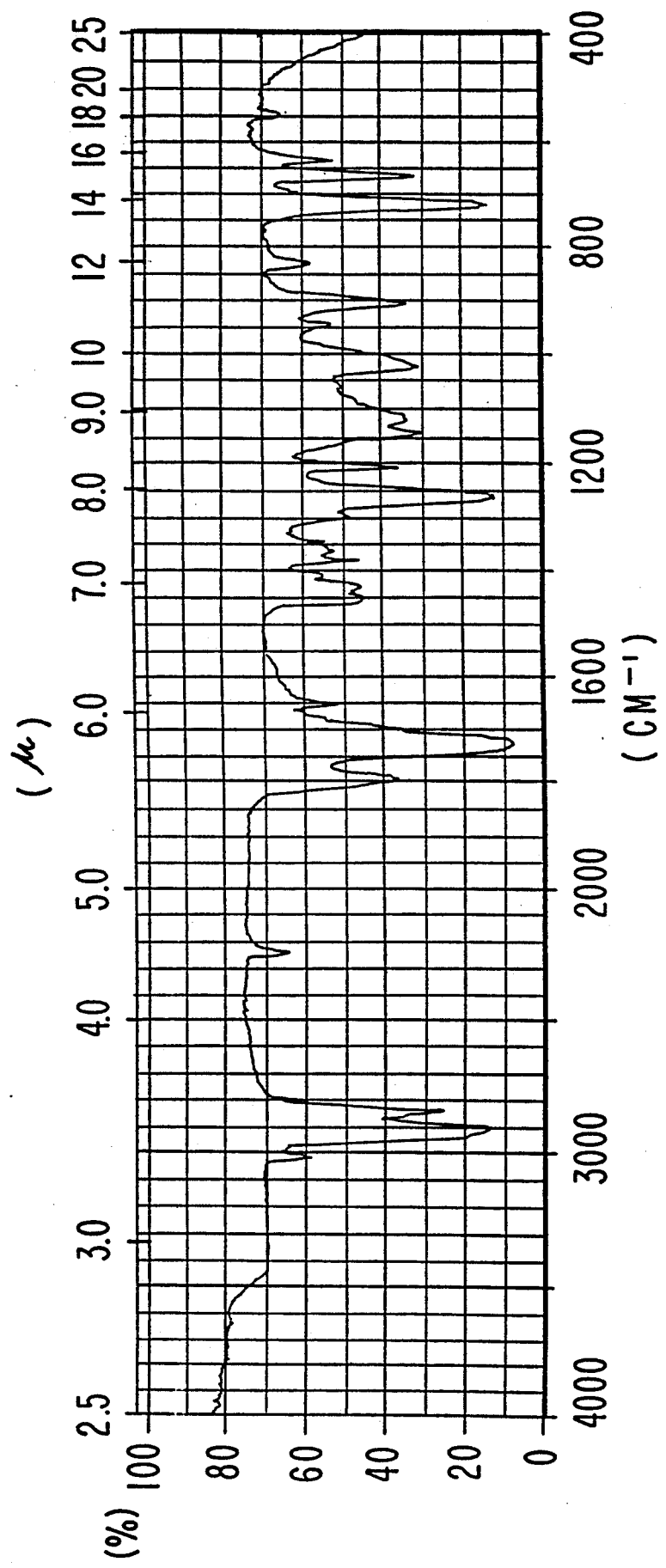

FIG. 15 is the infra red spectrum for the compound having the structure:

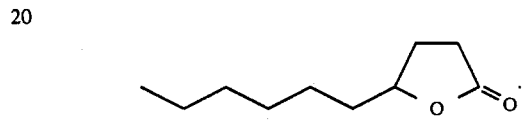

Figure 16:
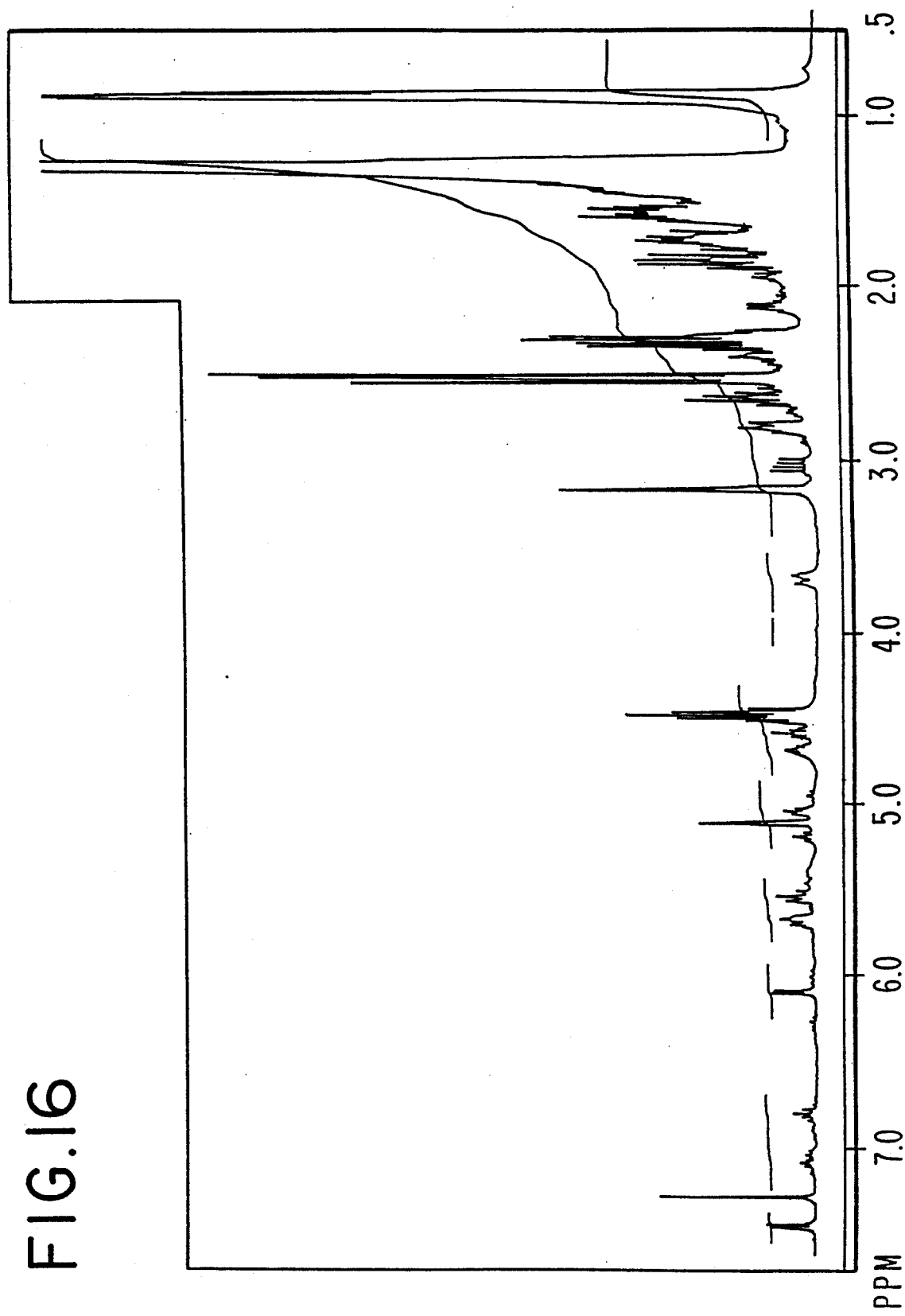

FIG. 16 is the NMR spectrum for Fraction 12 of the distillation of the reaction product of Example V.

Figure 17:
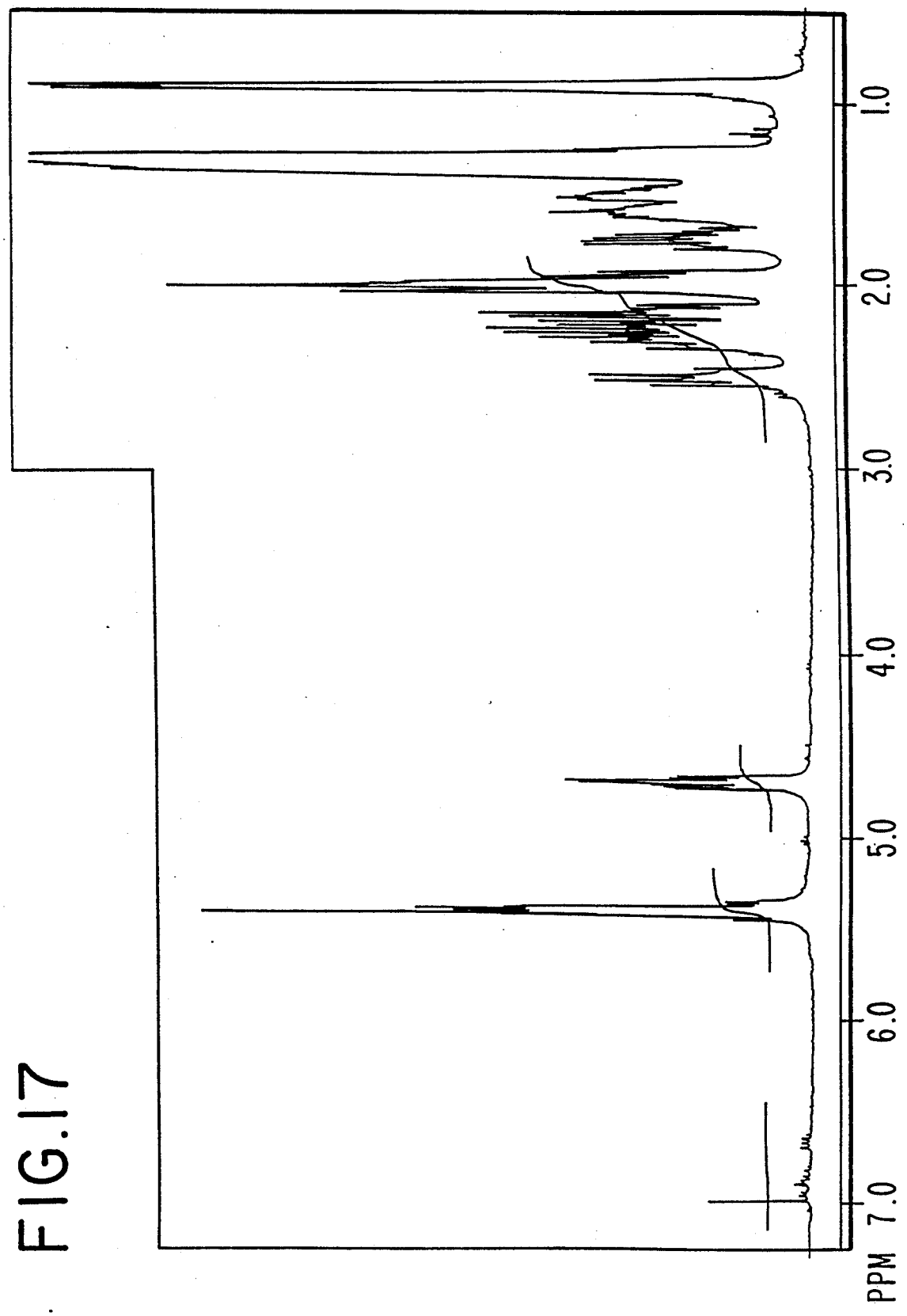

FIG. 17 is the NMR spectrum for the compound having the structure:

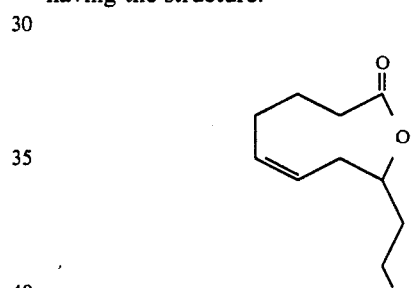

produced according to Example V.

Figure 18:
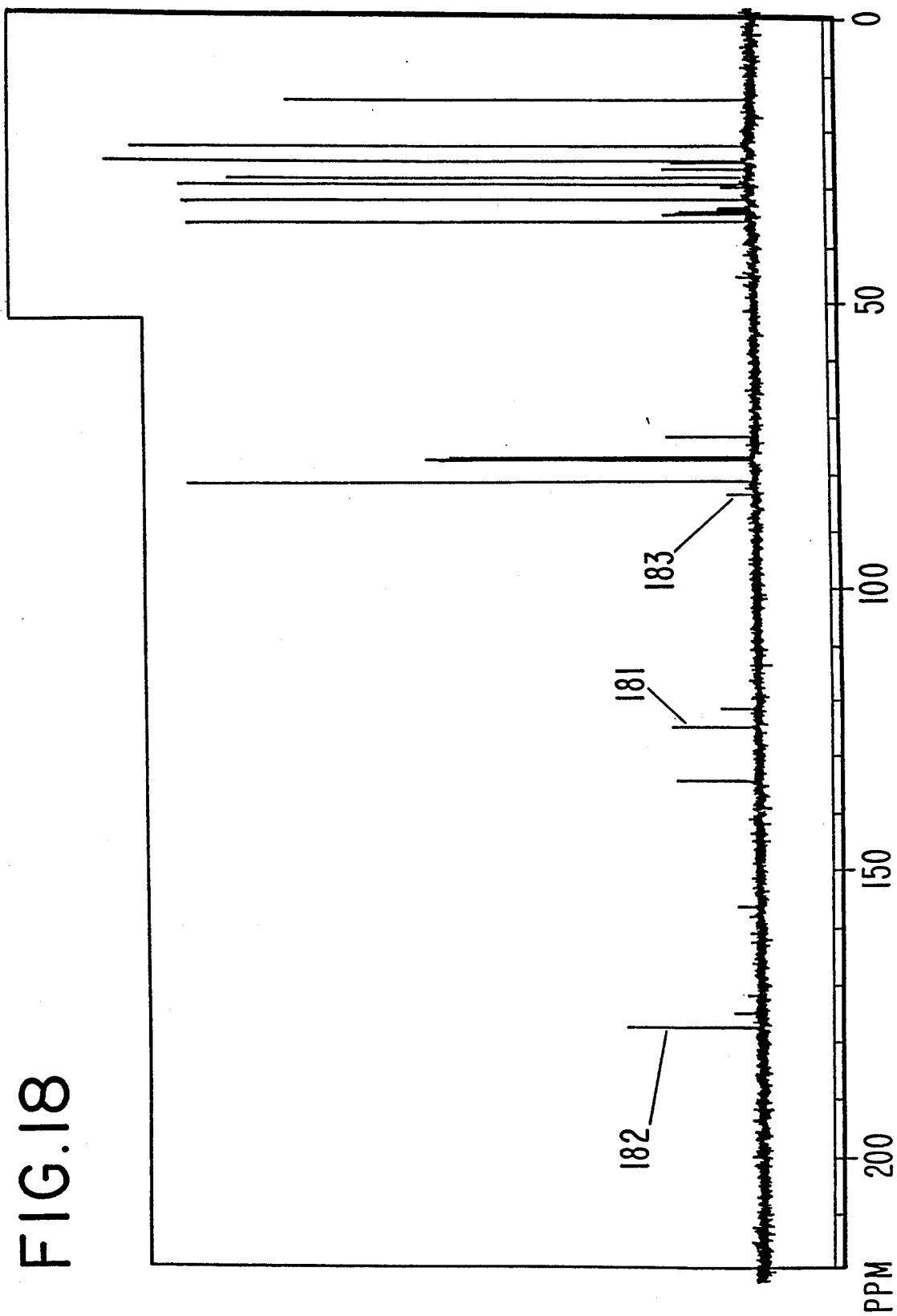

FIG. 18 is the mass spectrum for the mixture of compounds having the structures:

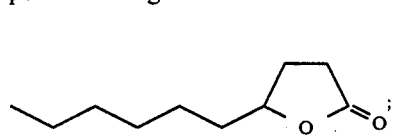

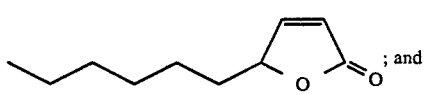

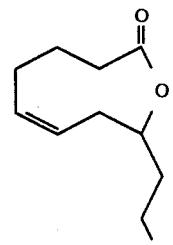

produced according to Example V.

Figure 19:
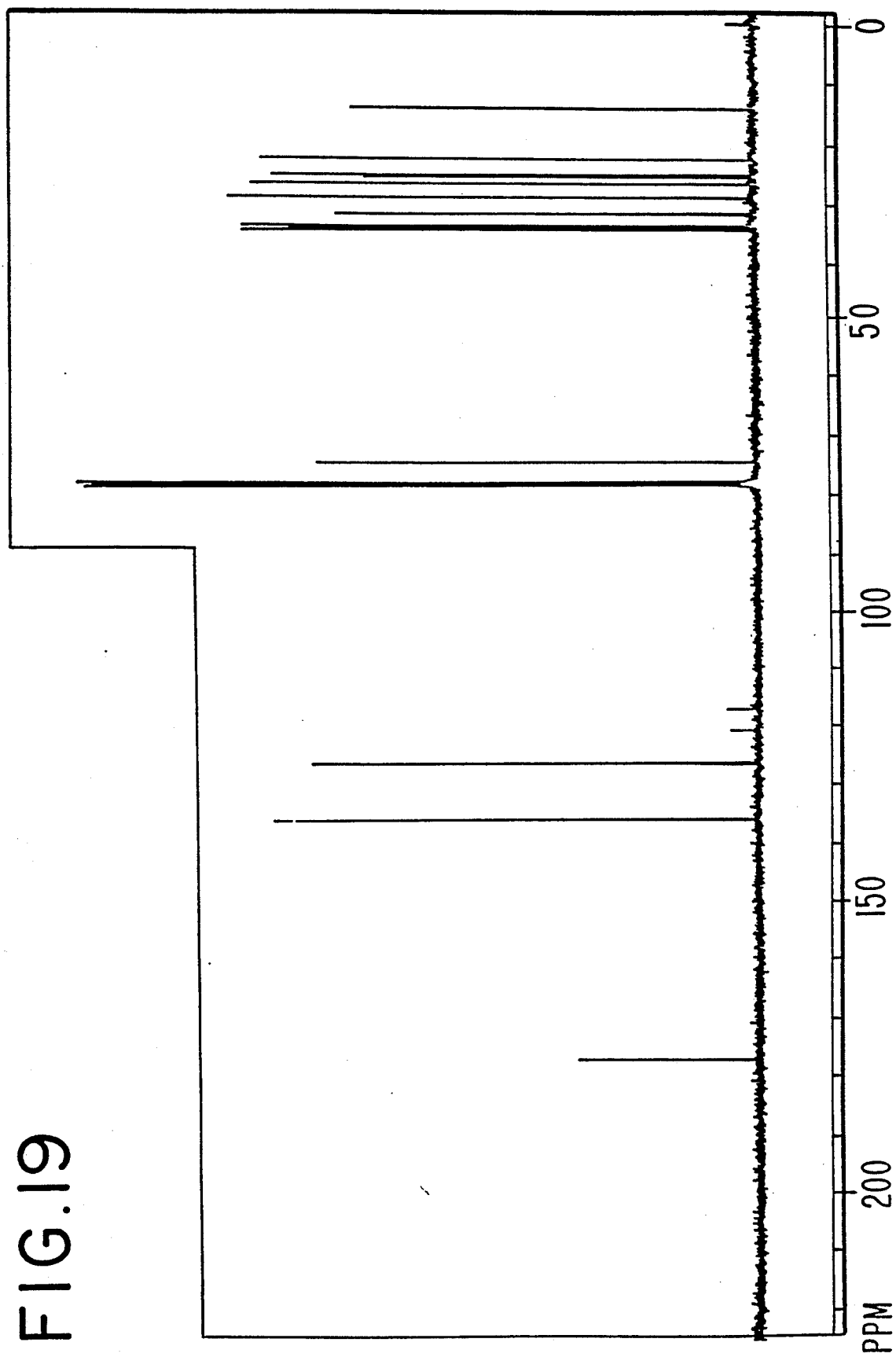

FIG. 19 is the mass spectrum for the compound having the structure:

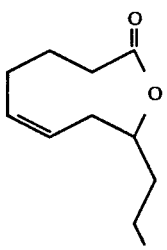

produced according to Example V.

Figure 20:
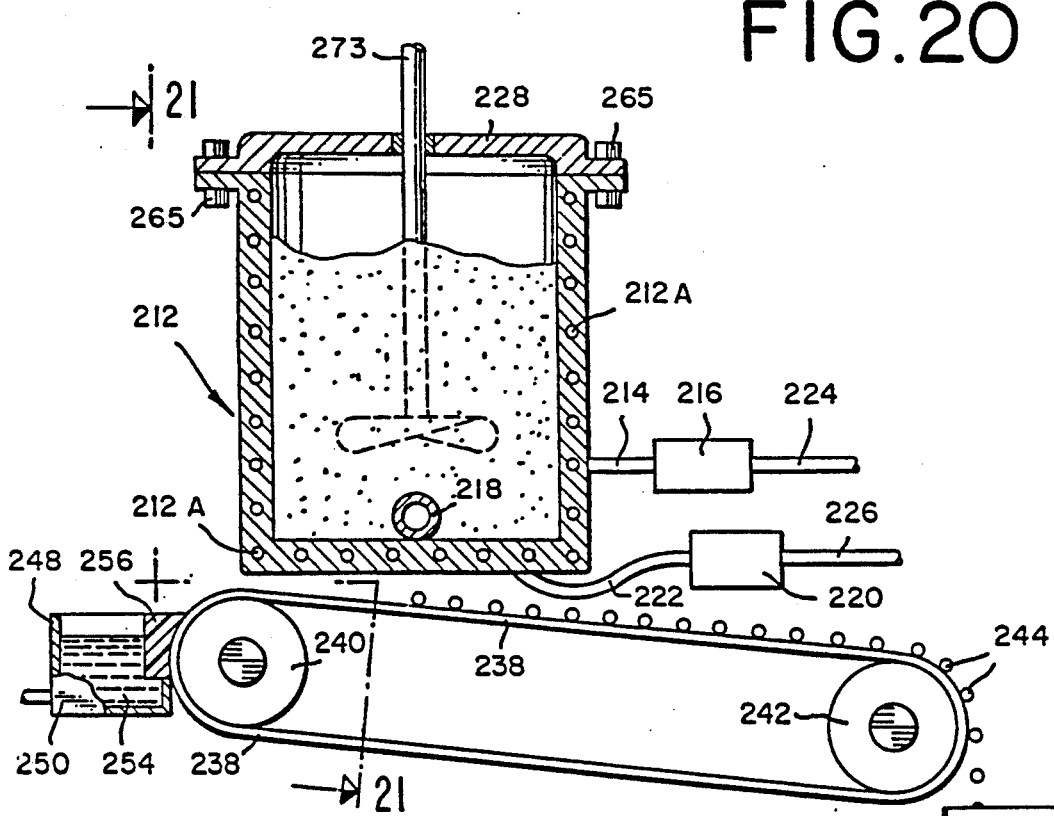

FIG. 20 represents a cut-away side elevation view of apparatus used in forming perfumed polymers which contain imbedded therein at least one of the lactone-containing compositions of our invention.

Figure 21:
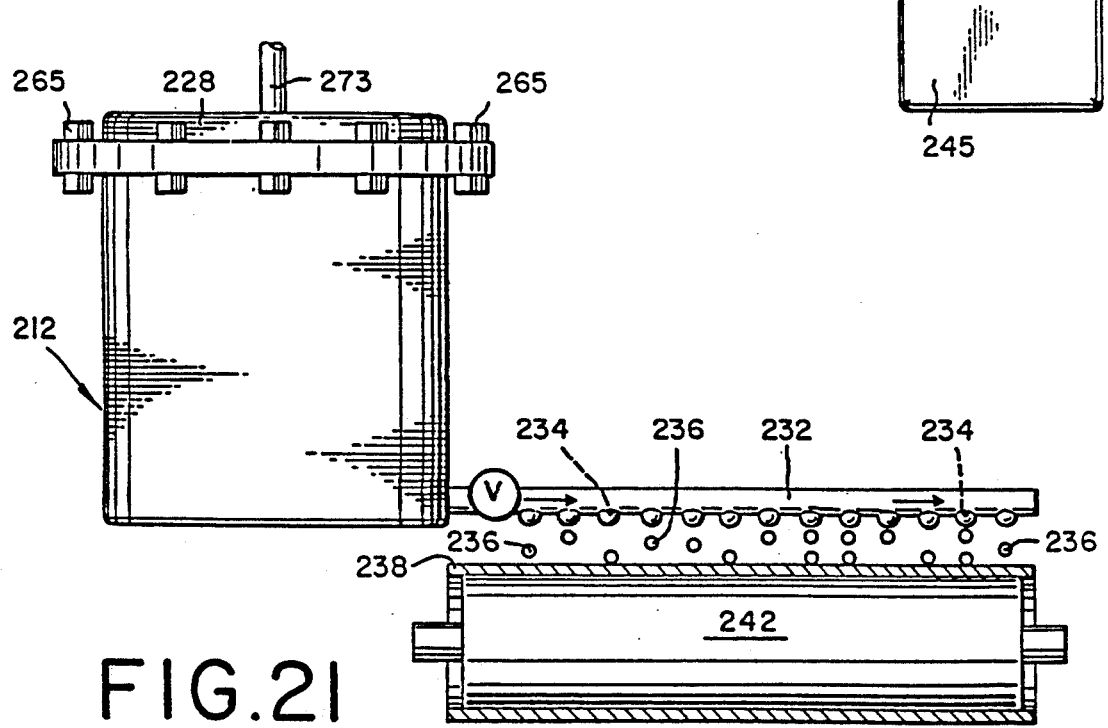

FIG. 21 is a front view of the apparatus of FIG. 20 looking in the direction of the arrows.

DETAILED DESCRIPTION OF THE DRAWINGS

Figure 1:
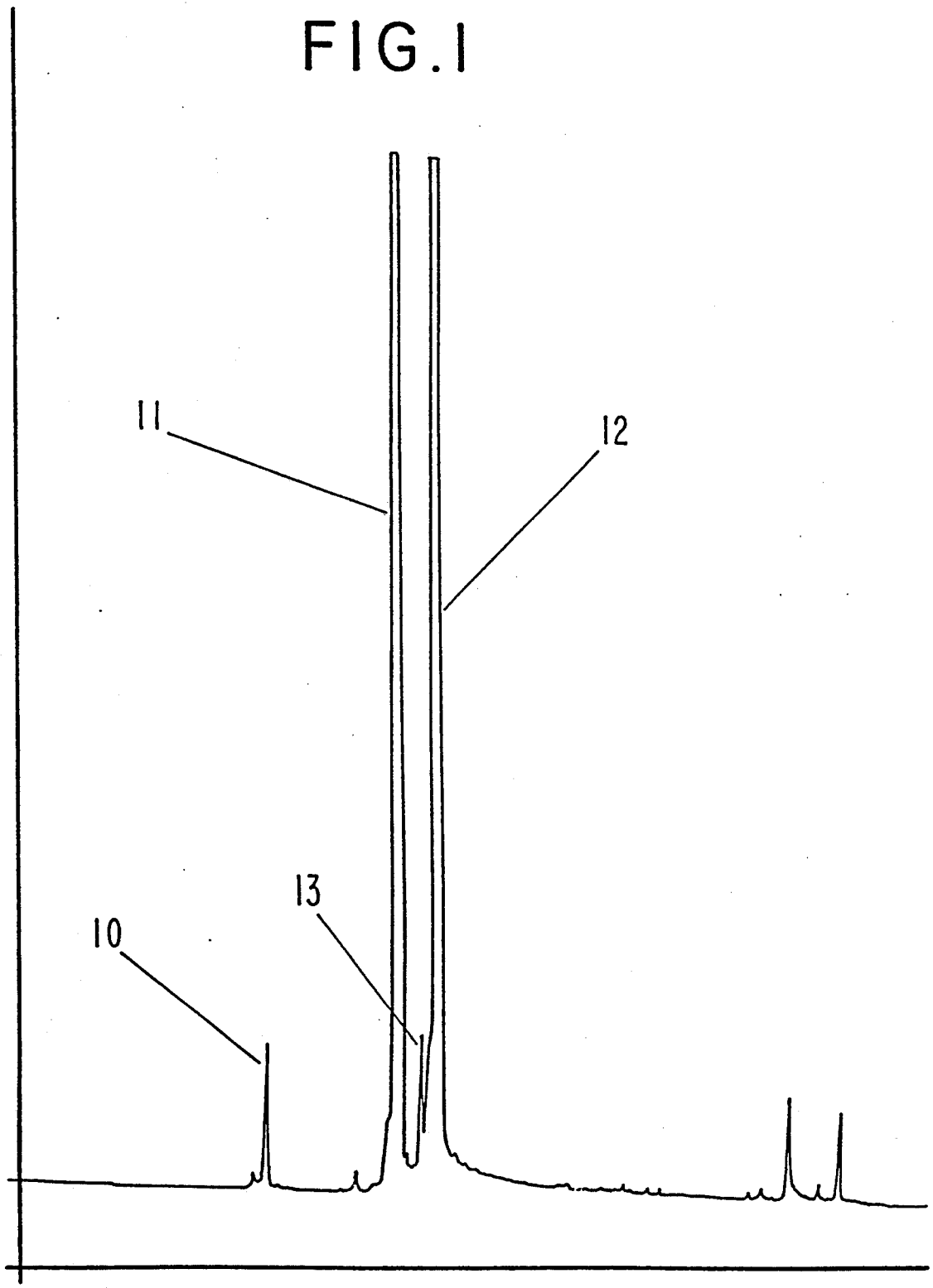
FIG. 1 is the GLC profile for the reaction product of Example I containing the compounds having the structures.

FIG. 1 is the GLC profile for the reaction product of Example I. The peak indicated by reference numeral 10 is the peak for the compound having the structure:

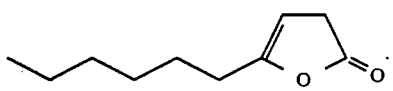

The peak indicated by reference numeral 11 is the peak for the compound having the structure:

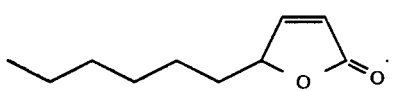

The peak indicated by reference numeral 12 is the peak for the compound having the structure:

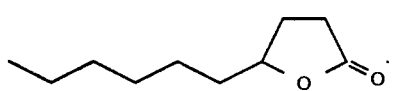

The peak indicated by reference numeral 13 is the peak for the mixture of compounds shown according to the structure:

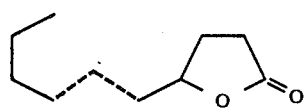

(wherein one of the dashed lines is a carbon-carbon double bond and the other of the dashed lines is a carbon-carbon single bond; or shown as a mixture of the two compounds having the structures:

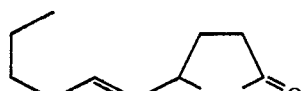

and

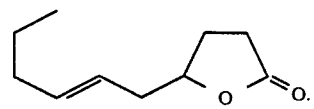

FIG. 2 is the GLC profile of the distilled reaction product of Example I. The peak indicated by reference numeral 20 is the peak for the compound having the structure:

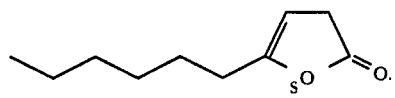

The peak indicated by reference numeral 21 is the peak for the compound having the structure:

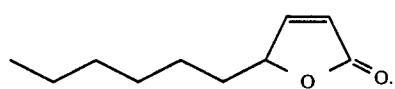

The peak indicated by reference numeral 22 is the peak for the mixture of compounds having the structures:

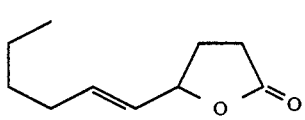

and

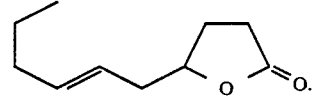

The peak indicated by reference numeral 23 is the peak for the compound having the structure:

The peak indicated by reference numeral 24 is the peak for the compound having the structure:

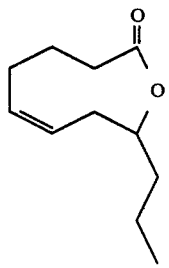

FIG. 3 is the GLC profile for the reaction product of Example II. The peak indicated by reference numeral 30 is the peak for the compound having the structure:

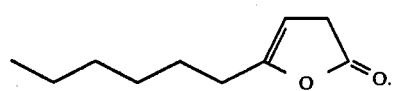

The peak indicated by reference numeral 31 is the peak for the compounds having the structures:

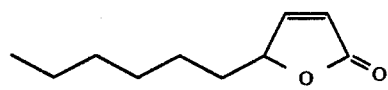

and

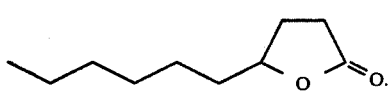

The peak indicated by reference numeral 32 is the peak for the mixture of compounds having the structures:

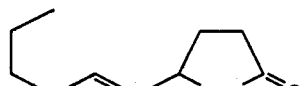

and

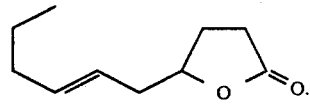

FIG. 8 is the GLC profile for Fraction 1 of the distillation of the reaction product of Example V (Conditions: 50 m×0.32 mm OV-1 fused silica column). The peak indicated by reference numeral 80 is the peak for the compound having the structure:

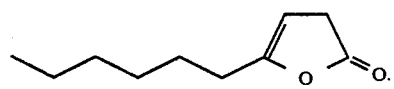

FIG. 9 is a graph showing percent reactant versus time (hours) for Example V. The graph indicated by reference numeral 90 is the graph showing percent ricinoleic acid. The peak indicated by reference numeral 91 is the peak for C₁₂ lactone having the structure:

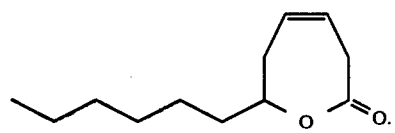

The peak indicated by reference numeral 92 is the peak for gamma decalactone having the structure:

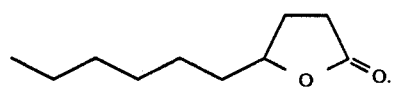

The peak indicated by reference numeral 93 is the peak for C₁₄ lactone having the structure:

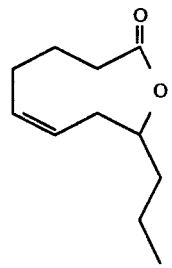

The peak indicated by reference numeral 94 is the peak for gamma decalactone via distillation having the structure:

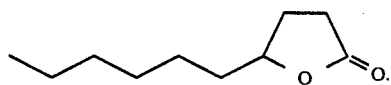

The peak indicated by reference numeral 95 is the peak for another isomer of the compound having the structure:

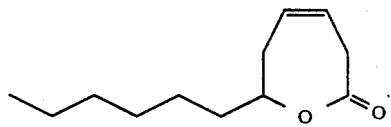

FIG. 10 is the GLC profile for the crude reaction product of Example V. The peak indicated by reference numeral 101 is the peak for the compound having the structure:

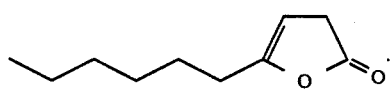

The peak indicated by reference numeral 102 and the peak indicated by reference numeral 104 are peaks for the compounds having the structures:

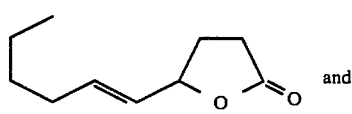

and

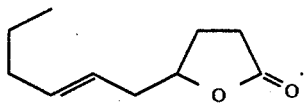

The peak indicated by reference numeral 103 is the peak for the compound having the structure:

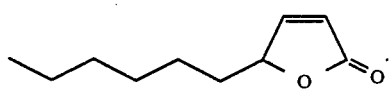

The peak indicated by reference numeral 105 is the peak for the compound having the structure:

The peak indicated by reference numeral 106 is the peak for the compound having the structure:

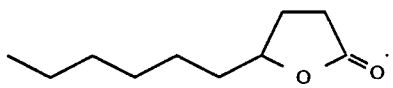

The peak indicated by reference numeral 107 is the peak for the compound having the structure:

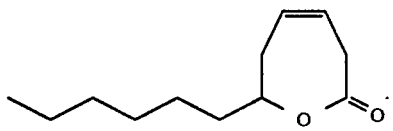

FIG. 18 is the mass spectrum for the mixture of compounds having the structures:

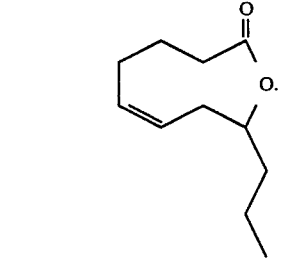

The peak indicated by reference numeral 182 is the peak for the compound having the structure:

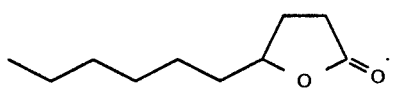

The peak indicated by reference numeral 181 is a peak for the compound having the structure:

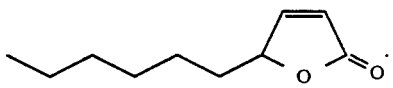

The peak indicated by reference numeral 183 is a peak for the compound having the structure:

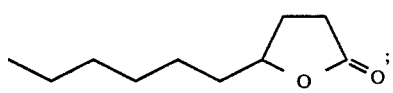

Referring to FIGS. 20 and 21, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 20 and 21, in particular, the apparatus used in producing such elements comprises a device for forming the polymer containing perfume, e.g., polyethylene or polyethylene-polyvinyl acetate or mixtures of same or polyproyplene, which comprises a vat or container 212 into which the polymer taken alone or in admixture with other copolymers and the perfuming substance which is at least one of the lactones of our invention or mixtures of lactones and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostate or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the lactones of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the lactones of our invention or mixture of perfume substance and one or more of the lactones of our invention, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all or which contains one or more of the lactones of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

SUMMARY OF THE INVENTION

Our invention relates to a method using fermentation techniques to produce and recover certain naturally occurring lactones found to be useful for their organoleptic properties in augmenting or enhancing the aroma or taste of consumable materials such as foodstuffs, chewing gums, toothpastes, medicinal products, chewing tobaccos, smoking tobaccos, perfume compositions, colognes and perfumed articles, e.g., solid or liquid anionic, cationic, nonionic or zwitterionic detergents, perfumed polymers, fabric softener compositions, fabric softener articles, cosmetic powders, hair preparations and the like which lactones are defined according to the structures:

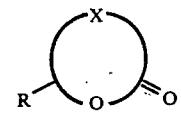

and taken alone or taken further together with the lactone having the structure:

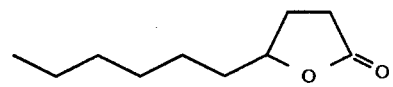

wherein R represents $C_6$ alkyl or alkenyl; and X represents alkylene or alkenylene with the provisos that R is $C_6$ alkyl when X is alkenylene and R is $C_6$ alkenyl when X is alkenylene. The lactone compositions are produced by means of fermentation of castor oil or ricinoleic acid or a castor oil hydrolysate to form a mixture of carboxylic acids having the structure:

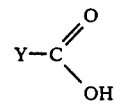

together with gamma hydroxydecanoic acid according to the reaction:

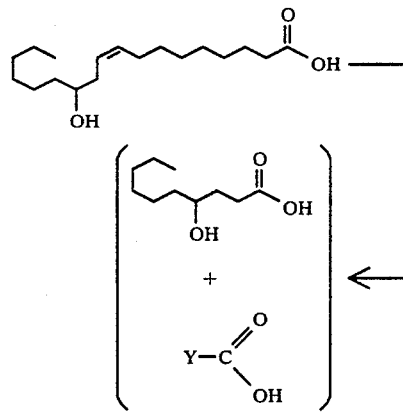

with the reaction of the castor oil going to the ricinoleic acid being shown, thusly:

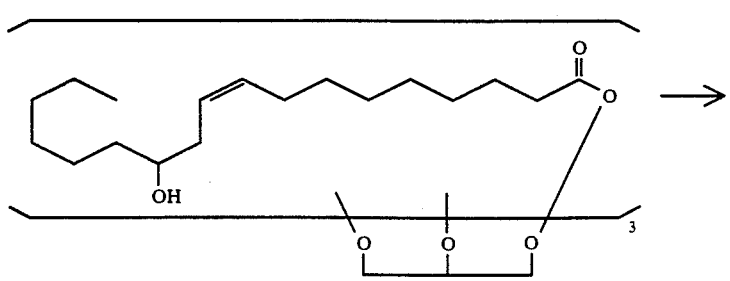

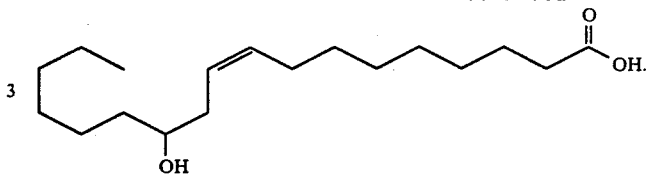

More specifically, the fermentation reaction of the ricinoleic acid going to the various carboxylic acids is shown according to the reaction:

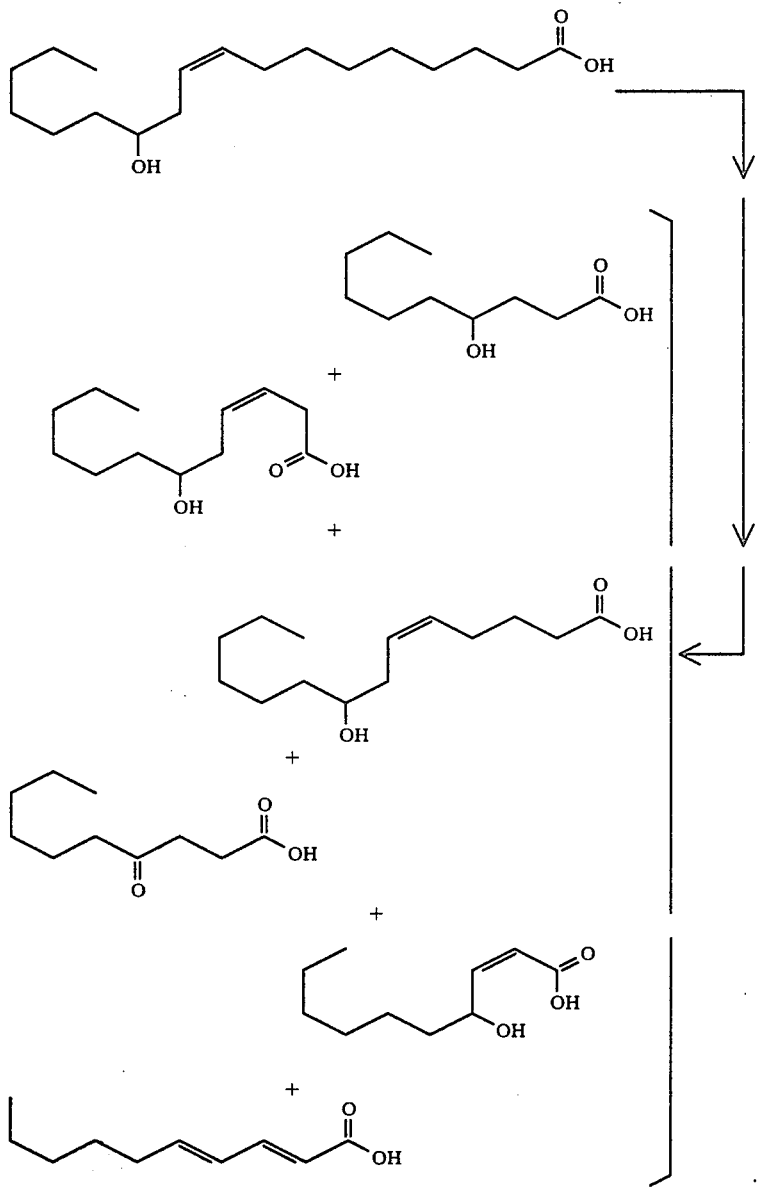

The fermentation reaction is effected as a result of the presence in the reaction mass of certain organisms, to wit, one of:

Candida petrophilum, ATCC 20226;
Candida oleophila, ATCC 20177;
Candida sp., ATCC 20504; or
Candida sake, ATCC 28137.

The resulting reaction mass is then subjected to a pH reduction to a pH in the range of 0–5 and heated at a temperature in the range of about 90° up to about 120° C. whereupon lactonization of the gamma hydroxydecanoic acid takes place, thusly:

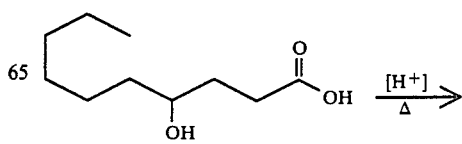

The first step of the process of our invention involving the reactions:

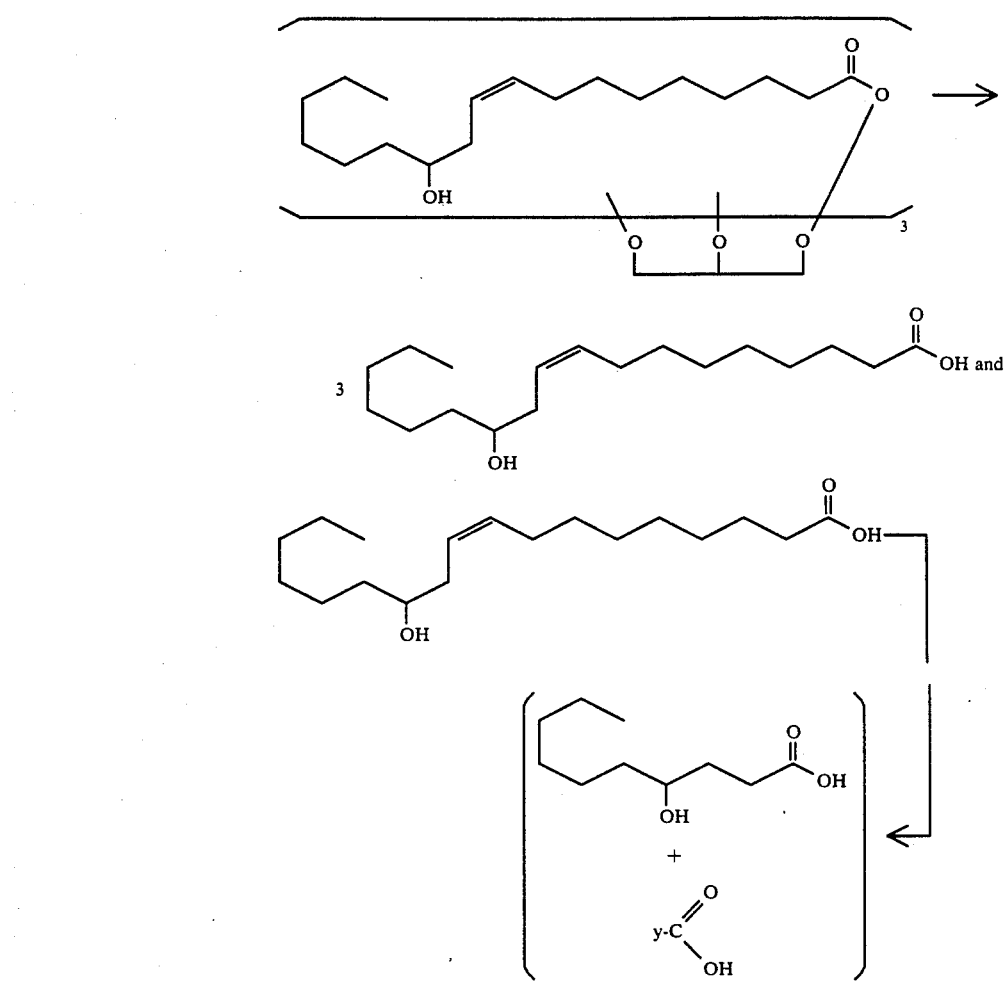

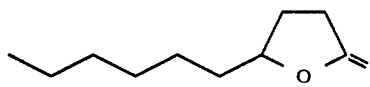

The other acids in the reaction mass do not lactonize.

The third step of the process of our invention involves distillation of the reaction mass at a temperature in the range of 120°–220° C. and at a pH of between about 1 and about 7 whereby the unsaturated acids lactonize according to the reaction:

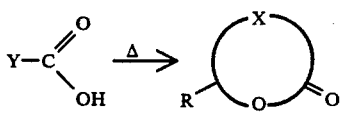

wherein the sum of the carbon atoms in the X moiety and in the R moiety is equal to the number of carbon atoms in the Y moiety minus 1 and wherein Y represents an oxo-saturated, oxo-unsaturated or di-unsaturated $C_9$, $C_{11}$ or $C_{13}$ moiety.

The resulting products, in the form of mixtures of lactones or as separate lactones or groups of lactones are useful in augmenting or enhancing the aroma or taste of consumable materials as set forth, supra.

takes place at a pH in the range of 5.5 up to 7 and a temperature in the range of from about 20° up to about 35° C.

Prior to the reaction taking place an inoculum is produced whereby the microorganism, e.g., Candida petrophilum, ATCC 20226 is grown in olive oil for a period of about 10 up to about 30 hours. The resulting inoculum is then admixed with castor oil or a castor oil hydrolysate substrate.

The form in which the microorganisms are used is not critical. They can be used as the culture (suspension), i.e., including the cells and the corresponding nutrient solution, or in the form of cells suspended in a buffer solution. The cells or an enzyme extract thereof may be immobilized on a suitable solid support which may then be used to effect the transformations.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinoise, L-rhamnose, ethanol, glycerol, L-erythritol, D-mannitol, lactose, melibiose, raffinose, meleitose, starch, D-xylose, D-sorbitol, alpha-methyl-D-glucoside, lactic acid, citric acid and succinic acid. Among the suitable nitrogen sources are, for example, nitrogen-containing organic substances such as peptone, meat extract, yeast extract, corn steep liquor, and casein, urea, amino acids, or nitrogen containing inorganic compounds such as nitrates, nitrites, and inorganic ammonium salts. Among the suitable inorganic salts are, for example, phosphates, magnesium, potassium, calcium, sodium. The above mentioned nutrients in the culture medium may be supplemented with, for example, one or more vitamins of the B Group and/or one or more trace minerals such as Fe, Mo, Cu, Mn, B as desired. However, the process can be performed in a vitamin-free medium; for example, when a small amount of yeast extract is added to the medium there is no need for vitamins or trace minerals.

The cultivation of the microorganism can be carried out as a stationary culture or as a submerged culture (e.g., shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as sodium hydroxide, potassium hydroxide, calcium hydroxide, calcium carbonate, by ion-exchange resins, or by the addition of a buffer such as phosphate or phthalate. The incubation temperature is suitably maintained at between about 15° C. and about 33° C., with a range from about 20° C. to about 30° C. being preferred.

The process in accordance with the invention is conveniently carried out by adding castor oil or castor oil hydrolysate, as the substrate, to the culture medium at the onset of cultivation, as the sole carbon source. Alternatively, the substrate may be added in combination with another carbon source, such as dextrose, either during cultivation, or when cultivation is complete. The amount level, or concentration of the substrate in the medium may vary. For example, in the case of hydrolyzed castor oil, levels of from about 0.3% to about 5% may make up the medium initially or be added during the course of the fermentation, whereas substantially any level of castor oil may be used.

The reaction time may vary depending on the composition of the culture medium and the substrate concentration. In general, shaking flask cultures require from between about 2 h. and about 240 h. depending upon the microorganism and the composition of the culture medium. However, when a fermentor is used the fermentation time may be reduced to about 100 h. or less.

The fermentation may be carried out using the cells of the microorganism isolated from the culture solution, or with an enzyme extract isolated from the cells in a manner known per se. In this case, the fermentation can be conveniently carried out in aqueous solution, for example, in a buffer solution, in a physiological salt solution, in a fresh nutrient solution, or in water. The isolated cells or enzyme extract may be immobilized on a solid support and the desired transformation effected in the absence of the live microorganism. The transformation of the substrate may be effected by mutants of the microorganism. Such mutants can be obtained readily by methods well known in the art, for example, by exposing the cells to UV or X-rays, or customary mutagenic substances such as, for example, acridine orange.

The substrate is generally added directly to the medium. A surface-active agent or dispersion agent, such as TWEEN® 80 polyoxyethylenesorbitan monostearate), can also be added to an aqueous suspension of the substrate. Conventional antifoam agents, such as silicone oils (e.g., UCON), polyalkyleneglycol derivatives, maize oil, or soya oil can be used to control foaming.

The transformation of the substrate can be monitored using standard analytical techniques such as GLC, TLC, HPLC, IR and NMR. If a rapid disappearance of the substrate is observed, more substrate can then be added in order to maximize the transformation capacity of the microorganisms. The incubation is generally terminated when all the substrate has disappeared from the culture medium.

After the fermentation process is complete, the lactonization steps may take place. The first lactonization, involving the reaction of gamma hydroxydecanoic acid, to wit:

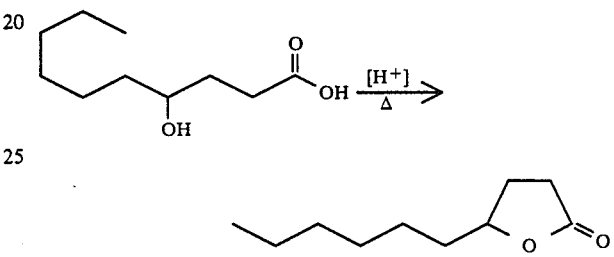

takes place at a pH in the range of 0–5 at a temperature of 90°–120° C. The pH is adjusted using acids such as 85% aqueous phosphoric acid. The reaction time may vary from about 0.25 hours up to about 2 hours. During this first lactonization step the unsaturated carboxylic acids defined according to the structure:

e.g., the carboxylic acids having the structures:

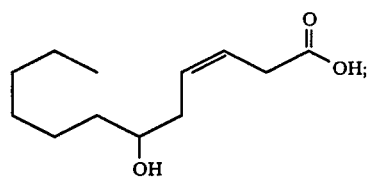

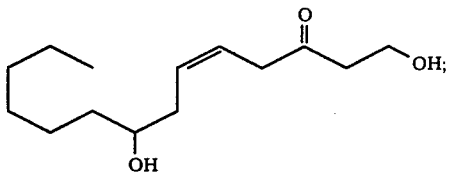

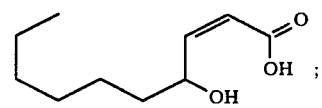

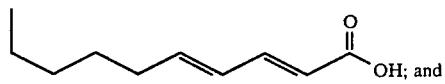

-continued

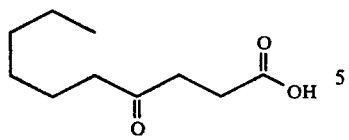

do not lactonize.

However, when the resulting mixture containing the gamma decalactone having the structure:

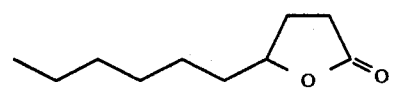

is distilled at 120°–220° C. while the pH of the reaction mixture is in the range of 1–7 lactones having the structures:

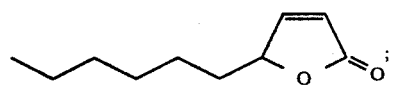

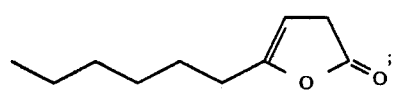

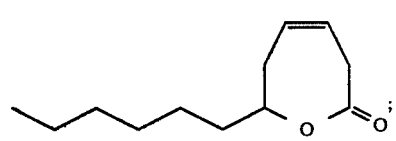

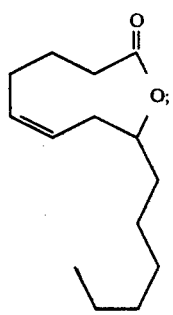

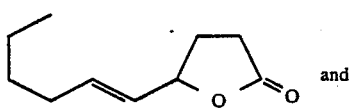

and

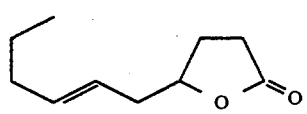

are produced according to the reactions:

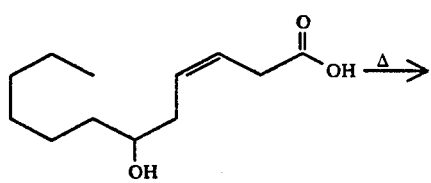

-continued

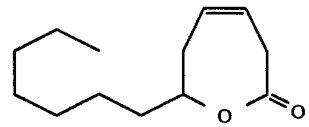

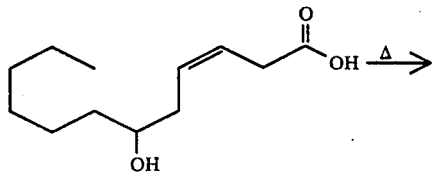

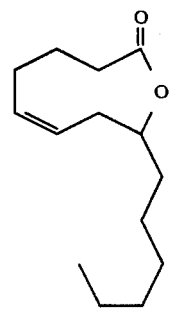

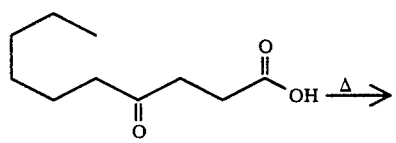

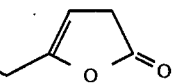

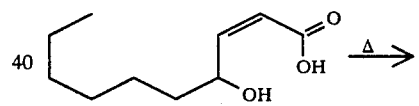

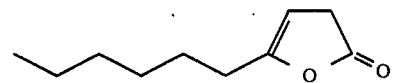

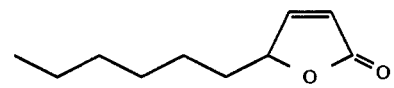

and

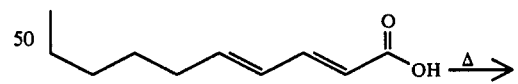

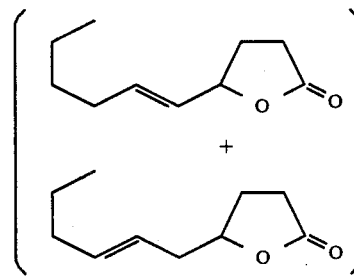

The lactone derivative(s) and one or more auxiliary perfume ingredients, including, for example, hydrocarbons, alcohols, ketones, aldehydes, nitriles, esters other than the lactone derivatives of our invention, ethers, synthetic essential oils, and natural essential oils may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, one or more of the lactone derivative(s) of our invention can be used to alter, modify or enhance the aroma characteristics of a perfume composition, for example, by utilizing or moderating the olfactory reaction contributed by another ingredient in the composition.

The amount of lactone derivative(s) of our invention which will be effective in perfume compositions as well as in perfumed articles and colognes depends upon many factors including the other ingredients, their amounts and the effects which are desired. It has been found that perfume compositions containing as little as 0.005% of lactone derivative(s) or even less (e.g., 0.002%) can be used to impart sweet, fruity (peach and apricot) aromas to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The lactone derivative(s) of our invention are useful (taken alone or taken together with other ingredients in perfume compositions) in detergents, soaps, space odorants and deodorants, perfumes, colognes, toilet waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the lactone derivative(s) will suffice to impart an intense, sweet, fruity (peach and apricot) aroma to floral perfume formulations. Generally no more than 5% of the lactone derivative(s) based on the ultimate end product is required to be used in the perfume compositions.

Furthermore, as little as 0.25% of the lactone derivative(s) will suffice to impart such aromas to perfumed articles per se, whether in the presence of other perfume materials or whether used by themselves. Thus, the range of use of the lactone derivative(s) of our invention in perfumed articles, e.g., perfumed polymers and solid or liquid anionic, cationic, nonionic or zwitterionic solid or liquid detergents, may vary from 0.25% up to about 5% by weight based on the total weight of the perfumed article.

In addition, the perfume composition or fragrance composition of our invention can contain a vehicle or carrier for the lactone derivative(s). The vehicle can be a liquid such as a non-toxic alcohol, e.g., ethanol, a non-toxic glycol, e.g., propylene glycol, or the like. The carrier can also be an absorbent solid such as a gum (e.g., gum arabic or xanthan gum or guar gum) or components for encapsulating the composition by means of coacervation (such as by gelatin) or by means of formation of a polymer around a liquid center (as by using a urea formaldehyde prepolymer to form a polymeric capsule around a perfume composition center).

It will be appreciated from the present disclosure that the lactone derivatives according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify its organoleptic character.

The term "enhance" is intended herein to mean the intensification (by use of the lactone derivative of our invention) of a flavor or aroma note or nuance in a tobacco flavor or foodstuff or perfume composition or perfumed article without changing the quality of said note or nuance.

A "flavoring composition" is taken to mean one which contributes a part of the overall flavor impression by supplementing or fortifying a natural or artifical flavor in a material or one which supplies substantially all the flavor and/or aroma character to a consumable article.

The term "foodstuff" as used herein includes both solid and liquid ingestible materials for man or animals which materials usually do, but need not, have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat foods, other veterinary products, and the like. The lactone derivative(s) of our invention are also useful tobacco flavorants and flavor enhancers.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like as well as tobacco substitutes intended to replace natural tobacco such as lettuce and cabbage leaves and the like. The tobaccos and tobacco products in which the lactone derivative(s) of our invention are useful include those designed or used for smoking such as in cigarettes, cigar and pipe tobacco, as well as products such as snuff, chewing tobacco and the like.

When the lactone derivative(s) of this invention are used in a flavoring composition, they can be combined with conventional flavoring materials or adjuvants. Such co-ingredients or flavoring adjuvants are well known in the art for such and have been extensively described in the literature. Requirements of such adjuvant materials are: (1) that they be non-reactive with the lactone derivative(s) of our invention; (2) that they be organoleptically compatible with the lactone derivative(s) of our invention whereby the flavor of the ultimate consumable material to which the lactone derivative(s) are added is not detrimentally affected by the use of the adjuvant; (3) that they be ingestibly acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols including primary and secondary alcohols, esters, carbonyl compounds including ketones and aldehydes; lactones; other cyclic organic materials including benzene derivatives, allicyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil and the like and artificial flavoring materials such as vanillin and the like.

Specific preferred flavor adjuvants are as follows:
anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil;
3,4-dimethoxyphenol;
amyl acetate;
amyl cinnamate;
gamma butyryl lactone;
furfural;
trimethyl pyrazine;
phenyl acetic acid;
isovaleraldehyde;
ethyl maltol;
ethyl vanillin;
ethyl valerate;
ethyl butyrate;
cocoa extract;
coffee extract;
peppermint oil;
spearmint oil;
clove oil;
anethol;
cardamom oil;
wintergreen oil;
cinnamic aldehyde;
ethyl-2-methyl valerate;
gamma hexenyl lactone;
2,4-decadienal;
2,4-haptadienal; and
butylidene phthalide.

According to another aspect of our invention, an organoleptically improved smoking tobacco product and additives therefor as well as methods of making the same which overcome specific problems heretofore encountered in which specific Turkish, oriental-like aromas prior to smoking and improved Turkish, oriental aromas on smoking in the main stream and the side stream are created or enhanced or modified or augmented and may be readily controlled and maintained at the desired uniform level regardless of variations in the tobacco components of the blend. In particular, low grade Virginia-type tobaccos may be upgraded using the lactone derivative(s) of our invention.

This invention further provides improved tobacco additives and methods whereby various desirable natural aromatic Turkish tobacco flavoring characteristics with oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more of the lactone derivative(s) of our invention.

In addition to the lactone derivative(s) of our invention, other flavoring and aroma additives may be added to the smoking tobacco material or substitute therefor either separately or in admixture with the lactone derivative(s) of our invention as follows:

I. Synthetic materials:
Beta-ethyl-cinnamaldehyde;
Eugenol;
Dipentene;
Beta-damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-1,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a-6,6,9a-tetramethyl naphtho(2,1-b)furan;
4-Hydroxy hexanoic acid, gamma lactone; and
Polyisoprenoid hydrocarbons defined in Example V of U.S. Pat. No. 3,589,372 issued on June 29, 1971.

II. Natural oils:
Celery seed oil;
Coffee extract;
Bergamot oil;
Cocoa extract;
Nutmeg oil; and
Origanum oil.

An aroma and flavoring concentrate containing one or more of the lactone derivative(s) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstitued tobacco material or tobacco substitutes (e.g., lettuce leaves) or mixtures thereof. The proportions of flavoring additives may be varied in accordance with taste but insofar as enhancement or the imparting of oriental and/or Turkish tobacco notes, we have found that satisfactory results are obtained if the proportion by weight of the sum total of lactone derivative(s) to smoking tobacco material is between 50 ppm and 1,500 ppm (0.005%–0.15%) of the active ingredients to the smoking tobacco material. We have further found that satisfactory results are obtained if the proportion by weight of the sum total of lactone derivative(s) used to flavoring material is between 500 and 15,000 ppm (0.05%–1.5%).

Any convenient method for incorporating the lactone derivative(s) into the tobacco product may be employed. Thus, the lactone derivative(s) taken alone or along with other flavoring additives may be dissolved in a suitable solvent such as ethanol, diethylether, and/or volatile organic solvents and the resulting solution may either be spread onto the cured, cased, and blended tobacco material or the toacco material may be dipped into such solution. Under certain circumstances, a solution of the lactone derivative(s) taken alone or taken further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus-treated tobacco may be blended with other tobaccos before the ultimate tobacco product is formed. In such cases, the tobacco treated may have the lactone derivative(s) in excess of the amounts or concentrations above indicated so that when blended with other tobaccos, the final product will have the percentage within the indicated range.

In accordance with one specific example of our invention, an aged, cured and shredded domestic Virginia tobacco is sprayed with a 20% alcohol solution of the compound having the structure:

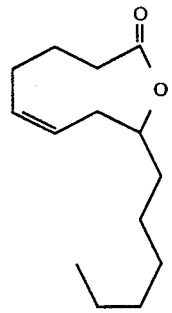

on a dry basis. Thereafter the alcohol is removed by evaporation and the tobacco is manufactured into cigarettes by the usual techniques. The cigarette, when treated as indicated, has a desired and pleasing aroma which is detectable in the main stream and the side stream when the cigarette is smoked. This aroma is described as being sweeter, with pronounced Turkish/oriental characteristics and with improved body and enhanced tobacco character in the main stream and side stream. In addition, interesting amber nuances are imparted.

While our invention is particularly useful in the manufacture of smoking tobacco such as cigarette tobacco, cigar tobacco and pipe tobacco, other tobacco products formed from sheeted tobacco dust or fines may also be used. Likewise the lactone derivative(s) of our invention can be incorporated with materials such as filter tip materials, seam paste, packaging materials and the like which are used along with tobacco to form a product adapted for smoking. Furthermore, the lactone derivative(s) can be added to certain tobacco substitutes of natural or synthetic origin (e.g., dried lettuce leaves) and, accordingly, by the term "tobacco" as used throughout this specification, is meant any composition intended for human consumption by smoking or otherwise when composed of tobacco plant parts or substitute materials or both.

EXAMPLE I

PREPARATION OF LACTONE COMPOSITION

Reactions:

(i)

-continued
Reactions:
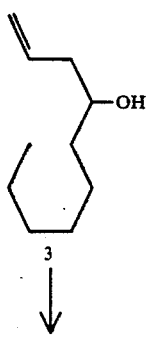
↓
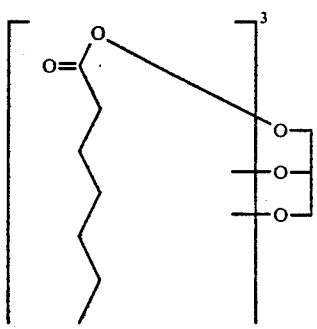
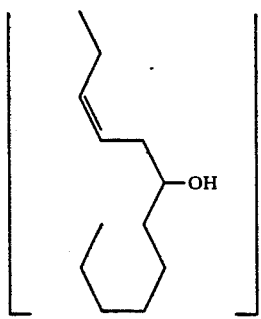
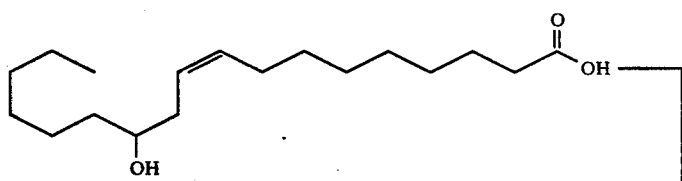
(ii)
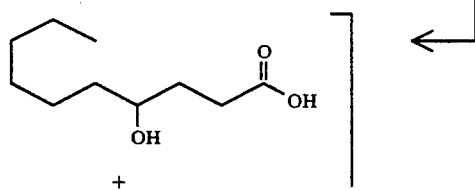
+
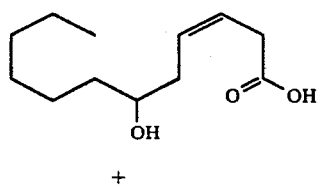
+

-continued
Reactions:
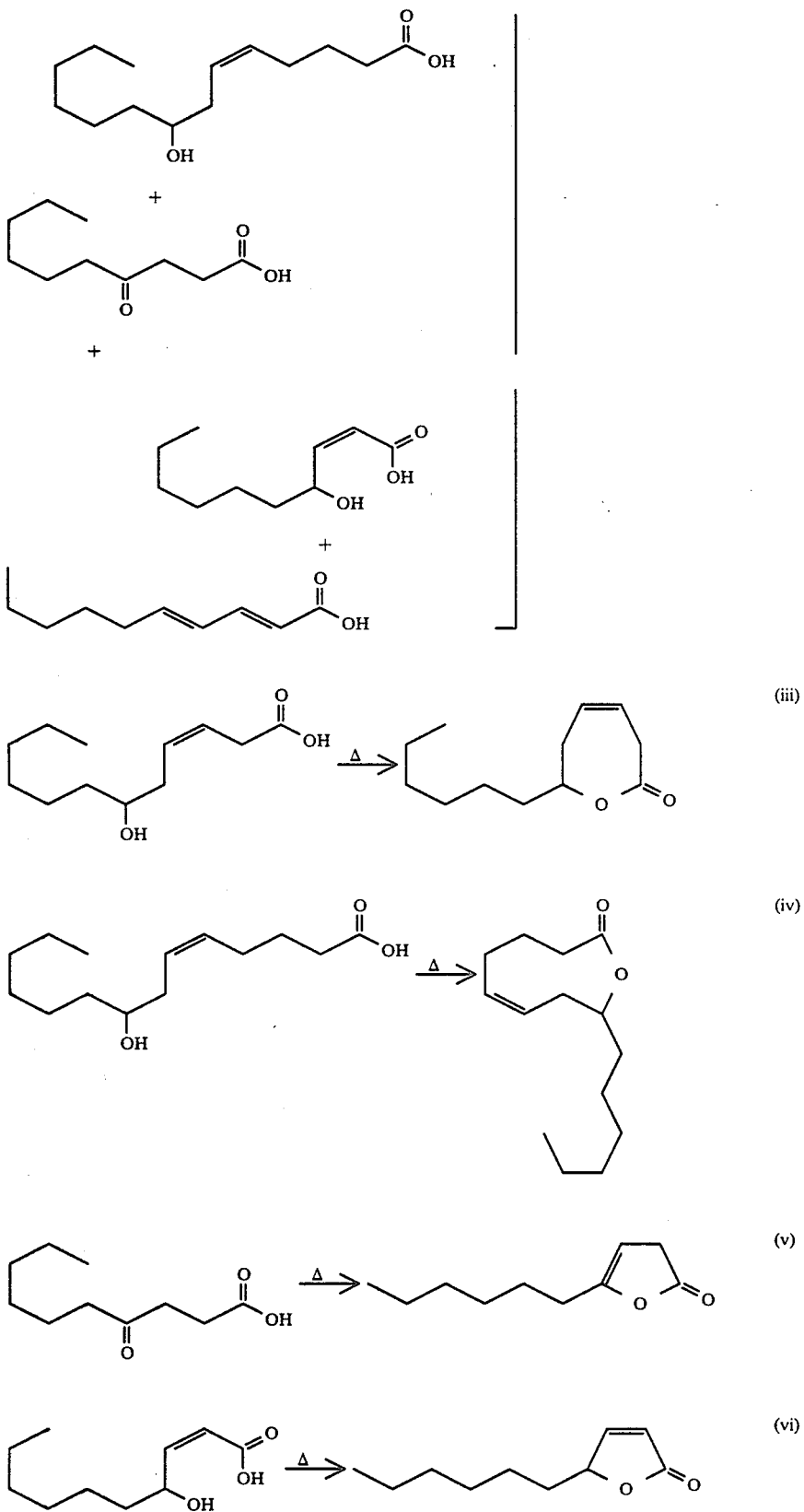

-continued

Reactions:

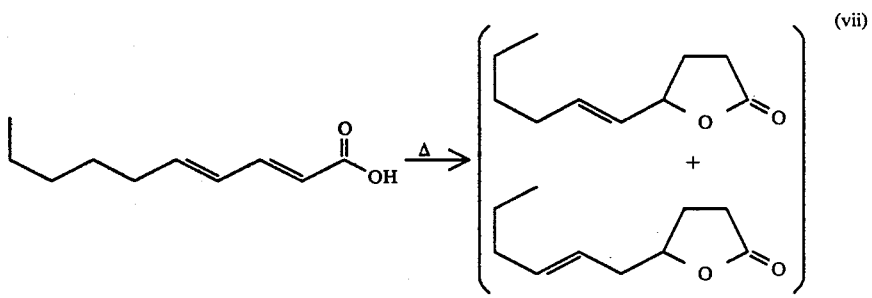
(vii)

and

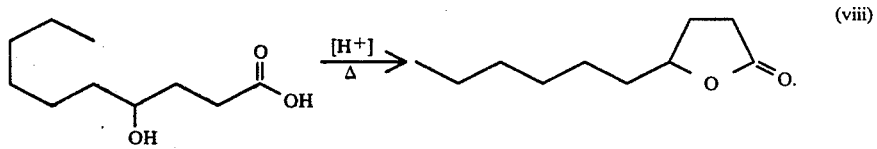
(viii)

Into a 200 liter fermentation vessel is placed a composition of matter containing 10% castor oil; 0.02% TWEEN® 80; 0.05% MgSO$_4$.7H$_2$O; 0.1% KH$_2$PO$_4$; 2% beef extract and *Candida petrophilum*, ATCC 20226. The fermentation conditions are as follows:

| Aeration: | 0.5 liters per minute |
|---|---|
| RPM: | 175 |
| Temperature: | 28° C. |
| Duration of fermentation: | 44 hours. |

Foaming was automatically controlled using silicone oil.

The *Candida petrophilum*, ATCC 20226 was added as 3 liter batch of inoculum consisting of 3% yeast extract; 0.1% KH$_2$PO$_4$; 0.05% MgSO$_4$7H$_2$O; 0.02% TWEEN® 80 and 10% olive oil (aqueous emulsion).

The pH of the fermentation batch was adjusted to 2 using 85% phosphoric acid and the fermentation batch was boiled at 100° C. for a period of 30 minutes after the 44 hour fermentation period.

The fermentation batch was then cooled to 25° C. and extracted with ethyl acetate using a counter-current extractor. Two passes were sufficient for the extraction. The ratio of broth:solvent was 2:1.

The ethyl acetate was removed in an evaporator and an oily residue of 6.1 kilograms was obtained.

The residue was subjected to fractional distillation in a 10 liter glass still using an 18" Goodloe column equipped with fraction cutter. The fractions obtained by this distillation are as follows:

| Fraction No. | Vapor Temp. (°C.) | Liquid Temp. (°C.) | Vacuum mm/Hg. Pressure | Reflux Ratio |
|---|---|---|---|---|
| 1 | 118/145 | 183/185 | 14.5 | 2:1 |
| 2 | 150 | 185 | 14.5 | 2:1 |
| 3 | 153 | 185 | 14.5 | 2:1 |
| 4 | 154 | 186 | 14.0 | 2:1 |
| 5 | 155 | 187 | 14.0 | 2:1 |
| 6 | 155 | 187 | 14.0 | 2:1 |
| 7 | 155 | 189 | 14.0 | 2:1 |
| 8 | 155 | 189 | 14.0 | 2:1 |
| 9 | 155 | 190 | 15.0 | 2:1 |
| 10 | 155 | 191 | 16.0 | 2:1 |
| 11 | 156 | 193 | 16.0 | 2:1 |
| 12 | 156 | 195 | 16.5 | 2:1 |
| 13 | 157 | 196 | 16.5 | 2:1 |
| 14 | 157 | 198 | 16.5 | 2:1 |
| 15 | 157 | 200 | 16.5 | 2:1 |
| 16 | 156 | 204 | 16.0 | 2:1 |
| 17 | 156 | 205 | 16.0 | 2:1 |
| 18 | 154 | 207 | 15.5 | 2:1 |
| 19 | 154 | 210 | 15.0 | 2:1 |
| 20 | 154 | 214 | 15.0 | 2:1 |
| 21 | 156 | 216 | 15.5 | 2:1 |
| 22 | 160 | 220 | 17.0 | 2:1 |
| 23 | 167 | 226 | 17.0 | 2:1 |
| 24 | 167 | 230 | 16.5 | 2:1 |
| 25 | 171 | 236 | 16.5 | 2:1 |
| 26 | 173 | 245 | 16.0 | 2:1 |
| 27 | 174 | 251 | 16.0 | 2:1. |

A total of 1351 grams of distillate in 29 fractions was obtained.

Fractions 1–19 were bulked and a mixed product was obtained. 898 grams of this product were analyzed and determined to contain the following materials:

0.8% of the compound having the structure:

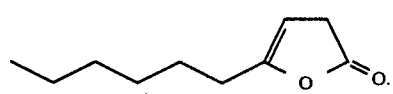

40.1% of the compound having the structure:

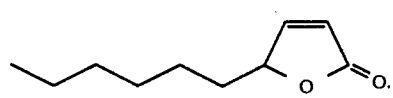

1.0% of the mixture of compounds having the structures:

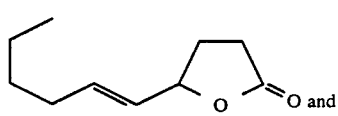
and

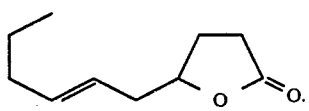

55.5% of the compound having the structure:

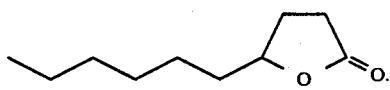

Fractions 23-27 were bulked (453 grams obtained) and determined to have the following components:

5.9% of the compound having the structure:

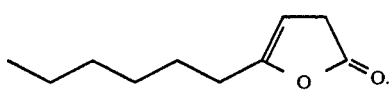

21.2% of the compound having the structure:

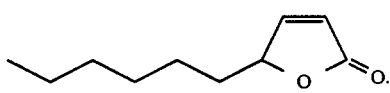

1.1% of the mixture of compounds having the structures:

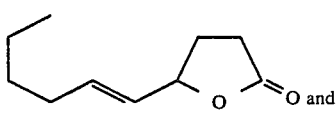

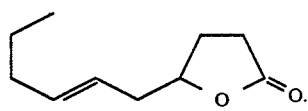

7.18% of the compound having the structure:

43.2% of the compound having the structure:

16.21% of the compound having the structure:

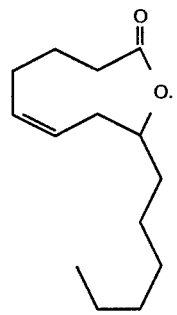

FIG. 1 is the GLC profile for bulked fractions 1-19. The peak indicated by reference numeral 10 is the peak for the compound having the structure:

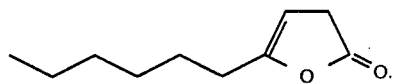

The peak indicated by reference numeral 11 is the peak for the compound having the structure:

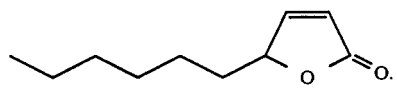

The peak indicated by reference numeral 12 is the peak for the compound having the structure:

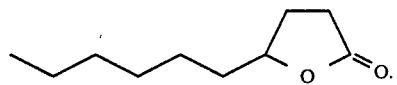

The peak indicated by reference numeral 13 is the peak for the mixture of compounds having the structures:

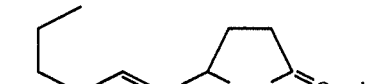

FIG. 2 is the GLC profile for bulked fractions 23-27. The peak indicated by reference numeral 20 is the peak for the compound having the structure:

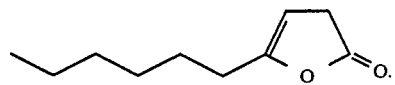

The peak indicated by reference numeral 21 is the peak for the compound having the structure:

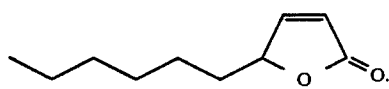
The peak indicated by reference numeral 22 is the peak for the mixture of compounds having the structures:
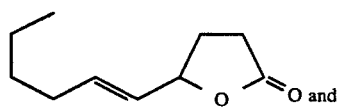
and
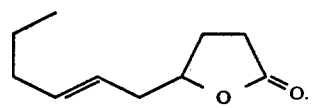
The peak indicated by reference numeral 23 is the peak for the compound having the structure:
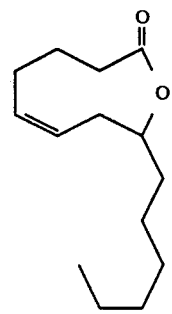
The peak indicated by reference numeral 24 is the peak for the compound having the structure:
EXAMPLE II
PREPARATION OF LACTONE COMPOSITION
Reactions:
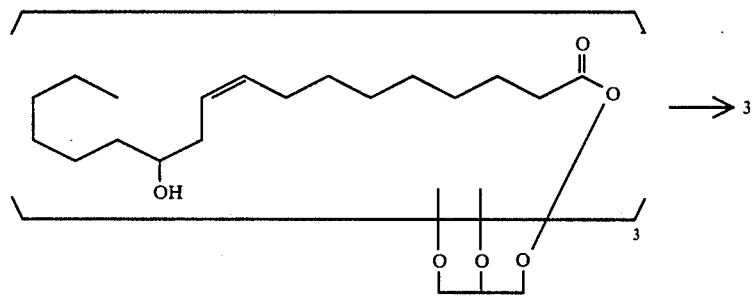
(i)
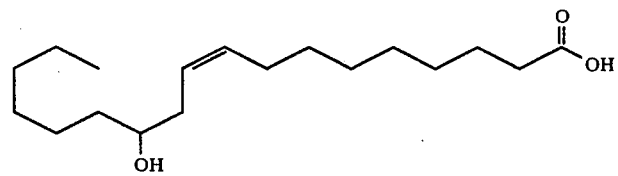
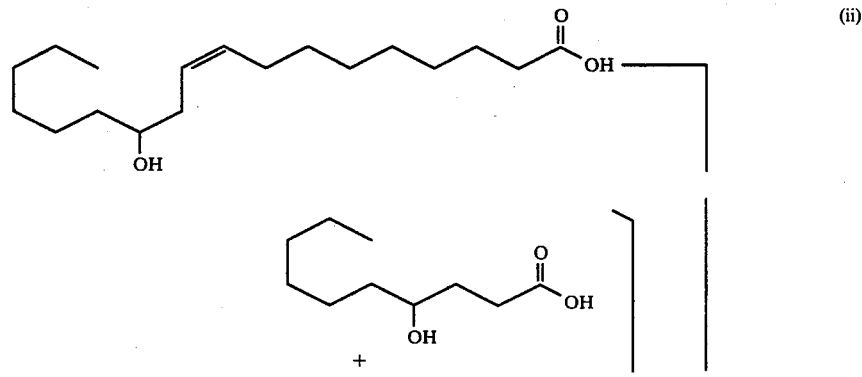
(ii)

Reactions:
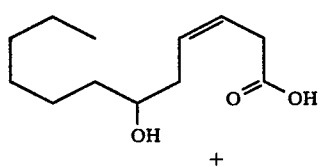
+
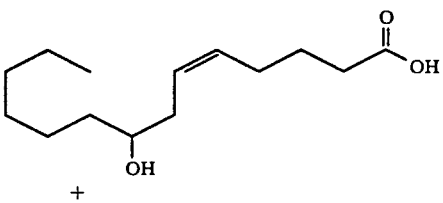
+
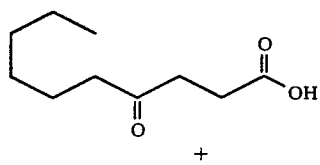
+
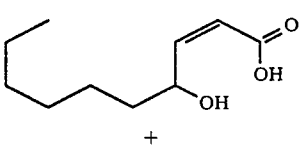
+
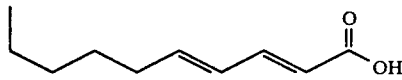
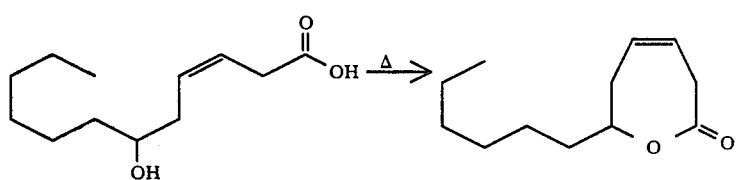 (iii)
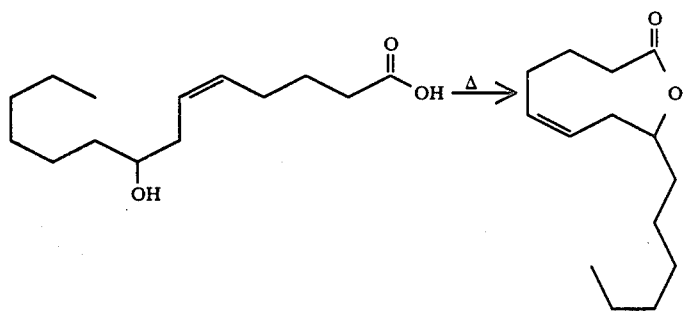 (iv)
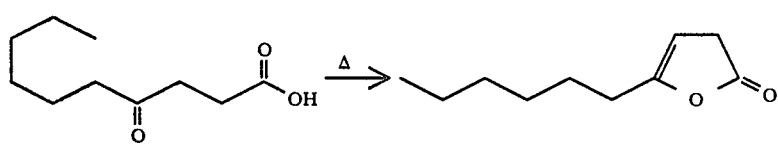 (v)
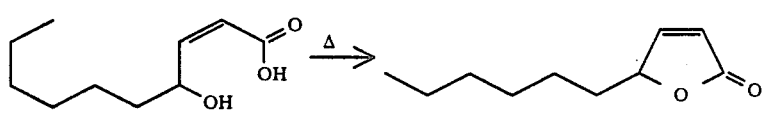 (vi)

Reactions:

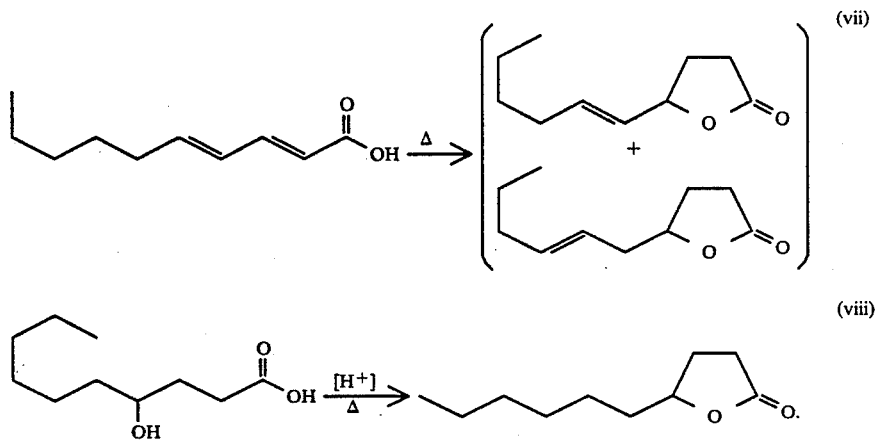

*Candida petrophilum*, ATCC 20226 inoculum (30 liters) was prepared by growing the *Candida petrophilum*, ATCC 20226 in a mixture of 3% yeast extract; 0.1% $KH_2PO_4$; 0.05% $MgSO_4.7H_2O$; 0.02% TWEEN® 80 and 10% olive oil at a pH of 7. The resulting inoculum was then added to the following fermentation reaction mass:

| | |
|---|---|
| 3% | AMBEREX ® 5500 |
| 0.1% | $KH_2PO_4$ |
| 0.05% | $MgSO_4.7H_2O$ |
| 0.02% | TWEEN ® 80 |
| 10% | castor oil. |

The fermentation conditions are as follows:

| | |
|---|---|
| Aeration: | 0.5 liters per minute per liter; |
| Back pressure: | 10 Psig; |
| RPM: | 75; |
| Temperature: | 28° C.; |
| Duration: | 48 hours. |

Automatic foam control was effected using silicone oil as an antifoam agent.

The pH was automatically kept at 6.9 using 50% aqueous sodium hydroxide. At the end of the fermentation period (48 hours) the pH was adjusted to 2 using 85% phosphoric acid. The resulting product was boiled at 100° C. for 30 minutes and then cooled to 25° C. The resulting product was then extracted with ethyl acetate using counter-current extraction. The solvent was then removed by means of evaporation.

365.5 Pounds of crude oil was obtained. The crude oil was fractionally distilled and 24 fractions were obtained having a total weight of 93.3 pounds.

The distillation fractions obtained are as follows:

| Fraction No. | Vapor Temp. (°C.) | Liquid Temp. (°C.) | Vacuum mm/Hg. Pressure | Reflux Ratio |
|---|---|---|---|---|
| 1 | 26/ | 175/ | 26/ | 1:1 |
| 2 | 140 | 196 | 24 | 1:1 |
| 3 | 145 | 198 | 22 | 1:1 |
| 4 | 145 | 198 | 22 | 1:1 |
| 5 | 148 | 198 | 22 | 1:1 |
| 6 | 150 | 198 | 22 | 1:1 |
| 7 | 160 | 200 | 22 | 1:1 |
| 8 | 164 | 200 | 22 | 1:1 |
| 9 | 164 | 200 | 23 | 1:1 |
| 10 | 165 | 205 | 23 | 1:1 |
| 11 | 165 | 205 | 23 | 1:1 |
| 12 | 165 | 205 | 24 | 1:1 |
| 13 | 168 | 210 | 24 | 1:1 |
| 14 | 170 | 210 | 24 | 1:1 |
| 15 | 170 | 212 | 24 | 1:1 |
| 16 | 172 | 215 | 23 | 1:1 |
| 17 | 172 | 220 | 23 | 1:1 |
| 18 | 176 | 225 | 23 | 1:1 |
| 19 | 176 | 228 | 23 | 1:1 |
| 20 | 175 | 230 | 23 | 1:1 |
| 21 | 177 | 240 | 22 | 1:1 |
| 22 | 178 | 240 | 22 | 1:1 |
| 23 | 178 | 255 | 17 | 1:1 |
| 24 | 178 | 265 | 6 | 1:1. |

Fraction 19 of the foregoing distillation contained the following materials:

2.9% of the compound having the structure:

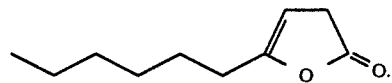

76.4% of the compound having the structure:

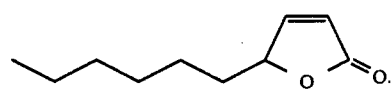

1.2% of the mixture of compounds having the structures:

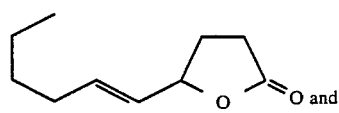

15.3% of the compound having the structure:

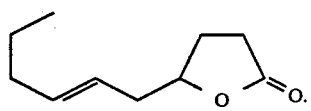

FIG. 3 is the GLC profile for fraction 19. The peak indicated by reference numeral 30 is the peak for the compound having the structure:

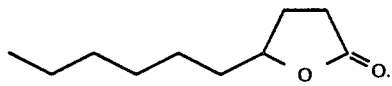

The peak indicated by reference numeral 31 is the peak for the mixture of compounds having the structures:

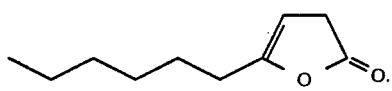

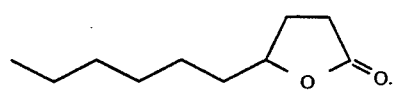

The peak indicated by reference numeral 32 is the peak for the mixtures of compounds having the structures:

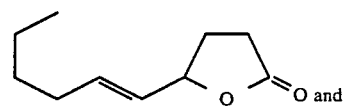

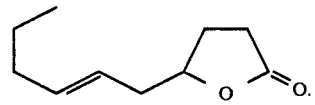

FIG. 4 is another GLC profile for fraction 19 of the foregoing distillation.

EXAMPLE III
PREPARATION OF MIXTURE OF LACTONES

Reactions:

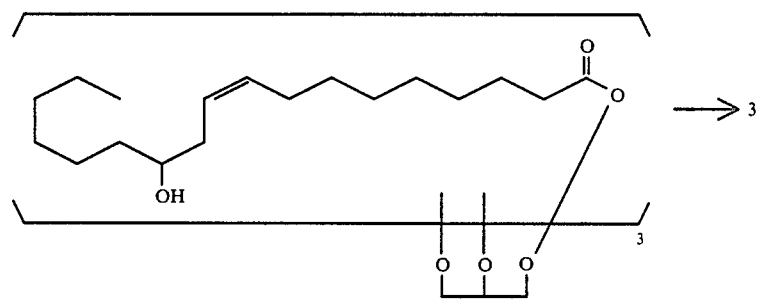   (i)

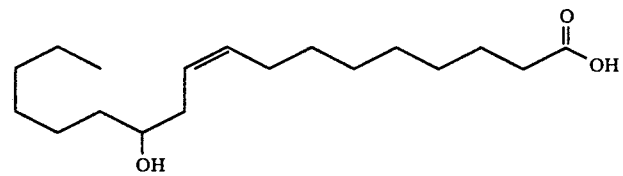

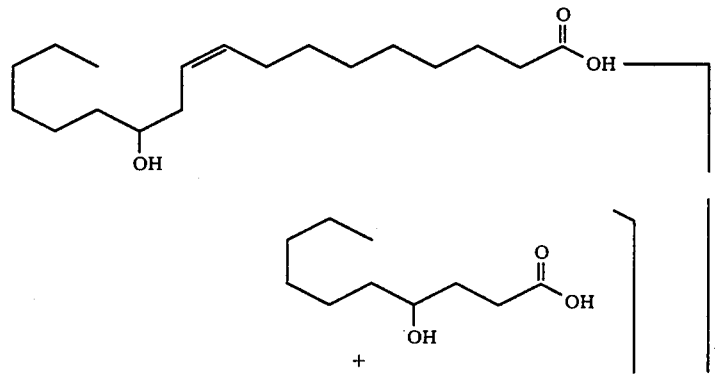   (ii)

Reactions:
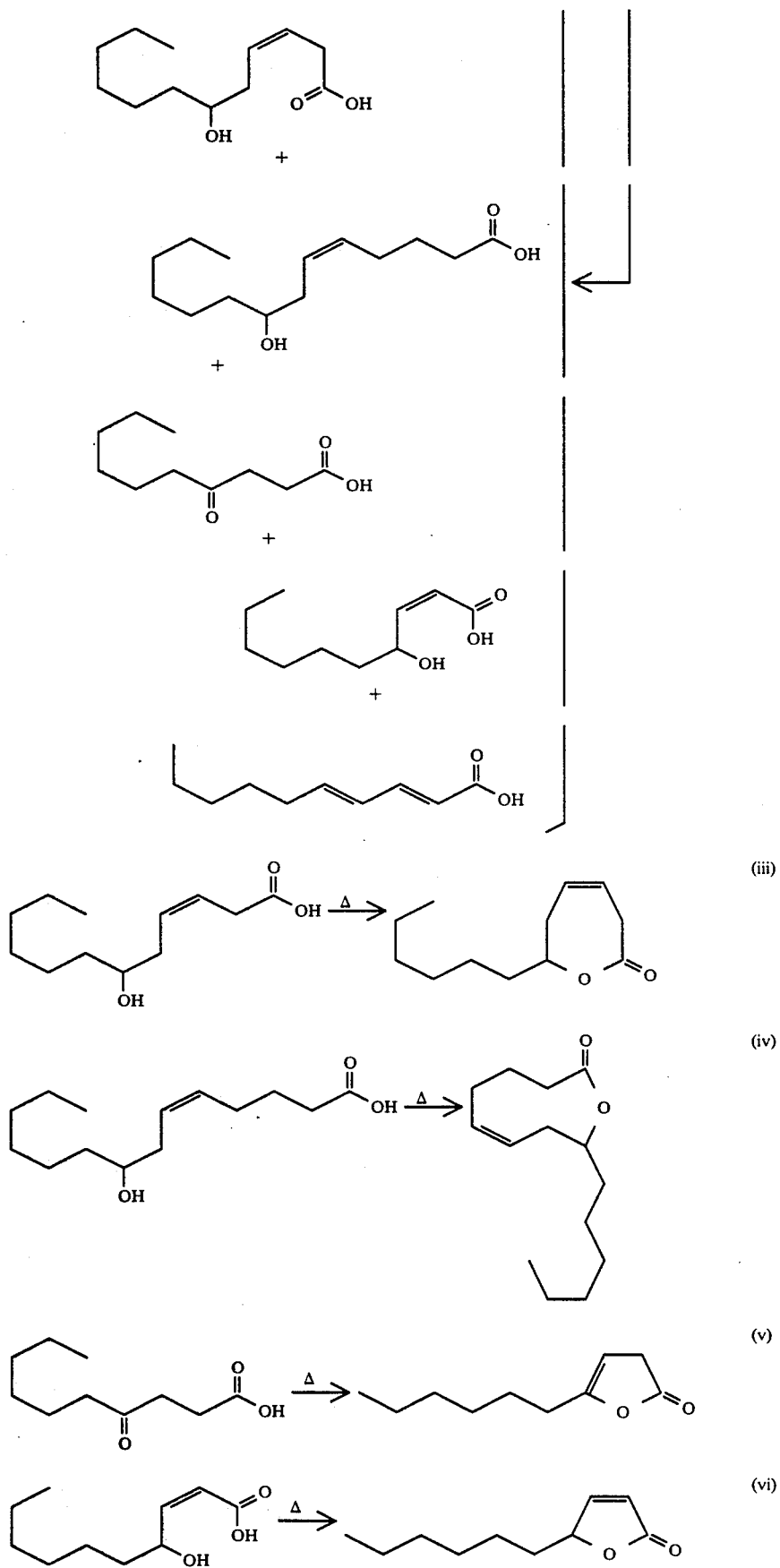

-continued

Reactions:

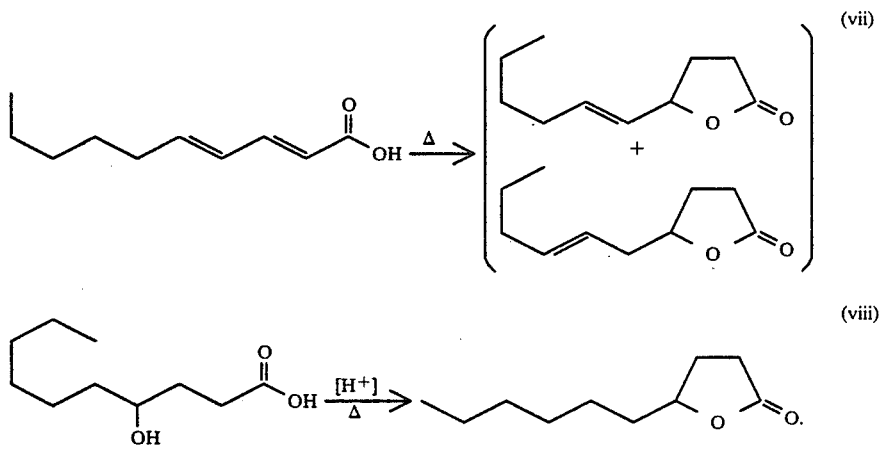

3.5 Liters of an inoculum of *Candida petrophilum*, ATCC 20226 was prepared by growing for 30 hours at 28° C. *Candida petrophilum* in the following inoculum medium:

| | |
|---|---|
| 3% | Yeast extract; |
| 0.1% | KH$_2$PO$_4$; |
| 0.05% | MgSO$_4$.7H$_2$O; |
| 0.02% | TWEEN ® 80; and |
| 10% | Olive oil. |

The pH of the inoculum medium was 7.0.

Into a 135 liter fermenter was placed 100 liters of the following material:

| | |
|---|---|
| 3% | Yeast extract; |
| 0.1% | KH$_2$PO$_4$; |
| 0.05% | MgSO$_4$.7H$_2$O; |
| 0.02% | TWEEN ® 80; and |
| 10% | Castor oil. |

Printout cancelled by operator.

The 3.5 liter mixture of inoculum was then added to the fermenter.

The fermentation conditions are as follows:

| | |
|---|---|
| pH: | 6.9 +/− 0.1. |
| Aeration: | 1 liter per minute per liter. |
| RPM: | 220. |
| Temperature: | 28° C. +/− 0.2° C. |
| Back pressure: | 10 psig. |

The foaming was controlled using automatic foam control and silicone oil as an antifoam.

The incubation time in this particular example was 29 hours.

At the end of the 29 hour period, the pH was adjusted to 2 using 85% phosphoric acid. The fermentation batch was then boiled at 100° C. for 30 minutes and cooled to room temperature. The fermentation batch was then extracted with two batches of ethyl acetate using counter current extraction.

The solvent was evaporated on an evaporator and 5500 grams of crude oil were obtained.

The 5500 grams of crude oil were placed in a 10 liter distillation flask using a 2"×18" Goodloe column at reflux ratio 2:1 and a vacuum of 20 mmHg. Distillation was carried out until the vapor temperature reached 160° C. and the pot temperature reached 212° C. A total of 1505 grams of distillate was obtained having a purity of 59%. 1500 grams of distillate were redistilled using a 3 liter flask and a 2"×18" Goodloe column with a reflux ratio of 4:1 at 1 mmHg. pressure and a pot temperature of 139°–164° C. and a vapor temperature of 116° C. All of the fractions were collected at a vapor temperature of 116° C. The combined fractions weighed 835 grams. FIG. 5 is the GLC profile for the resulting product.

EXAMPLE IV

PREPARATION OF LACTONES

Where reactions took place the reactions are as follows:

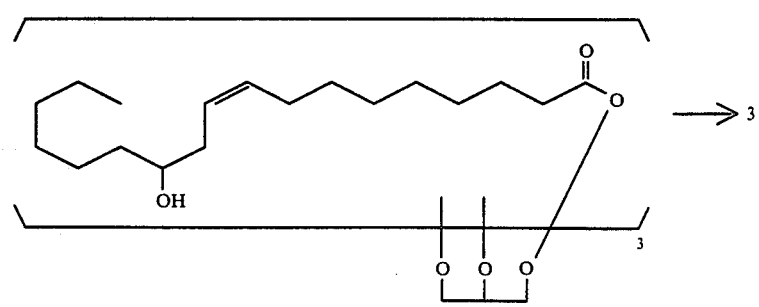

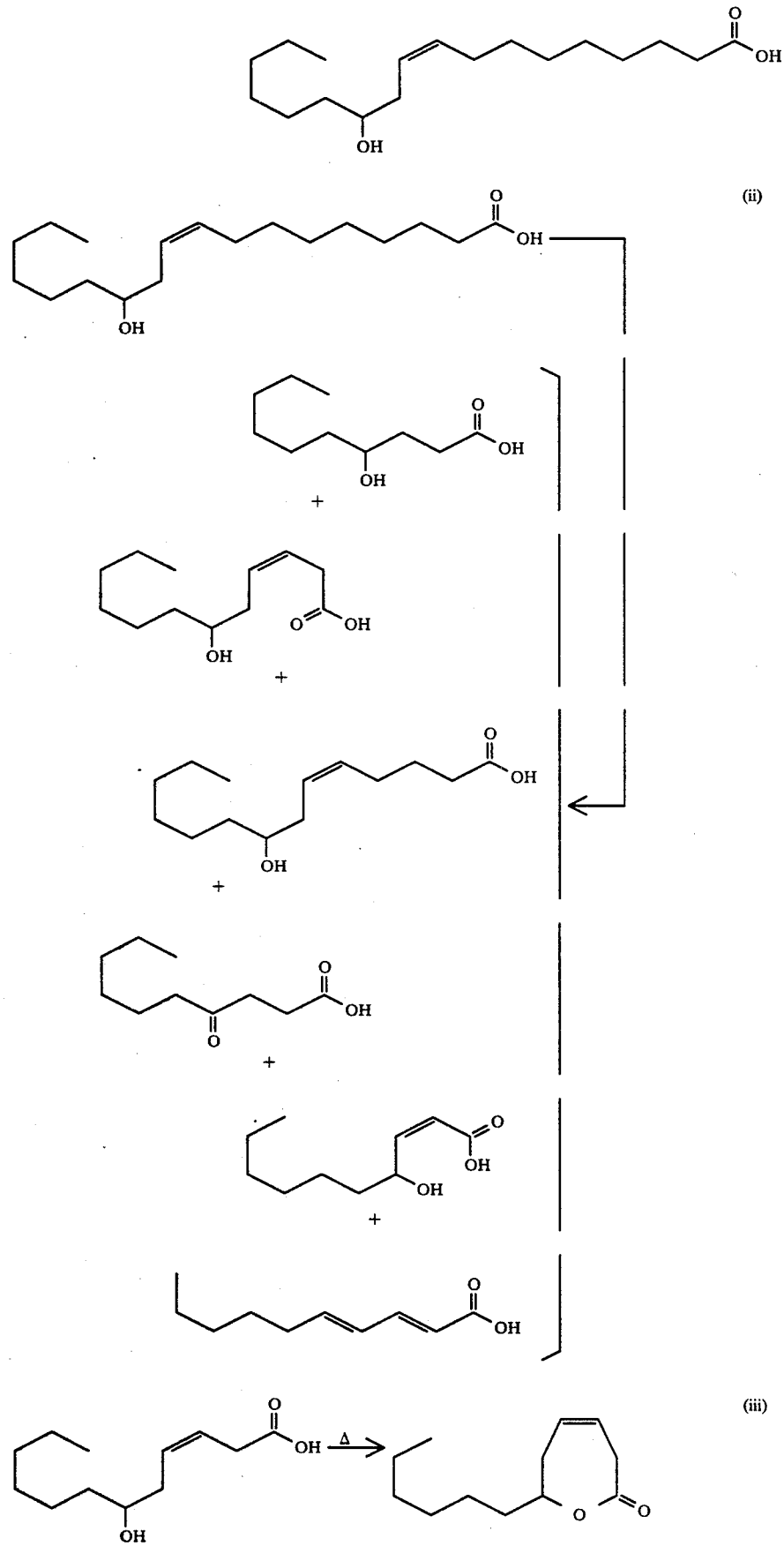

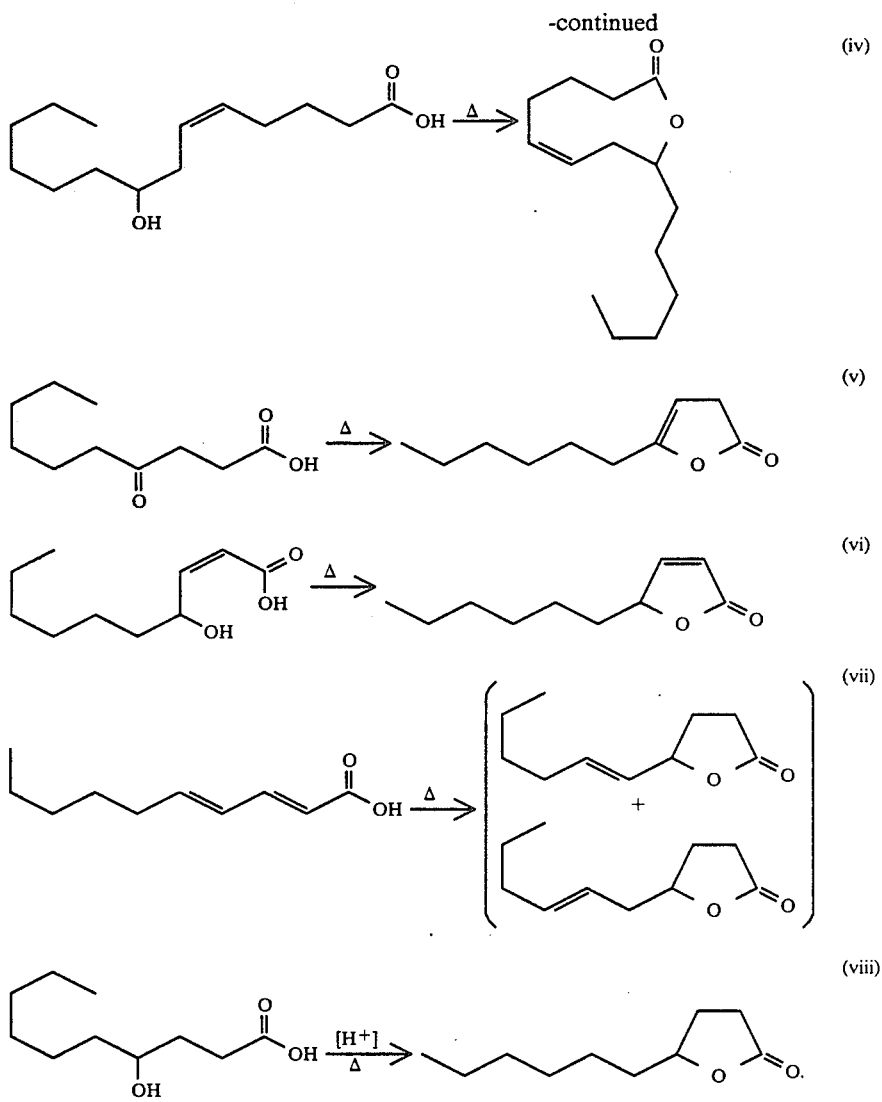

Fermentation runs using various organisms were carried out as follows where results as indicated below were obtained:

---

(i)
Temperature: 25° C.
RPM: 200
Media: 2% Beef extract, 0.1% yeast extract, 0.02% TWEEN ® 80
Substrate: Castor oil - 1 ml/100 ml broth.

| | Organism | ATCC # | Growth | Results |
|---|---|---|---|---|
| (1) | Candida utilis | 9226 | good | negative |
| (2) | Candida sake | 28137 | good | some lactone |
| (3) | Metarrhizium anisopliae | 26852 | fair | negative |
| (4) | *Myriococcum sp. | 20374 | fair | negative |
| (5) | Paecilomyces farinosus | 26853 | fair | negative |
| (6) | Penicillium caseicolum | 24936 | fair | negative |
| (7) | Rhizopus oryzae | 34612 | good | negative |

Samples from each flask were acidified to pH 2 with phosphoric acid and heated to lactonize.
*Incubated at 42° C.

---

(ii)
Temperature: 25° C.
RPM: 200
Media: 2% Malt extract, 0.1% Peptone, 0.02% TWEEN ® 80
Substrate: Castor Oil - 1 ml/100 ml broth.

| | Organism | ATCC # | Growth | Results |
|---|---|---|---|---|
| (1) | Candida utilis | 9226 | good | negative |
| (2) | Candida sake | 28137 | good | some lactone |
| (3) | Metarrhizium anisopliae | 26852 | fair | negative |
| (4) | *Myriococcum sp. | 20374 | fair | negative |
| (5) | Paecilomyces farinosus | 26853 | fair | negative |
| (6) | Penicillium caseicolum | 24936 | fair | negative |
| (7) | Rhizopus oryzae | 34612 | good | negative |

*Incubated at 42° C.

---

(iii)
Candida deformans revived from ATCC culture #22969 using YM agar.
Medium: 0.1% Yeast extract, 0.1% $KH_2PO_4$,
0.05% $MgSO_4.7H_2O$, 0.2% $(NH_4)_2 SO_4$, pH 6.5
0.05% TWEEN ® 80
Incubated: 25° C., 200 RPM
Substrate: 1 ml castor oil/flask
Growth: good
No lactone production observed.

-continued

Substrate: 1 ml P10 acid/flask
Growth: good
Very weak lactone odor after sample was acidified and heated.

(iv)
*Candida sp* (ATCC #20504) inoculated into 2 flasks.
Medium: 2% Malt extract, 0.1% Peptone,
 0.02% TWEEN ® 80
Incubated: 25° C., 200 RPM
Substrate: 1 ml P10 acid/flask.
96 Hrs. One flask acidified with phosphoric acid to pH 2
 Refluxed 30 minutes, extracted, and distilled
 0.055 grams product obtained.

(v)
Incubated: 25° C., 200 RPM
Substrate: P10 Acid, 1 ml/flask
Medium: 2% Malt extract, 0.1% Peptone, 0.02%,
 TWEEN ® 80

| Organism | Growth | Results |
|---|---|---|
| *C. petrophilum* 20226 | good | good |
| *C. periphelosum* 20314 | good | negative |
| *C. periphelosum* 20317 | good | negative |
| *C. oleophila* 20177 | good | good |
| *C. kefyr* 42265 | good | negative |

Medium: 2% Beef extract, 0.1% yeast extract,
 0.02% TWEEN ® 80

| Organism | Growth | Results |
|---|---|---|
| 20226 | good | some lactone - odor not as strong |
| 20314 | good | negative |
| 20317 | good | negative |
| 20177 | good | best lactone - strongest odor |
| 42265 | good | negative. |

(vi)
Incubated: 25° C., 200 RPM
Substrate: 1 ml P10 acid/100 ml broth
Media: (1) 2% Malt extract, 0.1% Peptone, 0.02%,
 TWEEN ® 80
 (2) 2% Beef extract, 0.1% yeast extract,
 0.02% TWEEN ® 80
2 Flasks of each medium inoculated for each organism.

| Organism | Growth | (1) Yield | (2) Yield |
|---|---|---|---|
| *Candida petrophilum* ATCC 20226 | good | 0.031 g | 0.057 g |
| *Candida oleophila* ATCC 20177 | good | 0.021 g | 0.038 g |
| *Candida sp.* ATCC 20504 | good | 0.021 g | 0.045 g |
| *Candida sake* ATCC 28137 | good | 0.021 g | 0.027 g |

To one set of flasks, 1.0 ml additional castor oil hydrolysate added after 40 hrs. For each organism, 0.5 ml additional castor oil hydrolysate was added to one flask of each medium after 18 hours incubation. Incubation was continued at 25° C., 200 RPM.

| Organism | Results (1) Yield | (2) Yield |
|---|---|---|
| *C. petrophilum* 20226 | 0.053 g | 0.028 g |
| *C. oleophila* 20177 | 0.040 g | 0.023 g |
| *Candida sp.* 20504 | 0.058 g | 0.039 g |
| *C. sake* 28137 | 0.029 g | 0.055 g |

Acidified after 48 hours incubation.

(vii)
Medium: 2% Malt extract, 0.1% Peptone,
 0.02% TWEEN ® 80
Incubation: 25° C., 150 RPM
Substrate: Castor oil hydrolysate.

| Organism | Amt. Substrate | Growth | Results |
|---|---|---|---|
| *Candida petrophilum* ATCC 20226 | 0.1 ml | good | weak |
| *Candida petrophilum* ATCC 20226 | 0.2 ml | good | weak |
| *Candida petrophilum* ATCC 20226 | 0.3 ml | good | weak |
| *Candida petrophilum* ATCC 20226 | 0.5 ml | good | strong/extracted 48 hrs. |
| *Candida sp.* ATCC 20504 | 0.1 ml | good | strong/extracted 48 hrs. |
| *Candida sp.* ATCC 20504 | 0.2 ml | good | strong/extracted 48 hrs. |
| *Candida sp.* ATCC 20504 | 0.3 ml | good | weak |
| *Candida sp.* ATCC 20504 | 0.5 ml | good | weak |
| *Candida sake* ATCC 28137 | 0.1 ml | good | weak |
| *Candida sake* ATCC 28137 | 0.2 ml | good | weak |
| *Candida sake* ATCC 28137 | 0.3 ml | good | weak |
| *Candida sake* ATCC 28137 | 0.5 ml | good | weak |

(viii)
Medium: 2% Beef Extract
 0.02% TWEEN ® 80
 2% Castor oil
Incubation: 25° C., 200 RPM.

| | Growth | |
|---|---|---|
| Candida sp. ATCC 20504 | good | pH (24 hrs) = 8.5 pH (48 hrs) = 7, remained at 7. |
| *C. petrophilum* 20226 | good | pH adjusted to 6.5 with NaOH during course of experiment. |
| *C. oleophila* 20177 | good | pH (24 hrs.) = 8.5 pH (30 hrs.) = 7, remained at 7. |
| *C. deformans* 22969 | good | pH remained at 7 throughout experiment. |

| | Results |
|---|---|
| 20504 | 144 hr. faint lactone odor. |
| 20226 | 120 hr. acidified to pH 1 w/H$_2$SO$_4$. |
| 20177 | 144 hr. negative. |
| 22969 | 144 hr. faint lactone odor. |
| 20226 | 144 hr. Extracted w/Ethyl Acetate. After distillation 0.281 g/100 ml, GC indicates no lactone present. |

(ix)
10 L. fermenter

| | |
|---|---|
| Medium: | 2% Beef Extract     pH = 7 |
| | 0.02% TWEEN ® 80 |
| | 0.05% Antifoam |
| | 3% Castor Oil. |
| Inoculated with: | 3% *Candida petrophilum* ATCC #20226 |
| | 24 hr. Shake flask culture, |
| | 2% Beef extract, |
| | 0.02% TWEEN ® 80, |
| | 1% Castor Oil. |
| Fermentation Conditions: | |
| | 27° C., 420 RPM |
| | pH continuously adjusted to 6.5 w/NaOH |
| | antifoam added as needed. |
| | 24 Hr. 100 ml Sample - growth good. |

Procedure for all samples:
1. Acidifed to pH 2 with 50% H$_2$SO$_4$.
2. Refluxed 30 minutes.
3. Extract 3× with Ethyl Acetate (100 ml each time).
4. Wash with saturated NaCl (50 ml).
5. Wash with saturated NaHCO$_3$ 3× (20 ml each time).
6. Wash with saturated NaCl 3× (50 ml each time).
7. Dry over anhydrous sodium sulfate (granular).
8. Evaporate solvent.
9. Distill 235° C., for 2 hrs., at 5 mm/Hg.

32 hrs. - 100 ml sample - growth - good.
48 hrs. - 100 ml Sample - growth - good.
56 hrs. - 100 ml Sample - growth - good.
72.0 hrs. - 100 ml Sample - growth - good.
78.5 hrs. - 100 ml Sample - growth - good.

Results

| Time (hrs) | % Dissolved Oxygen | Crude Wgt (g) | Sample Wgt (g) | % Purity | Yield (g) |
|---|---|---|---|---|---|
| 24 | 28 | 3.0 | 0.35 | 88.7 | 0.31 |
| 32 | 36 | 2.2 | 0.47 | 82.0 | 0.39 |
| 48 | 62 | 2.4 | 0.53 | 82.1 | 0.44 |
| 56 | 69 | 2.0 | 0.50 | 95.0 | 0.48 |
| 72 | 76 | 2.4 | 0.59 | 47.2 | |
| | | | 0.34 | 17.5 | 0.34 |
| 78.5 | 80 | 1.5 | 0.25 | 49.0 | 0.12 |

(x)

| | |
|---|---|
| Medium: | 0.1% Yeast extract |
| | 0.1% Beef extract |
| | 0.2% NH$_4$NO$_3$ |
| | 0.02% TWEEN ® 80 |
| | 0.05% Antifoam |
| | 3% Castor Oil. |
| Inoculated: | 3% *Candida petrophilum*, ATCC 20226 |
| | 24 Hr. Shake flask culture. |
| Fermentation Conditions: | |
| | 27° C., 420 RPM |
| | pH continuously adjusted to 6.5 |
| | W/50% NaOH |
| | antifoam added as needed |
| | aeration rate 4.0 L/min. |

100 ml Samples taken at following times:

| | Growth |
|---|---|
| 24 hrs. | good |
| 32 hrs. | good |
| 48 hrs. | good |
| 56 hrs. | good |
| 72 hrs. | good |
| 80 hrs. | good |
| 144 hrs. | good. |

Results:

| Time (hrs.) | dO$_2$ (%) | Crude Wgt (g) | Sample Wgt (g) | % Purity | Yield (g) |
|---|---|---|---|---|---|
| 24 | 68 | 2.32 | 0.19 | 86.0 | 0.14 |
| 32 | 60 | 2.28 | 0.21 | 93.0 | 0.2 |
| 48 | 82 | 1.63 | 0.26 | 98.0 | 0.25 |
| 56 | 86 | 1.51 | 0.19 | 98.6 | 0.187 |
| 72 | 92 | 1.43 | 0.20 | 98.7 | 0.197 |
| 80 | 93 | 1.58 | 0.37 | 88.0 | 0.325 |
| 144 | 92 | 1.14 | 0.31 | 55.0 | 0.17. |

(xi)

| | |
|---|---|
| Medium: | 0.1% Yeast extract |
| | 0.1% Beef extract |
| | 0.4% NH$_4$NO$_3$ |
| | 0.02% TWEEN ® 80 |
| | 0.05% Antifoam |
| | 3% Castor oil. |
| Inoculum: | 3% *Candida petrophilum*, ATCC 20226 |
| | 64 Hr. shake flask culture. |
| Fermentation Conditions: | |
| | 27° C., 420 RPM |
| | pH = 6.5 |
| | aeration rate = 4.0 L/min. |
| | antifoam added as needed. |

100 ml Samples taken at following times:

| Time | Growth |
|---|---|
| 24 hr. | good |
| 32 hr. | good |
| 48 hr. | good |
| 56 hr. | good |
| 72 hr. | good |
| 80 hr. | good |
| 96 hr. | good |
| 101 hr. | good |

Results

| Time (hrs.) | dO$_2$ (%) | Crude Wgt (g) | Sample Wgt (g) | % Purity | Yield (g) |
|---|---|---|---|---|---|
| 24 | 28 | 2.36 | 0.14 | 89.7 | 0.126 |
| 32 | 36 | 1.70 | 0.14 | 80.0 | 0.112 |
| 48 | 58 | 1.36 | 0.21 | 93.5 | 0.196 |
| 56 | 58 | 1.79 | 0.35 | 88.6 | 0.316 |
| 72 | 74 | 1.67 | 0.29 | 77.0 | 0.223 |
| 80 | 78 | 1.44 | 0.30 | 78.6 | 0.236 |
| 96 | 90 | 1.54 | 0.36 | 72.1 | 0.26 |
| 101 | 90 | 1.61 | 0.33 | 69.7 | 0.230 |

(xii)

| | |
|---|---|
| Medium: | 0.1% Yeast extract |
| | 0.1% Beef extract |
| | 0.2% NH$_4$NO$_3$ |
| | 0.02% TWEEN ® 80 |
| | 0.05% Antifoam |
| | 3% Castor oil. |
| Inoculum: | 3% *Candida oleophila*, ATCC 20177 |
| | 24 hrs. Shake flask culture. |

27° C., 420 RPM, aeration rate = 4.0 L/min., pH = 6.5.

| Time | Growth | dO$_2$ (%) | Crude Wt (g) | Sample Wt (g) | % Purity | Yield (g) |
|---|---|---|---|---|---|---|
| 24 hr. | good | 67 | 2.38 | 0.27 | 76.48 | 0.21 |
| 32 | good | 30 | 2.35 | 0.09 | 94.43 | 0.085 |
| 48 | good | 78 | 1.69 | 0.16 | 46.41 | 0.07 |
| 56 | good | 80 | 1.79 | 0.11 | 51.2 | 0.06 |
| 72 | good | 81 | 1.47 | 0.06 | 73.34 | 0.04 |
| 77 | good | 82 | 1.40 | 0.08 | 54.28 | 0.04 |

(xiii)

| | |
|---|---|
| Medium: | 0.1% Beef extract |
| | 0.1% Yeast extract |
| | 0.2% NH$_4$NO$_3$ |
| | 0.02% TWEEN ® 80 |
| | 0.05% Antifoam |
| | 5% Castor oil. |
| Inoculum: | 3% *Candida oleophila*, ATCC 20177 |
| | 24 hr. shake flask culture. |

27° C., 420 RPM, pH = 6.5, aeration rate = 4.0 L/min.

Procedure for each 100 ml sample.

| | dO$_2$ | Crude | Sample | % | Yield |

-continued

| Time | Growth | dO$_2$ (%) | Crude Wt (g) | Sample Wt (g) | % Purity | Yield (g) |
|---|---|---|---|---|---|---|
| 24 hr. | good | 69 | 2.40 | 0.03 | 98.52 | 0.03 |
| 32 | good | 74 | 2.39 | 0.09 | 97.51 | 0.09 |
| 48 | good | 80 | 3.15 | 0.16 | 98.99 | 0.159 |
| 57 | good | 78 | 1.86 | 0.02 | 98.63 | 0.02 |
| 72 | good | 78 | 3.30 | 0.11 | 98.51 | 0.108 |
| 77 | good | 77 | 2.06 | 0.10 | 98.49 | 0.1 |

(xiv)
Medium: 0.1% Beef extract
0.1% Yeast extract
0.2% NH$_4$NO$_3$
0.02% TWEEN ® 80
0.05% Antifoam
5% Castor oil.
Inoculum: 3% Candia oleophila, ATCC 20177
24 Hr. Shake flask culture.
27° C., 420 RPM, pH = 6.5, aeration rate = 4.0 L/min.

Procedure followed for each 100 ml sample.

| Time | Growth | dO$_2$ (%) | Crude Wt (g) | Sample Wt (g) | % Purity | Yield (g) |
|---|---|---|---|---|---|---|
| 24 hr. | good | 91 | 3.29 | 0.06 | 98.02 | 0.059 |
| 31 | good | 93 | 3.52 | 0.08 | 99.62 | 0.08 |
| 48 | good | 95 | 3.23 | 0.16 | 88.63 | 0.14 |
| 56 | good | 95 | 3.85 | 0.18 | 78.54 | 0.14 |
| 72 | good | 97 | 3.66 | 0.19 | 75.92 | 0.14 |
| 76 | good | 97 | 3.65 | 0.15 | 81.28 | 0.12 |

(xv)
Medium: 0.1% Beef extract, 0.1% yeast extract, 0.4% NH$_4$NO$_3$, 0.02% TWEEN ® 80, 0.05% antifoam, 5% Castor oil.
27° C., 420 RPM, aeration rate = 4.0 L/min.
Procedure for each 100 ml sample.
Inoculum: 3%, 24 hrs. shake flask cultures.

| Time | Growth | dO$_2$ (%) | Crude Wt (g) | Sample Wt (g) | % Purity CBW | OVI | Yield (g) |
|---|---|---|---|---|---|---|---|
| Candida petrophilum, ATCC 20226. | | | | | | | |
| 24 hr. | good | 10 | 2.26 | 0.06 | 57.9 | 56.9 | 0.03 |
| 31 | good | 10 | 3.15 | 0.15 | 70.6 | 70.8 | 0.11 |
| 48 | good | 40 | 2.10 | 0.17 | 74.3 | 75.2 | 0.13 |
| 56 | good | 45 | 2.84 | 0.19 | 86.7 | 87.7 | 0.17 |
| 72 | good | 40 | 3.16 | 0.24 | 72.8 | 73.6 | 0.18 |
| 77 | good | 50 | 2.87 | 0.06 | 79.3 | 82.4 | 0.05 |
| Candidia oleophila, ATCC 21077 | | | | | | | |
| 24 hr. | good | 30 | 1.70 | 0.04 | 83.7 | 85.7 | 0.03 |
| 31 | good | 6 | 4.51 | 0.10 | 56.0 | 57.4 | 0.06 |
| 48 | good | 35 | 3.42 | 0.05 | 79.1 | 80.1 | 0.04 |
| 56 | good | 35 | 4.27 | 0.06 | 37.6 | 36.8 | 0.02 |
| 72 | good | 30 | 4.58 | 0.08 | 50.9 | 50.2 | 0.04 |
| 77 | good | 33 | 4.54 | 0.06 | 38.9 | 42.1 | 0.02 |

(xvi)
Medium: 2% Malt extract, 0.1% peptone, 0.02% TWEEN ® 80, 0.05% antifoam, 5% Castor oil.
27° C., 420 RPM, aeration rate = 4.0 L/min. pH = 6.5.
Inoculum: 3% Candida petrophilum, ATCC 20226
24 hour shake flask culture.
Procedure followed for each sample.

100 ml Samples taken at the following times:

| Time | Growth | dO$_2$ (%) | Crude Wt (g) | Sample Wt (g) | % Purity CBW | OVI | Yield (g) |
|---|---|---|---|---|---|---|---|
| 24 hr. | good | 75 | 3.34 | 0.08 | 78.8 | 89.4 | 0.06 |
| 30 | good | 77 | 3.27 | 0.23 | 63.2 | 62.1 | 0.14 |
| 48 | good | 74 | 3.19 | 0.11 | 69.1 | 65.4 | 0.07 |
| 56 | good | 73 | 4.00 | 0.19 | 74.2 | 68.4 | 0.13 |
| 72 | good | 70 | 3.56 | 0.18 | 78.7 | 77.0 | 0.14 |
| 77 | good | 71 | 3.24 | 0.25 | 75.4 | 72.8 | 0.18 |

(xvii)
Medium: 2% Malt extract, 0.1% peptone, 0.02% TWEEN ® 80, 0.05% antifoam, 5% castor oil.
27° C., 420 RPM, aeration rate = 4.0 L/min., pH = 6.5.
Inoculum: 3% Candidia oleophila, ATCC 21077
24 hr. shake flask culture.

Procedure followed for each sample.

| Time | Growth | dO$_2$ (%) | Crude Wt (g) | Sample Wt (g) | % Purity CBW | OVI | Yield (g) |
|---|---|---|---|---|---|---|---|
| 24hr. | good | 90 | 2.39 | 0.05 | 17.6 | 17.2 | 0.01 |
| 30 | good | 90 | 3.20 | 0.07 | 7.2 | 6.9 | 0.005 |
| 48 | good | 96 | 3.86 | 0.06 | 77.0 | 72.3 | 0.04 |
| 55 | good | 97 | 2.64 | 0.03 | 2.8 | 2.8 | 0.0008 |
| 72 | good | 97 | 2.80 | 0.04 | 19.1 | 18.2 | 0.007 |
| 77 | good | 97 | 2.89 | 0.03 | 0.3 | 0.3 | 0.00009 |

(xviii)
Medium: Malt extract 3 g/L, Peptone 5 g/L, yeast extract 3 g/L
26° C., 200 RPM.
Substrate: 2% Castor oil.

| | 24 hr. | | 48 hr. | | 72 hr. | | 96 hr. | | 120 hr |
|---|---|---|---|---|---|---|---|---|---|
| | pH | Lact | pH | Lact | pH | Lact | pH | Lact | Lact |
| Penicillium aurantiogris #34613 | 6.0 | — | 5.5 | — | 6.0 | + | 6 | — | — |
| Penicillium chrysogenum #100026 | 5.0 | — | 6.0 | — | 5.5 | — | 6 | — | — |
| Proteus mitajiri #21136 | 8.0 | — | 8.0 | — | 7.0 | — | 8.0 | — | — |
| Serratia grimesii #E 14460 | 6.5 | — | 6.0 | + | 6.0 | — | 6.0 | — | — |
| Serratia liquefaciens #11367 | 6.5 | — | 7.0 | — | 6.0 | — | 6.0 | — | — |
| Xanthomonas campestris #19155 | 6.0 | + | 6.0 | + | 8.0 | — | 8.5 | — | — |
| Rhodococcus sp. #21504 | 5.5 | — | 6.0 | + | 6.0 | + | 6.0 | + | + |
| Rhodococcus sp. #21507 | 6.0 | — | 5.5 | — | 7.0 | + | 7.5 | + | + |
| Rhodococcus sp. #21508 | 6.0 | — | 6.0 | — | 6.0 | + | 6.0 | — | — |

(xix)
Medium: Malt extract 3 g/L, Peptone 5 g/L, yeast extract 3 g/L
26° C., 200 RPM.
Substrate: 0.5% Castor oil hydrolysate.

| | 24 hr | | 48 hr | | 72 hr | | 96 hr | | 120 hr | | 216 hr | |
|---|---|---|---|---|---|---|---|---|---|---|---|---|
| | pH | Lac | pH | Lac | pH | Lac | pH | Lac | pH | Lac | pH | Lac |
| Penicillium | 6 | — | 6 | — | 7 | — | 7.5 | — | — | — | — | — |

-continued

| | | | | | | | | | | | | |
|---|---|---|---|---|---|---|---|---|---|---|---|---|
| *aurantiogris* #34613 | | | | | | | | | | | | |
| *Penicillium chrysogenum* #100026 | 6 | — | 6 | — | 5.5 | + | 7 | + | — | + | 4 | — |
| *Proteus mitajiri* #21136 | 6 | — | 6.5 | + | 7 | — | 7 | — | — | — | — | — |
| *Serratia grimesii* #E14460 | 6.5 | + | 7.5 | — | 8.5 | — | 8 | — | — | — | — | — |
| *Serratia liquefaciens* #11367 | * | — | ** | | 5 | + | 4.5 | + | 4.5 | — | | |
| *Xanthomomonas campestris* #191556 | 6 | — | 7 | — | 8 | + | 8.5 | — | — | — | — | — |
| *Rhodococcus* sp. #21504 | 6 | — | 6 | — | 6 | — | 6 | — | — | — | — | — |
| *Rhodococcus* sp. #21507 | 6 | — | 6 | — | 6 | + | 6 | — | — | + | — | — |
| *Rhodococcus* sp. #21508 | 6 | — | * | | ** | | 6 | + | 6 | — | 6 | — |

*Flask broke.
**Inoculate.

(xx)
Medium: 2% Beef extract    Temperature: 27° C.
 0.2% Yeast extract    RPM: 420
 0.02% TWEEN ® 80    Aeration: 0.5 v/v/min.
 0.05% Antifoam    pH = 6.5
 3% Castor Oil
Inoculum: 3% *Candida petrophilum*, ATCC 20226

| Time | Crude Wt | Distilled Wt | % Purity | Yield (g/L) | dO$_2$ |
|---|---|---|---|---|---|
| 24 hr. | 1.9 g | 0.25 | 96.11 | 2.4 | 14 |
| 30 | 1.0 | 0.20 | 94.17 | 1.9 | 24 |
| 48 | 1.0 | 0.39 | 30.45 | 1.2 | 64 |
| 56 | 1.0 | 0.17 | 96.25 | 1.8 | 81 |
| 72 | 0.78 | 0.1 | 91.96 | 0.9 | 86 |
| 96 | 0.2 | 0.17 | 37.35 | 0.6 | 95 |

100 ml Samples:
Centrifuge
Extract 3×, 100 ml ethyl acetate each time
Wash with sat'd NaCl (50 ml)
Wash with sat'd NaHCO$_3$ 3× (20 ml each time)
Wash with sat'd NaCl 3× (50 ml each time)
Dry over anhydrous sodium sulfate
Evaporate solvent
Distill at 225° C., 1 mmHg.

(xxi)
Medium: 2% Beef extract    Temperature = 27° C.
 0.1% Yeast extract    Agitation = 420 RPM
 0.02% TWEEN ® 80    Aeration: 0.5 v/v/min.
 0.05% Antifoam    pH = 6.5
 3% Castor Oil.
Inoculum: 3% *Candida petrophilum*

200 ml Samples taken, acidify w/H$_2$SO$_4$, to pH = 1.5, reflux 30 min.

| Time | Crude Wt | Distilled Wt | % Purity | Yield (g/L) |
|---|---|---|---|---|
| 24 hr. | 0.9 g | 0.17 g | 94.0 | 0.94 g/L |
| 30 | 1.71 | 0.33 | 92.36 | 1.52 |
| 48 | 1.2 | 0.19 | 95.04 | 0.90 |
| 54 | 1.2 | 0.21 | 85.29 | 0.9 |
| 72 | 1.0 | 0.14 | 41.21 | 0.29 |

For each sample:
Centrifuge
Extract 3×, 1:1 solvent to broth
Wash with sat'd NaCl
Wash with sat'd NaHCO$_3$ (3×)
Wash with sat'd NaCl (3×)
Dry over anhydrous sodium sulfate
Evaporate solvent
Distill at 225° C., 1 mmHg., 2 hours.

(xxii)
C-3 10L
Medium: 2% Beef extract    Aeration: 1.0 v/v/min.
 0.1% Yeast extract    Temperature = 27° C.
 0.02% TWEEN ® 80    Agitation = 420 RPM
 0.05% Antifoam    pH = 6.5
 3% Castor Oil.
Inoculum: 3% *Candida petrophilum*, ATCC 20226

200 ml Samples.

| Time | Crude Wt. (g) | Distilled Wt. (g) | % Purity | Yield (g/L) |
|---|---|---|---|---|
| 24 hr | 17 | 5.7 | 0.44 | 92.18 | 2.03 |
| 30 | 37 | 5.8 | 0.37 | 94.07 | 3.52 |
| | | | 0.31 | 92.78 | |
| | | | 0.66 | 9.91 | |
| 48 | 66 | 7.8 | 0.28 | 93.15 | 2.54 |
| | | | 0.12 | 92.05 | |
| | | | 1.44 | 9.45 | |

(xxiii)
C-2 10L
Medium: 2% Beef extract    pH = 6.5
 0.1% Yeast extract    Aeration: 1.0 v/v/min.
 3% Castor Oil    Temperature = 27° C.
 0.02% TWEEN ® 80    420 RPM
 0.05% Antifoam.
Inoculum: 3% *Candida petrophilum*, ATCC 20226

| Time | Crude Wt. | Distilled Wt. | % Purity | Yield (g/L) |
|---|---|---|---|---|
| 23 hr. | 0.9 g | 0.22 g | 94.12 | 2.07 |

(xxiv)
Medium: 2% Beef extract  pH = 6.5
0.1% Yeast extract  Aeration: 1.0 v/v/min.
5% Castor Oil  Temperature = 27° C.
0.02% TWEEN ® 80  Agitation = 420 RPM
0.05% Antifoam.
Inoculum: 3% *Candida petrophilum*, ATCC 20226
100 ml Samples.

| Time | Crude Wt. | Distilled Wt. | % Purity | Yield (g/L) |
|---|---|---|---|---|
| 21 hr. | 5.8 g | 0.29 g | 87% | 2.52 |
| 26 hr. | 7.2 g | 0.55 g | 92.13% | 5.01 |
| 45 hr. | 4.8 g | 0.34 g | 87.01% | 2.96 |
| 50 hr. | 7.2 g | 0.48 g | 61.76% | 2.96 |

(xxv)
| Medium: C-1 | Medium: C-2 |
|---|---|
| 4 g/L (NH$_4$)$_2$SO$_4$ | 2% Beef extract |
| 0.04 g/L FeSO$_4$ | 0.1% Yeast extract |
| 1 g/L Yeast extract | |
| 1 g/L Beef extract | 0.02% TWEEN ® 80 |
| 1 g/L KH$_2$PO$_4$ | 5% Castor Oil. |
| 0.5 g/L MgSO$_4$.7H$_2$O | |
| 0.1 g/L Primagen | |
| 0.2 g/L TWEEN ® 80 | |
| 5% Castor oil. | |

Conditions:
pH = 6.5
Back pressure = 7.5 psi
Aeration = 0.25 v/v/min.
Agitation = 300 RPM
Temperature: 27° C.
Inoculum: 3% *Candida petrophilum*, ATCC 20226

| | Time | Crude Wt. | Distilled Wt. | % Purity | Yield (g/L) |
|---|---|---|---|---|---|
| C-1 | 24 hr. | 4.4 g | 0.2 g | 83.03 | 1.66 |
| C-2 | 24 | 4.6 | 0.17 | 95.05 | 1.62 |
| C-1 | 29 | 5.8 | 0.2 | 84.38 | 1.69 |
| C-2 | 29 | 3.6 | 0.21 | 91.6 | 1.92 |
| C-1 | 31.5 | 1.3 | 0.17 | 67.01 | 1.14 |
| C-2 | 31.5 | 4.8 | 0.21 | 87.3 | 1.83 |

(xxvi)
Medium: C-2  pH = 6.5
2% Beef extract  Back pressure = 7.5 psi
0.1% Yeast extract  Aeration = 0.5 v/v/min.
0.01% KH$_2$PO$_4$  Agitation = 400 RPM
0.005% MgSO$_4$.7H$_2$O  Temperature = 27° C.
0.02% TWEEN ® 80  3% Inoculum *Candida petrophilum*,
4% Castor Oil.  ATCC 20226

| Time Hr. | Crude Wt. | Distilled Wt. | % Purity | Yield (g/L) | dO$_2$ (%) |
|---|---|---|---|---|---|
| 24 | 4.6 g | 0.281 g | 89.4 | 2.5 | 35 |
| 30 | 4.6 | 0.172 | 85.16 | 1.46 | 45 |
| 1 g lipase, 15 g Castor Oil added. | | | | | |
| 32 | 5.3 | 0.334 | 13.68 | 0.46 ⎫ 2.19 | 22 |
|  |  | 0.200 | 86.47 | 1.43 ⎭ | |
| 37 | ½% Castor Oil added | | | | |
| 19 | | | | | |
| 48 | 8.5 | 0.210 | 89.27 | 1.87 | 46 |

Total NaOH added = 92.8 g
Total antifoam added = 600 ml
Phosphoric acid used = 188 g.

(xxvii)
Medium: C-1  pH = 6.5
2% Beef Extract  Back pressure = 7.5 psi
0.1% Yeast extract  Agitation = 400 RPM
0.01% KH$_2$PO$_4$  Temperature = 27° C.
0.005% MgSO$_4$.7H$_2$O  Aeration = 0.5 v/v/min.
4% Castor Oil.
0.02% TWEEN ® 80  3% inoculum
*Candida petrophilum*,
ATCC 20226.

| Time Hr. | Crude Wt. | Distilled Wt. | % Purity | Yield (g/L) | dO$_2$ (%) |
|---|---|---|---|---|---|
| 23 | 3.8 g | 0.274 g | 83.81 | 2.3 | 13 |
| 30 | 5.4 | 0.342 | 78.00 | 2.67 | 58 |

Add 0.2% capric Acid, lower pH + 0 = 6, lower aeration + 0 0.25 v/v/min.

| 42 | 4.2 | 0.15 | 56.25 | 0.84 | 58 |

Total NaOH added = 77.3 g
Total antifoam added = 300.5 g
Phosphoric acid used = 595 g.

(xxviii)
Medium: 2% Beef extract  C-1  pH = 6.5
0.1% Yeast extract  4% Castor oil  400 RPM
0.01% KH$_2$PO$_4$  7.5 psi back pressure
0.005% MgSO$_4$.7H$_2$O  C-2  27° C.
2% Castor oil  0.5 v/v/min.
0.02% TWEEN ® 80
3% Inoculum *Candida petrophilum*, ATCC 20226

| | Time Hr. | Crude Wt. | Distilled Wt. | % Purity | Yield (g/L) | dO$_2$ (%) |
|---|---|---|---|---|---|---|
| C1 | 16 | 4.6 g | 0.12 g | 79.36 | 0.95 | 0 |
| C2 | 16 | 3.1 | 0.14 | 52.8 | 0.74 | 32 |
| C1 | 24 | 5.9 | 0.11 | 74.03 | 0.81 | 8 |
| C2 | 24 | 2.9 | 0.29 | 24.33 | 0.71 | 8 |
| 0.05% Capric Acid added to each fermenter. | | | | | | |
| C1 | 30 | 5.7 | 0.21 | 63.39 | 1.33 | 31 |
| C2 | 30 | 2.7 | 0.24 | 5.39 | 0.13 | 18 |

Total NaOH added:  Total antifoam added:
C1 134 g  C1 293 g
C2 60 g  C2 171 g.

(xxix)
800 L  pH = 6.5
2% Beef extract  Temperature = 27° C.
0.1% Yeast extract
0.02% KH$_2$PO$_4$
0.005% MgSO$_4$.7H$_2$O
0.02% TWEEN ® 80
0.05% Antifoam
4% Castor Oil
Inoculum 3% *Candida petrophilum*, ATCC 20226

| Time Hr. | Crude Wt. | Distilled Wt. | % Purity | Yield g/L |
|---|---|---|---|---|
| 22 | 3.0 g | 0.26 g | 3.03 | 0.08 |
| 24 | 2.9 | 0.20 | 3.48 | 0.07 |
| 30 | 2.3 | 0.28 | 75.45 | 2.11 |

(xxx)
| C-1 | 2% Beef extract | C-2 | 2% Beef extract |
|---|---|---|---|
| | 0.2% Yeast extract | | 0.5% Yeast extract |
| | 0.1% KH$_2$PO$_4$ | | 0.1% KH$_2$PO$_4$ |
| | 0.05% MgSO$_4$.7H$_2$O | | 0.05% MgSO$_4$.7H$_2$O |
| | 0.02% TWEEN ® 80 | | 0.02% TWEEN ® 80 |
| | 0.05% Antifoam | | 0.05% Antifoam |
| | 5% Castor Oil | | 5% Castor Oil |

Inoculum: 3% *Candida petrophilum*, ATCC 20226 (1% Olive Oil)
27° C.  pH = 6.5
400 RPM  7.5 psi back pressure
0.5 v/v/min

| Time | Crude | Distilled | % | Yield | dO$_2$ |

-continued

| Hr. | | Wt. | Wt. | Purity | (g/L) | (%) |
|---|---|---|---|---|---|---|
| 24 Hr | C1 | 7.7 g | 0.21 g | 72.27 | 1.52 | 47 |
| | C2 | 8.3 | 0.22 | 89.49 | 1.97 | 2 |
| 30 Hr | C1 | 8.7 | 0.38 | 38.65 | 3.6 | 60 |
| | | | 0.22 | 96.7 | | |
| | C2 | 8.7 | 0.40 | 19.4 | 0.78 | 9 |
| 32 Hr | C1 | 8.8 | 0.25 | 54.64 | 4.67 | 62 |
| | | | 0.345 | 95.7 | | |
| 35 Hr | C2 | 10.5 | 0.25 | 85.52 | 2.14 | 24 |

Total NaOH added:
C1   131 g
C2   131 g

Total Antifoam added:
C1 = 566 g
C2 = 765 g

---

(xxxi)
800 L
2% Beef extract
0.1% Yeast extract
0.01% $KH_2PO_4$
0.005% $MgSO_4.7H_2O$
0.02% TWEEN ® 80
0.05% Antifoam
5% Castor Oil
3% Inoculum *Candida petrophilum*, ATCC 20226
(1% Olive Oil)

| Time | Crude Wt | Distilled Wt | % Purity | Yield (g/L) |
|---|---|---|---|---|
| 24 hr. | 4.7 g | 0.21 g | 75.79 | 1.59 |
| 29 hr. | 4.6 | 0.322 | 89.66 | 2.89 |
| 32 hr. | | 0.40 | 66.89 | 2.68 |
| 35 hr. | 4.3 | 0.87 | 5.42 | 0.47 |

---

(xxxii)
C-1 Medium:
3% Beef extract
0.1% Yeast extract
0.1% $KH_2PO_4$
0.05% $MgSO_4.7H_2O$
0.02% TWEEN ® 80
0.05% Antifoam
10% Castor Oil Temperature = 27° C.
Aeration = 0.5 v/v/min.
Agitation = 400 RPM
Backpressure = 7.5 psi
pH = 6.0

3% Inoculum *Candida petrophilum*, ATCC 20226 (1% Olive Oil)
100 ml Samples

| Time | Crude Wt | Distilled Wt | % Purity | Yield (g/L) | $dO_2$ (%) |
|---|---|---|---|---|---|
| 24 hr | 9.3 g | 0.31 g | 32.5 | 3.24 | 9 |
| | | 0.24 | 92.83 | | |
| 30 hr | 7.0 | 0.62 | 92.8 | 5.75 | 40 |

Total NaOH added = 91 g
Total antifoam added = 32 g

---

(xxxiii)
800 L
Medium: 2% Beef extract
0.2% Yeast extract
0.01% $KH_2PO_4$
0.005% $MgSO_4.7H_2O$
0.02% TWEEN ® 80
0.05% Antifoam
5% Castor Oil pH = 6.5
Aeration = 0.5 v/v/min.
Temperature = 27° C.

3% inoculum: *Candida petrophilum*, ATCC 20226 (1% Olive Oil)

| Time | Crude Wt | Distilled Wt | % Purity | Yield (g/L) |
|---|---|---|---|---|
| 24 hr | 3.9 g | 0.83 g | 21.54 | 1.79 |
| 30 hr | 3.4 | 0.40 | 90.68 | 3.63 |

---

(xxxiv)
Medium: 2% Beef extract
0.5% Yeast extract
0.1% $KH_2PO_4$
0.05% $MgSO_4.7H_2O$
0.02% TWEEN ® 80
0.05% Antifoam
10% Castor Oil Temperature = 27° C.
Aeration = 0.5 v/v/m
Backpressure = 7.5 psi
Agitation = 400 RPM
C1 pH = 6.0
C2 pH = 5.5

3% Inoculum: *Candida petrophilum*, ATCC 20226 (1% Olive Oil)

| | Crude Wt | Distilled Wt | % Purity | Yield (g/L) | $dO_2$ (%) |
|---|---|---|---|---|---|
| 22 Hrs. | | | | | |
| C1 | 9.5 g | 0.38 g | 64.49 | 2.45 | 12 |
| C2 | 8.2 | 0.40 | 82.21 | 3.29 | 0 |
| 29 Hrs. | | | | | |
| C1 | 9.4 g | 0.65 g / 0.26 g | 11.73 / 88.14 | 0.76 / 2.29 } 3.05 | 15 |
| C2 | 7.9 g | 0.39 g / 0.32 g | 18.62 / 87.73 | 3.54 | 20 |
| 48 Hrs. | | | | | |
| C1 | 6.0 g | 0.22 | 79.03 | 5.13 | 35 |
| C2 | 6.6 | 0.36 | 94.12 | | |
| 52 Hrs. | | | | | |
| C1 | 7.6 g | 0.9 / 1.44 | 80.24 / 40.74 | 13.09 | 37 |
| C2 | 6.9 | 0.31 / 0.54 | 80.87 / 16.73 | 3.41 | 36 |

Total NaOH added:
C1 = 158 g
C2 = 61 g

Total Antifoam added:
C1 = 27 g FG. 10
C2 = 65 g SAG 5693

---

(xxxv)
800 L Pilot Plant
2% Beef extract
0.2% Yeast extract
0.1% $KH_2PO_4$
0.05% $MgSO_4.7H_2O$
0.02% TWEEN ® 80
0.05% Antifoam
10% Castor Oil pH = 6
Agitation = 75 RPM
Aeration: 0.5 v/v/min.

3% Inoculum *Candida petrophilum*, ATCC 20226

| Time | Crude Wt | Distilled Wt | % Purity | Yield (g/L) |
|---|---|---|---|---|
| 24 Hr | 2.0 g | 0.37 g | 60.25 | 2.23 |
| 30 Hr | 8.5 g | 0.55 g / 0.64 g | 84.61 / 15.33 } | 5.63 |

---

(xxxvi)
C-1 10 L
Medium: 2% Beef extract
0.5% Yeast extract
0.1% $KH_2PO_4$
0.05% $MgSO_4.7H_2O$
0.02% TWEEN ® 80
0.05% Antifoam
10% Castor Oil pH = 6
Agitation = 420 RPM
Aeration = 0.5 v/v/min.
7.5 psi Backpressure 3% Inoculum *Candida petrophilum*, ATCC 20226

| Time Hr. | Crude Wt | Distilled Wt | % Purity | Yield (g/L) | $dO_2$ (%) |
|---|---|---|---|---|---|
| 24 h | 10.3 g | 0.99 g | 65 | 6.44 | 1 |
| 30 h | 6.7 g | 0.29 g / 0.29 g | 79 / 25 | 4.13 | 14 |
| 48 h | 7.5 g | 0.62 g / 0.66 g / 0.78 g | 84 / 28 / 68 | 7.0 | 42 |

|     |       |         |    |      |    |
|-----|-------|---------|----|------|----|
| 52 h | 7.3 g | 1.04 g | 11 | 6.44 | 44 |

(xxxvii)

| 800 L - Pilot Plant Medium: | Batch 6 Conditions: |
|---|---|
| 2% Beef extract | Agitation = 70 RPM |
| 0.5% Yeast extract | Aeration = 0.5 v/v/m |
| 0.1% $KH_2PO_4$ | pH = 6 |
| 0.05% $MgSO_4.7H_2O$ | |
| 0.02% TWEEN ® 80 | |
| 0.05% Antifoam | |
| 10% Castor Oil | |

3% Inoculum *Candida petrophilum*, ATCC 20226

| Time Hr. | Crude Wt | Distilled Wt | % Purity | Yield | (g/L) |
|---|---|---|---|---|---|
| 24 | 9.1 g | 0.94 g | 77 | 3.77 | |
| 32 | 8.5 g | 0.83 g | 40 | | 3.53 |
|   |       | 0.58 g | 37 | |      |
| 48 | 6.8 g | 0.67 g | 66 | | 5.39 |
|   |       | 0.88 g | 11 | |      |
| Final 48 hr. | 8.5 g | 0.78 g | 74 | 5.77 | Batch 7 |
|   |       | 0.22 g | 24 | 0.53 | 1-10-87 |

(xxxviii)

| C-3 10 L | |
|---|---|
| Medium: | Conditions: |
| 3% Amberex 5500 | Agitation = 420 RPM |
| 0.1% $KH_2PO_4$ | Aeration = 0.5 v/v/min. |
| 0.05% $MgSO_4.7H_2O$ | Temperature = 27° C. |
| 0.02% TWEEN ® 80 | pH = 6 |
| 0.05% Antifoam | |

3% Inoculum *Candida petrophilum*, ATCC 20226

| Time | Crude Wt | Distilled Wt | % Purity | Yield | |
|---|---|---|---|---|---|
| 24 Hr | 1.3 g | 0.56 g | 60 | 3.36 | |
|   |       | 0.54 g | 8  | .43 | 3.79 g/L |
| 40 Hr | 6.8 g | 0.54 g | 67 | 3.62 | |
|   |       | 1.42 g | 27 | 3.83 | 7.45 g/L |
| 48 Hr | 7.3 g | 0.98 g | 60 | 5.88 | |
|   |       | 2.4 g  | 30 | 7.2  | 13.08 g/L |
| 64 Hr | 5.7 g | 0.68 g | 70 | 4.76 | |
|   |       | 2.51 g | 26 | 6.53 | 11.29 g/L |

(xxxix)

| C-2, C-3 10 L | |
|---|---|
| Medium: | Conditions: |
| 3% Amberex 5500 | Agitation = 420 RPM |
| 0.1% $KH_2PO_4$ | Aeration = 0.5 v/v/min. |
| 0.05% $MgSO_4.7H_2O$ | Temperature = 28° C. |
| 0.02% TWEEN ® 80 | pH C-2 = 6 |
| 0.005% Antifoam (FG-10) | pH C-3 = 7 |

3% Inoculum *Candida petrophilum*, ATCC 20226

| Time | Crude Wt | Distilled Wt | % Purity | Yield (g/L) | dO₂ (%) |
|---|---|---|---|---|---|
| 24 Hr. | | | | | |
| C2 | 8.2 g | 0.23 g, 0.71 g | 60.8, 10.2 | 2.12 | 8 |
| C3 | 8.4 g | 0.89 g, 1.36 g | 21.3, 41.15 | 7.5 | 6 |
| 30 Hr. | | | | | |
| C2 | 8.8 g | 0.39 g, 0.53 g | 53.2, 6.31 | 2.40 | 14 |
| C3 | 7.6 g | 0.56 g, 0.93 g | 27.68, 5.52 | 2.06 | 0 |
| 48 Hr. | | | | | |
| C2 | 5.5 g | 0.28, 1.01 g | 50.18, 8.26 | 2.66 | 14 |
| C3 | 4.9 g | | | | 16 |
| 50 Hr. | | | | | |
| C2 | 7.9 g | 0.83 g, 1.07 g | 28.9, 14.45 | 3.95 | 2 |
| C3 | 6.2 g | 0.62 g, 1.9 g | 56.03, 6.42 | 4.69 | 18 |

| Total NaOH added: | Total Antifoam added: | % Purity correct |
|---|---|---|
| C-2 = 213 g | C-2 = 110 g | with internal std. |
| C-3 = 358 g | C-3 = 111 g | 1.19 correction factor. |

(xi)

800 L Batch 8
2% Beef Extract
0.5% Yeast extract
0.1% $KH_2PO_4$
0.05% $MgSO_4.7H_2O$
0.02% TWEEN ® 80
0.05% Antifoam

|   | Crude | Distilled | % Purity | Yield | |
|---|---|---|---|---|---|
| 48 Hr. | 8.4 g | 0.60 g | 69 | 4.14 | |
|   |       | 0.74 g | 11 | 0.81 | 4.95 g/L |

Batch 9 - Temperature controller malfunction

|   | Crude | Distilled | % Purity | Yield | |
|---|---|---|---|---|---|
| 48 Hr. | 8.28 | 0.38 g | 69.4 | 2.37 | |
|   |      | 0.32 g | 1.3  | 0.04 | 2.41 g/L |

EXAMPLE V

PREPARATION OF MIXTURE OF LACTONES

Reactions:

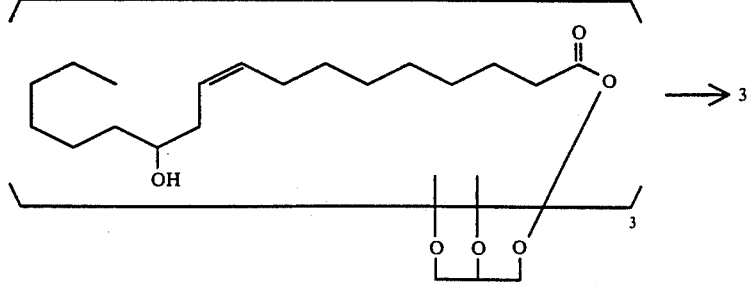

(i)

Reactions:
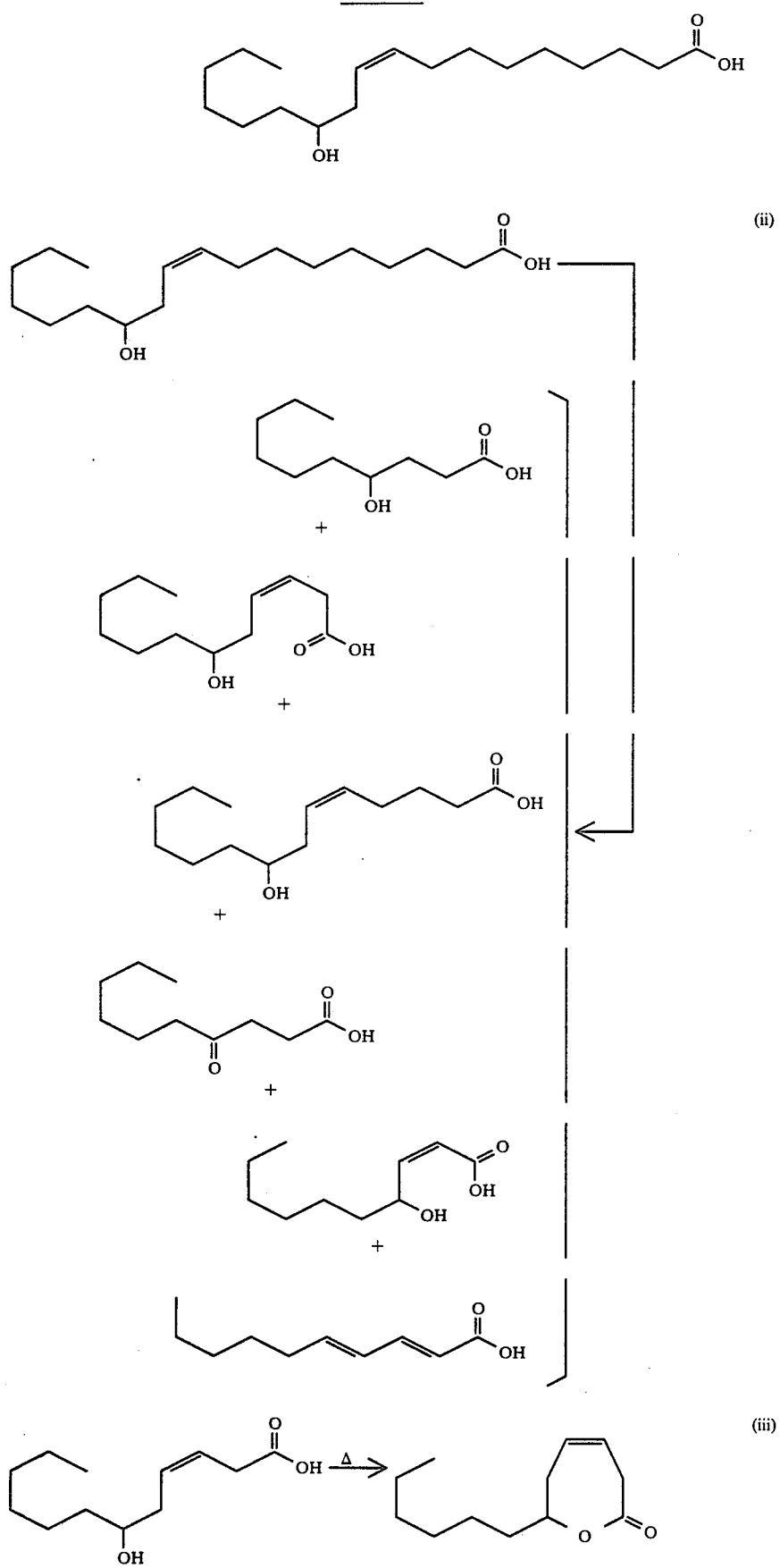
(ii)
(iii)

Reactions:

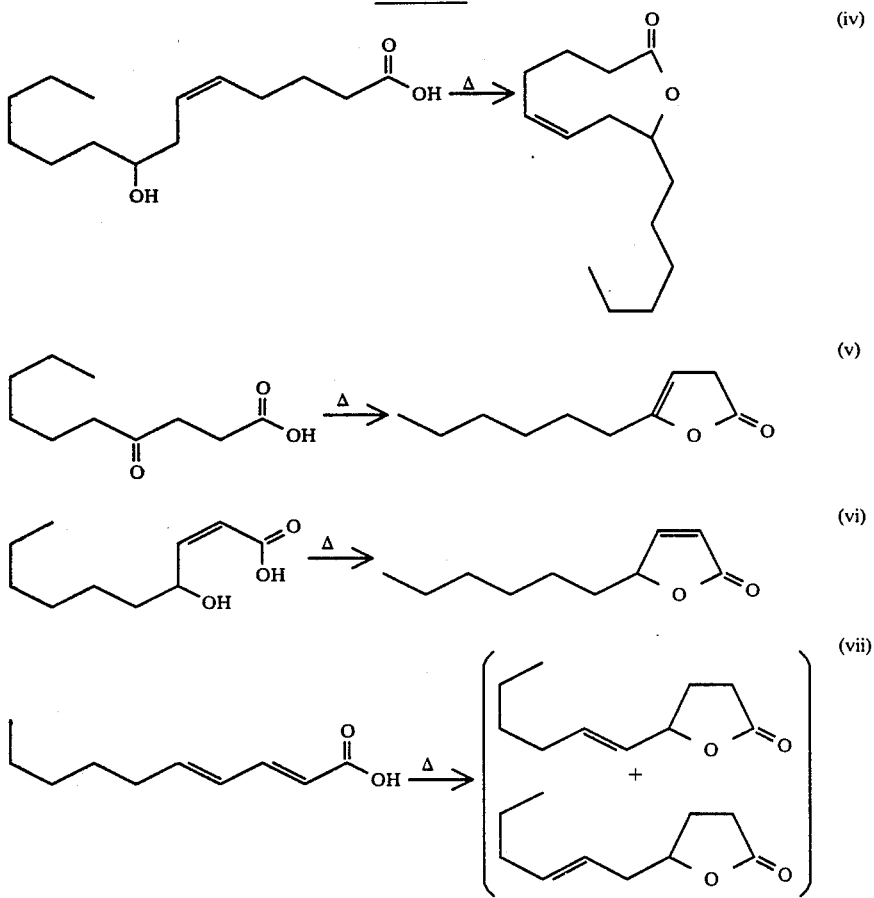

and

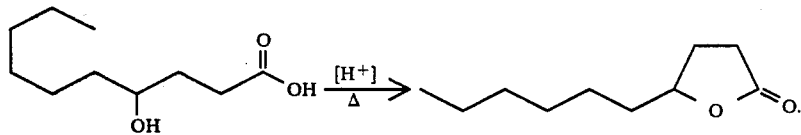

Using the same conditions as Example III a fermentation reaction was carried out. The fermentation batch after extraction and evaporation of solvent was distilled on a 12″ Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 188/145 | 183/185 | 16.5/14.5 | 2:1 |
| 2 | 150 | 185 | 14.5 | 2:1 |
| 3 | 153 | 185 | 14.5 | 2:1 |
| 4 | 154 | 186 | 14.0 | 2:1 |
| 5 | 155 | 187 | 14.0 | 2:1 |
| 6 | 155 | 187 | 14.0 | 2:1 |
| 7 | 155 | 189 | 14.0 | 2:1 |
| 8 | 155 | 189 | 14.0 | 2:1 |
| 9 | 155 | 190 | 14.0 | 2:1 |
| 10 | 155 | 191 | 16.0 | 2:1 |
| 11 | 156 | 193 | 16.0 | 2:1 |
| 12 | 156 | 195 | 16.5 | 2:1 |
| 13 | 157 | 196 | 16.5 | 2:1 |
| 14 | 157 | 198 | 16.5 | 2:1 |
| 15 | 157 | 200 | 16.5 | 2:1 |
| 16 | 156 | 204 | 16.0 | 2:1 |
| 17 | 156 | 205 | 16.0 | 2:1 |
| 18 | 154 | 207 | 15.5 | 2:1 |
| 19 | 154 | 210 | 15.0 | 2:1 |
| 20 | 156 | 214 | 15.0 | 2:1 |
| 21 | 160 | 216 | 15.5 | 2:1 |
| 22 | 167 | 220 | 17.0 | 2:1 |
| 23 | 167 | 226 | 17.0 | 2:1 |
| 24 | 171 | 230 | 16.5 | 2:1 |
| 25 | 173 | 236 | 16.5 | 2:1 |
| 26 | 174 | 245 | 16.0 | 2:1 |
| 27 | 174 | 251 | 16.0 | 2:1 |

FIG. 6 is the GLC profile for fraction 23 (Conditions: 50 m×0.31 mm OV-1 column programmed at 75°–225° C. at 2° C. per minute).

FIG. 7 is the GLC profile for fraction 24 of the foregoing distillation.

FIG. 8 is the GLC profile for fraction 1 of the foregoing distillation. The peak indicated by reference numeral 80 is the peak for the compound having the structure:

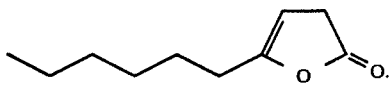

The resulting product (bulked fractions 2-25) has a lactonic coconut and peach aroma and taste profile at 1 ppm causing it to be useful in coconut, apricot, peach and vanilla-flavored foodstuffs.

EXAMPLE VI

PATCHOULI PERFUME FORMULATION

The following mixture is prepared:

| Ingredients | Parts by Weight |
|---|---|
| Orange oil | 50 |
| Bergamot oil | 20 |
| Lime oil | 100 |
| Neroli oil | 5 |
| 4-(4-methyl-4-hydroxyamyl)delta$^3$-cyclohexene carboxaldehyde | 5 |
| 2,3,3A,4,5,7A-hexahydro-6,7A,8,8-tetramethyl-1,5,methano-1H-inden-1-ol (prepared according to the process of Example I of U.S. Pat. No. 3,989,760 issued on November 2, 1976) | 100 |
| 1',2',3',4',5',6',7',8'-octahydro 2',3',8',8'-tetramethyl-2'aceto-naphthone isomer mixture produced according to the process of Example VII of Application for U.S. Letters Patent, Ser. No. 434,948 filed on January 21, 1974, now U.S. Letters Patent No. 3,911,018 issued on October 7, 1975 | 50 |
| Gamma methyl ionone | 20 |
| 1-acetyl-2,5,5-trimethylcyclo-heptane produced according to U.S. Pat. No. 3,869,411 issued on March 4, 1975 | 50 |
| Mixture of compounds prepared according to Example I | 150 |

The mixture of lactones prepared according to Example I add to this patchouli formulation a sophisticated, sweet, fruity, peach-like aroma profile with green and herbaceous topnotes.

EXAMPLE VII

PREPARATION OF SOAP COMPOSITIONS

One hundred grams of soap chips are produced according to Example V of U.S. Pat. No. 4,058,487 issued on Nov. 15, 1977, the specification for which is incorporated herein by reference, as follows:

The sodium salt of an equal mixture of $C_{10}$-$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated coconut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 pounds of water, 0.2 pounds of titanium hydroxide and 0.7 pounds of one of the perfume ingredients set forth in Table I below. The chips are then plodded into logs, cut to size and finally stamped into bars having a pH of approximately 6.9.

Each of the perfumed soaps produced by means of the foregoing procedure manifests an excellent aroma as set forth in Table I, infra.

TABLE I

| Ingredient | Fragrance Profile |
|---|---|
| Mixture of compounds produced according to Example I, bulked fractions 1-19. | A peach aroma. |
| Mixture of lactones produced according to Example I, bulked fractions 23-27. | A peach and apricot aroma profile. |
| Perfume composition of Example VI. | A patchouli aroma with peach-like undertones and herbaceous topnotes. |

EXAMPLE VIII

PREPARATION OF A DETERGENT COMPOSITION

A total of 100 grams of a detergent powder prepared according to U.S. Pat. No. 4,058,472 (the specification for which is incorporated by reference herein) and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol and 40 parts by weight of di-$C_{14}$-$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table I of Example VII until a substantially homogeneous composition is obtained. Each of the compositions has an excellent aroma as set forth in Table I of Example VII.

EXAMPLE IX

PREPARATION OF A COSMETIC POWDER COMPOSITION

A cosmetic powder is prepared by mixing in a ball mill, 100 grams of talcum powder with 0.25 grams of each of the perfume materials of Table I of Example VII. Each of the powders has an excellent aroma as set forth in Table I of Example VI.

EXAMPLE X

PERFUMED LIQUID DETERGENT

Concentrated liquid detergents with aromas as set forth in Table I of Example VII are prepared by adding 0.10%, 0.15% and 0.20% of each of the ingredients set forth in Table I of Example VII. They are prepared by adding and homogeneously mixing the appropriate quantity of perfume substance of Table I of Example VII in the liquid detergent. The detergents individually possess aromas as set forth in Table I of Example VII, the intensity increasing with greater concentrations of perfume substance set forth in Table I of Example VII.

EXAMPLE XI

PREPARATION OF A COLOGNE AND HANDKERCHIEF PERFUME

Each of the ingredients of Table I of Example VII is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table I of Example VII are imparted to the colognes and to the handkerchief perfumes at the several concentrations set forth above.

EXAMPLE XII

PREPARATION OF SOAP COMPOSITIONS

One hundred grams of soap chips (IVORY ® produced by the Proctor & Gamble Company of Cincinnati, Ohio) are admixed with one gram of each of the substances set forth in Table I of Example VII, supra, until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example VII.

EXAMPLE XIII

PREPARATION OF SOLID DETERGENT COMPOSITIONS

Detergents are prepared from the following ingredients according to Example I of Canadian Patent No. 1,007,948, the specification for which is incorporated by reference herein:

| Ingredients | Parts by Weight |
| --- | --- |
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of each of the substances set forth in Table I of Example VII, supra. Each of the detergent samples has an excellent aroma as indicated in Table I of Example VII.

EXAMPLE XIV

PREPARATION OF DRIER-ADDED FABRIC SOFTENER ARTICLE

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:
1. a water "dissolvable" paper ("Dissolvo Paper") as the substrate;
2. ADOGEN ® 448 (melting point about 140° F.) as the first substrate coating; and
3. an outer coating having the following formulation (melting point about 150° F.):
   57% $C_{20}$-$C_{22}$ HAPS;
   22% isopropyl alcohol;
   20% antistatic agent; and
   1% of one of the perfumery substances set forth in Table I of Example VII, supra.

Fabric softening compositions containing the substances as set forth in Table I of Example VII, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table I of Example VII, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. Patent may be perfumed in their outer coating with from 0.25% up to 5% by weight of each of the perfuming substances of Table I of Example VII, supra.

EXAMPLE XV

HAIR PREPARATION

A "soft-feel, good-hold" hair spray is produced containing the following ingredients:

| Ingredients | Parts by Weight |
| --- | --- |
| Polyvinylpyrollidone/vinyl acetate "E-735 Copolymer" manufactured by the GAF Corporation of New York, N.Y. | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, N.Y. | 24.95 |
| Fragrance ingredient as set forth in Table I of Example VII, supra. | 0.05 |

The PVP/VA copolymers are first dissolved in alcohol and all other ingredients are added until uniform. The propellant is then pressurized and used as an aerosol. The resulting hair sprays each have pleasant aromas as set forth in Table I of Example VII.

EXAMPLE XVI

SCOURING CLEANSER COMPOSITION

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table I of Example VII, supra, are added at the level of 0.25% as set forth in the table in said Example I of U.S. Pat. No. 4,193,888 yielding an aroma on using said cleanser in ordinary circumstances which is quite pleasant and described in Table I of Example VII, supra.

EXAMPLE XVII

A fabric softening article prepared substantially as set forth in Example VIII of Canadian Patent No. 1,069,260, the specification for which is incorporated by reference herein, is prepared containing 0.21% by weight of a perfuming substance as set forth in Table I of Example VII, supra, and yielding on use in a drier, a faint aroma as set forth in Table I of Example VII, supra.

EXAMPLE XVIII

TOBACCO FLAVOR FORMULATIONS

Cigarettes are produced using the following tobacco formulations:

| Ingredients | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| $H_2O$ | 5.3 |

At the rate of 0.2%, the following tobacco formulation is applied to all of the cigarettes produced with the above tobacco formulation:

| Ingredients | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol (95%) | 20.00 |
| $H_2O$ | 41.900 |

To portions of 50% of the cigarettes at levels of 10 and 20 ppm, a mixture of lactones produced according to Example II is added. These cigarettes are hereinafter called "experimental" cigarettes. The cigarettes without the mixture of lactones are hereinafter called "control" cigarettes. The control and experimental cigarettes are then evaluated by paired comparison and the results are as follows:

(a) In aroma, the experimental cigarettes are all found to be more aromatic with Turkish tobacco-like nuances.
(b) In smoke flavor, the experimental cigarettes are all found to be more aromatic, more sweet with Turkish tobacco, oriental-like nuances than the control cigarettes.

The experimental cigarettes containing the mixture of lactones are found to be fruity and have pleasant aesthetically pleasing fruity notes in addition.

EXAMPLE XIX

PUDDING

At the rate of 0.8 ppm the mixture of lactones produced according to Example V, bulked fractions 4-9 are added to a royal butterscotch pudding. Pleasant aesthetically pleasing peach nuances were added to the butterscotch pudding causing a panel of 30 members to prefer the butterscotch pudding with the mixture of lactones added thereto to a butterscotch pudding without the mixture of lactones added thereto.

EXAMPLE XX

FLAVOR FORMULATION

The following natural rich orange formulation is prepared:

| Ingredients | Parts by Weight |
|---|---|
| Compound defined according to the structure: 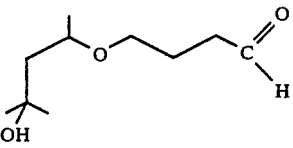 prepared according to Example VI of U.S. Letters Patent No. 4,532,364 | 26.0 |
| Mixture of lactones produced according to Example V bulked fraction 4-9. | 12.0 |
| Natural Lemon Oil Terpeneless | 10.0 |
| Acetaldehyde | 0.6 |
| Alpha-terpineol | 2.1 |
| Citral | 1.8 |
| Carvone | 0.24 |
| Terpinolene | 1.2 |
| Alpha-terpinene | 0.25 |
| Diphenyl | 0.25 |
| Alpha-Fenchyl Alcohol | 0.25 |
| Limonene | 0.35 |
| Linalool | 0.25 |
| Geranyl Acetate | 0.25 |
| Nootkatone | 0.25 |
| Neryl Acetate | 0.25 |

A second flavor formulation is prepared which is identical to the above formulation, except without the lactones of Example V.

The flavor formulation with the lactones of Example V has a definite natural rich orange aroma with buttery nuances due to the addition of the buttery principals to this citrus flavor.

The citrus flavor with the lactones of Example V added thereto is used in the following examples.

EXAMPLE XXI

A.

POWDER FLAVOR COMPOSITION

20 Grams of the flavor composition of Example XX containing the lactones of Example V is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B.

SUSTAINED RELEASE FLAVOR

The following mixture is prepared:

| Ingredients | Parts by Weight |
|---|---|
| Liquid Citrus Flavor Composition of Example XX | 20.0 |
| Propylene glycol | 9.0 |
| CAB-O-SIL ® M-5 | 5.00 |
| (Brand of Silica produced by the Cabot Corporation of 125 High Street, Boston, Massachusetts 02210): | |
| Physical Properties: | |
| Surface area: | 200 m$_2$/gm |

| | |
|---|---|
| Nominal particle size: | 0.012 microns |
| Density: | 2.3 lbs/cu.ft. |

The Cab-O-Sil is dispersed in the liquid citrus flavor composition of Example XX with vigorous stirring, thereby resulting in a viscous liquid. 71 Parts by weight of the powder flavor composition of Part "A", supra, is then blended into the said viscous liquid, with stirring, at 25° C. for a period of 30 minutes resulting in a dry, free flowing sustained release flavor powder.

EXAMPLE XXII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XX is added to the solution which is then homogenized to form an emulsion having particle size typically in the range of 5–40 microns. This material is kept at 120° F. under which conditions the gelatin will not jell.

Coacervation is induced by adding, slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulphate at 65° C. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXIII

CHEWING GUM

100 Parts by weight of chicle are mixed with 4 parts by weight of the flavor prepared in accordance with Example XXI(B). 300 Parts of sucrose and 100 parts of corn syrup are added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long-lasting rich citrus flavor.

EXAMPLE XXIV

CHEWING GUM

100 Parts by weight of chicle are mixed with 18 parts by weight of the flavor prepared in accordance with Example XXII. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long-lasting rich citrus flavor.

EXAMPLE XXV

TOOTHPASTE FORMULATION

The following separate groups of ingredients are prepared:

| Parts by Weight | Ingredients |
|---|---|
| Group "A" | |
| 30.200 | Glycerine |
| 15.325 | Distilled Water |
| 10.100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Materials of Example XXI(B). |

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, the flavor of "D" is added and lastly the sodium n-lauroyl sarcosinate;
5. The resultant slurry is then blended for one hour. The completed paste is then transferred to a three roller mill and then homogenized, and finally tubed.

The resulting toothpaste when used in a normal toothbrushing procedure yields a pleasant rich citrus flavor, of constant strong intensity throughout said procedure (1–1.5 minutes).

EXAMPLE XXVI

CHEWABLE VITAMIN TABLETS

The flavor material produced accordig to the process of Example XXI(B) is added to a Chewable Vitamin Tablet Formulation at a rate of 10 gm/Kg which chewable vitamin tablet formuation is prepared as follows:

In a Hobart Mixer the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin $B_1$ (thiamine mononitrate) as ROCOAT ® thiamine mononitrate 33⅓% (Hoffman La Roche) | 4.0 |
| Vitamin $B_2$ (riboflavin) as ROCOAT ® riboflavin 33⅓% | 5.0 |
| Vitamin $B_6$ (pyridoxine hydrochloride) as ROCOAT ® pyridoxine hydrochloride 33⅓% | 4.0 |
| Niacinamide as ROCOAT ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XXI(B) | (as indicated above) |
| Certified lake color | 5.0 |
| Sweetener - sodium saccharin | 1.0 |
| Magnesikum stearate lubricant | 10.0 |
| Mannitol q.s. to make | 500.0 |

Preliminary tablets are prepared by slugging with flat-faced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong rich citrus flavor for a period of 12 minutes.

EXAMPLE XXVII

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60.0 |
| Licorice | 10.0 |
| Glycerine | 20.0 |
| Fig Juice | 4.6 |
| Prune Juice | 5.0 |
| Flavor Material of Example XXI(B) | 0.4 |

The resultant product is redried to a moisture content of 20%. On chewing, this tobacco has an excellent substantially consistent, long-lasting rich citrus and licorice aroma and taste profile in conjunction wth the tobacco note.

EXAMPLE XXVIII

To 100 parts by weight of GOYA® mango nectar (produced by the Goya Corporation of New York, N.Y.) is added 10 ppm of the mixture of lactones produced according to Example V, bulked fractions 4/9. The lactone mixture adds to the mango nectar a very natural nuance which although present in natural mango is lost in the canning process when the mango nectar is prepared and canned in the usual manner.

What is claimed is:

1. A mixture of unsaturated lactones and the saturated lactone, gamma-decalactone, each of which is defined according to the structure:

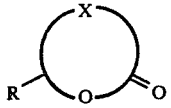

wherein R represents $C_6$ alkyl or alkenyl; and X represents $C_2$, $C_4$ or $C_6$ alkylene or alkenylene with the provisos that R is $C_6$ alkyl when X is $C_2$, $C_4$ or $C_6$ alkenylene or $C_2$ alkylene and R is $C_6$ alkenyl when X is $C_2$, $C_4$ or $C_6$ alkylene, said lactones having the structures:

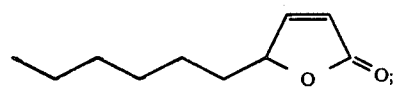

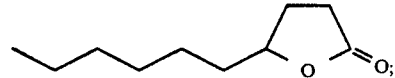

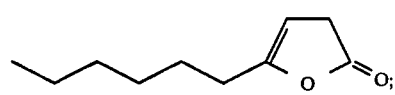

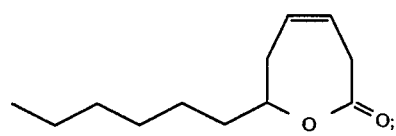

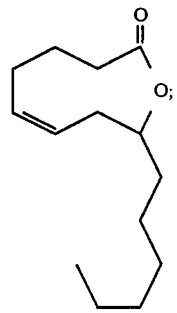

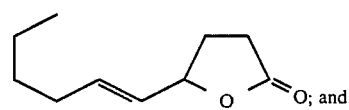

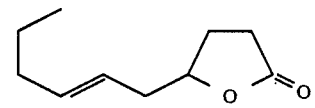

prepared according to the process consisting of the sequential steps of:

(i) fermenting at a pH in the range of from about 5.5 up to about 7 and at a temperature in the range of from about 20° C. up to about 35° C. castor oil, a castor oil hydrolysate or ricinoleic acid with a microorganism selected from the group consisting of:

Candida petrophilum, ATCC 20226;
Candida oleophila, ATCC 20177;
Candida sp., ATCC 20504; and
Candida sake, ATCC 28137 whereby gamma hydroxydecanoic acid and a mixture of other acids defined according to the generic structure:

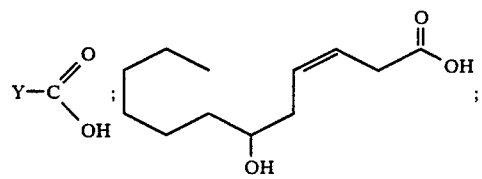

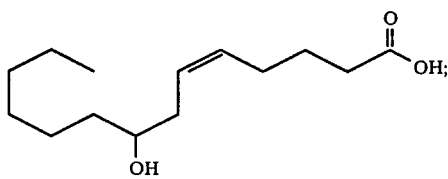

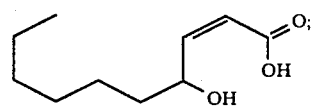

-continued

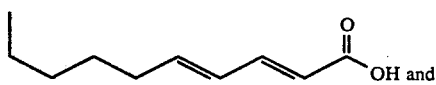

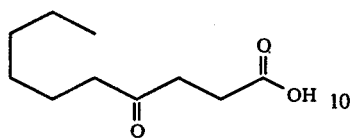

wherein Y represents an oxo-saturated, oxo-unsaturated or di-unsaturated $C_9$, $C_{11}$ or $C_{13}$ moiety according to the reaction:

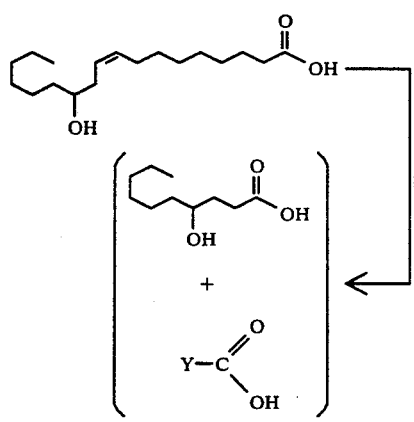

(ii) effecting the lactonization of the resulting gamma hydroxydecanoic acid at a pH in the range of 0-5 and at a temperature in the range of from about 90° C. up to about 120° C. by means of simultaneous acidification and heating according to the reaction:

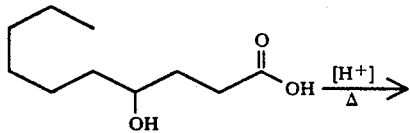

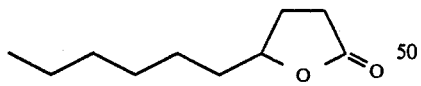

and then (iii) effecting lactonization by means of distillation at a temperature in the range of 120°-220° C. and at a pH of between about 1 and about 7 of the resulting acids defined according to the structure:

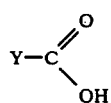

to form the mixture of lactones defined according to the structure:

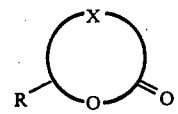

and having the structures:

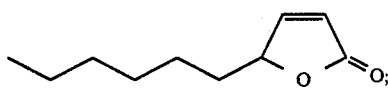

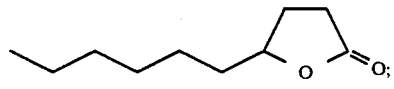

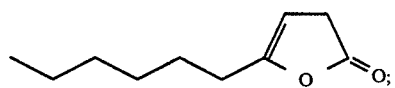

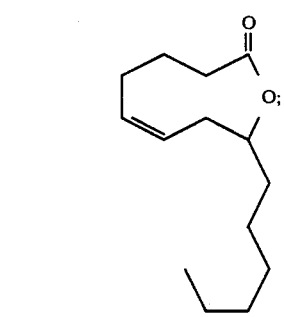

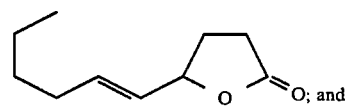

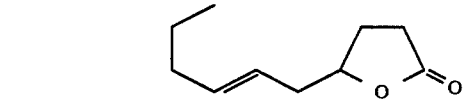

according to the reaction:

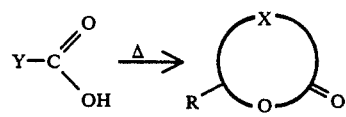

whereby the sum of the number of carbon atoms in the X moiety and in the R moiety is equal to the number of carbon atoms in the Y moiety minus 1.

* * * * *